(12) United States Patent
Liu et al.

(10) Patent No.: US 12,275,719 B2
(45) Date of Patent: Apr. 15, 2025

(54) SMALL MOLECULE INHIBITORS OF GALECTIN-3

(71) Applicant: BRISTOL-MYERS SQUIBB COMPANY, Princeton, NJ (US)

(72) Inventors: Chunjian Liu, Pennington, NJ (US); David S. Yoon, Ambler, PA (US); Wei Wang, Princeton, NJ (US); Jianxin Feng, Bensalem, PA (US); Bruce A. Ellsworth, Princeton, NJ (US); Alicia Regueiro-Ren, New Hope, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 799 days.

(21) Appl. No.: 17/439,845

(22) PCT Filed: Mar. 25, 2020

(86) PCT No.: PCT/US2020/024548
§ 371 (c)(1),
(2) Date: Sep. 16, 2021

(87) PCT Pub. No.: WO2020/198266
PCT Pub. Date: Oct. 1, 2020

(65) Prior Publication Data
US 2022/0185800 A1    Jun. 16, 2022

Related U.S. Application Data

(60) Provisional application No. 62/823,684, filed on Mar. 26, 2019.

(51) Int. Cl.
C07H 17/02    (2006.01)
C07D 405/14    (2006.01)
C07D 417/14    (2006.01)
C07H 19/056    (2006.01)

(52) U.S. Cl.
CPC ......... C07D 405/14 (2013.01); C07D 417/14 (2013.01); C07H 17/02 (2013.01); C07H 19/056 (2013.01)

(58) Field of Classification Search
None
See application file for complete search history.

(56) References Cited

U.S. PATENT DOCUMENTS 11,267,811 B2 *    3/2022    Jalagam ................. A61P 35/00

FOREIGN PATENT DOCUMENTS

| WO | 2005113569 A1 | 12/2005 |
| WO | 2016120403 A1 | 8/2016 |
| WO | 2018011094 A1 | 1/2018 |
| WO | 2018209255 A1 | 11/2018 |
| WO | 2019067702 A1 | 4/2019 |

* cited by examiner

*Primary Examiner* — Traviss C McIntosh, III
(74) *Attorney, Agent, or Firm* — Jing G. Sun

(57) ABSTRACT

The present disclosure relates to compounds of Formula (I), which inhibit Gal-3, and include pharmaceutically acceptable salts, compositions comprising such compounds, and methods using and making such compounds and compositions.

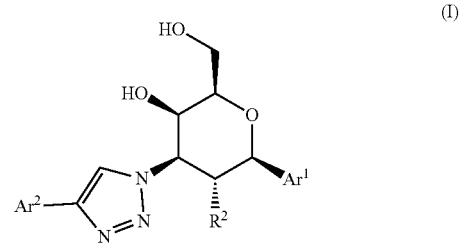

4 Claims, No Drawings

SMALL MOLECULE INHIBITORS OF GALECTIN-3

CROSS-REFERENCE TO RELATED APPLICATIONS

This application claims the priority benefit of U.S. Provisional Application No. 62/823,684, filed Mar. 26, 2019; the content of which is herein incorporated by reference in its entirety.

BACKGROUND OF THE INVENTION

Galectin-3 (Gal-3) is a β-galactoside binding lectin of about 30 KDa (Cell 76: 597-598), that is involved in the regulation of inflammatory and fibrotic processes. (Immunological Reviews 230: 160-171). Under uncontrolled inflammation and pro-fibrotic condition, Gal-3 promotes fibroblast proliferation and transformation and mediates collagen production (Circulation 110:3121-3128).

Gal-3 is localyzed in many cellular location such as cytoplasm, nucleus, and cell surface. Gal-3 is also secreted by various cell types, mainly macrophages and monocytes into the blood stream (J Pharmacol Exp Ther 351:336-343). There are multiple lines of evidence in the literature supporting the involment of Gal-3 in the development of fibrotic process in multiple organs such as lung (Am J. Respir. Crit. Care Med. 185: 537-546), liver (PNAS 103:5060-5065) and kidney (Am. J. Pathol. 172:288-298). Gal-3 has also been identified as a biomarker for heart failure indicating that modulation of Gal-3 has potential uses in the treatment of heart failure (Curr. Heart Fail. Rep. 7:1-8). Modulation of Gal-3 can be used in the treatment of cancer since Gal-3 is involved in cell growth and differentiation playing a critical role in angiogenic, apoptotic, and metastatic pathways (Galectin-3C: Human Lectin for Treatment of Cancer. ACS Symposium Series, Vol. 1115. Chapter 12, 195-23). Recently, Gal-3 inhibitors have proven to have positive effects when used in combination immunotherapy (Galectin Therapeutics. Press Release, Feb. 7, 2017).

Several publications and patent applications describe synthetic inhibitors of Gal-3 that are being explored as antifibrotic agents. Recent examples of these approach are WO2005113568, WO2005113569, US2014067986, WO2014067986, WO2017080971, WO2016120403, US20140099319, WO2014067986 and WO2018209255.

This application is a 371 of International Application No. PCT/US2020/024548 filed on Mar. 25, 2020, which claims the priority benefit of U.S. Provisional Application No. 62/823,684, filed Mar. 26, 2019; the content of which is herein incorporated by reference in its entirety.

DESCRIPTION OF THE INVENTION

The present disclosure relates to compounds of the present invention, which inhibit Gal-3, and include pharmaceutically acceptable salts, compositions comprising such compounds, and methods using and making such compounds and compositions.

In a 1st aspect, the present invention provides, inter alia, a compound of Formula (I):

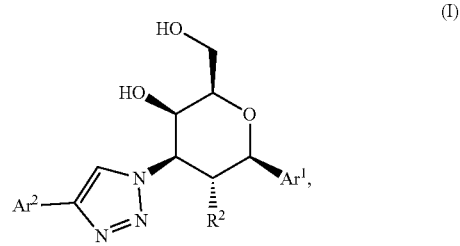

or a pharmaceutically acceptable salt thereof, wherein:
$Ar^1$ is independently selected from

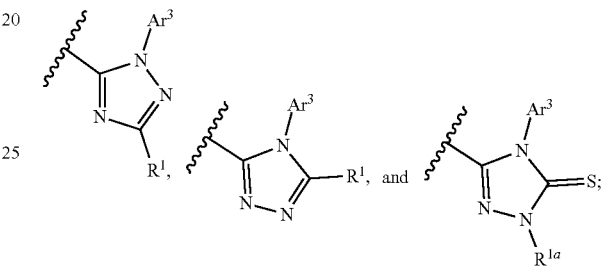

$Ar^2$ is independently phenyl or naphthyl; and wherein each ring moiety is substituted with 1 to 5 substituents selected from cyano, halogen, $C_{1-4}$ alkyl, $C_{1-4}$ alkoxy, $C_{1-4}$ haloalkyl, and $C_{1-4}$ haloalkoxy;
$Ar^3$ is independently selected from phenyl, pyridinyl and benzothiazolyl; and wherein each ring moiety is substituted with 0 to 3 substituents selected from cyano, halogen, $C_{1-4}$ alkyl, $C_{1-4}$ haloalkyl, $C_{1-4}$ alkoxy, $C_{1-4}$ haloalkoxy and $C_{3-6}$ cycloalkyl;
$R^1$ and $R^{1a}$ are independently H or $C_{1-4}$ alkyl; and
$R^2$ is independently selected from hydroxy, $C_{1-4}$ alkoxy, $C_{1-4}$ haloalkoxy, $-OCH_2C(O)OH$, $-OCH_2C(O)N(C_{1-2}$ alkyl)$(CH_2)_2NH(C_{1-4}$ alkyl), $-OCH_2C(O)-(C_{3-6}$ cycloalkyl), and $-OCH_2C(O)NH(C_{1-4}$ alkyl).

In a 2nd aspect, within the scope of the 1st aspect, wherein:
$Ar^1$ is independently

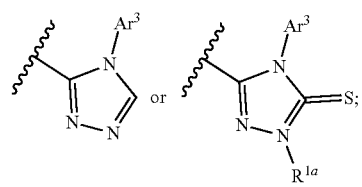

$Ar^2$ is independently phenyl substituted with 1 to 5 substituents selected from cyano, halogen, $C_{1-4}$ alkyl, $C_{1-4}$ alkoxy, $C_{1-4}$ haloalkyl, and $C_{1-4}$ haloalkoxy;
$Ar^3$ is independently selected from phenyl, pyridinyl and benzothiazolyl; and wherein each ring moiety is substituted with 0 to 3 substituents selected from cyano, halogen, $C_{1-4}$ alkyl, $C_{1-4}$ haloalkyl, $C_{1-4}$ alkoxy, $C_{1-4}$ haloalkoxy and $C_{3-6}$ cycloalkyl;

$R^{1a}$ is independently H or $C_{1-4}$ alkyl; and
$R^2$ is independently selected from hydroxy, $C_{1-4}$ alkoxy, $C_{1-4}$ haloalkoxy, —$OCH_2C(O)OH$, and —$OCH_2C(O)N(C_{1-2}$ alkyl)$(CH_2)_2NH(C_{1-4}$ alkyl).

In another aspect, wherein $Ar^1$ is

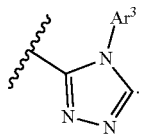

In another aspect, wherein $Ar^1$ is

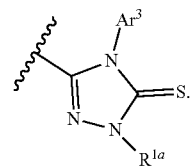

In another aspect, wherein $Ar^1$ is

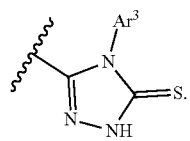

In another aspect, wherein $Ar^1$ is

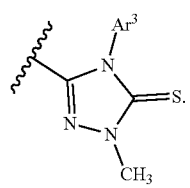

In a 3rd aspect, within the scope of the 2nd aspect, wherein:
$Ar^1$ is independently

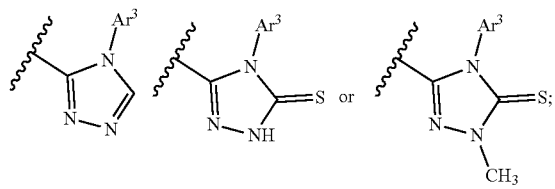

$Ar^2$ is independently phenyl substituted with 1 to 5 substituents selected from F, Cl and Br;
$Ar^3$ is independently phenyl, benzothiazolyl or quinolinyl; and wherein each ring moiety is substituted with 0 to 3 substituents selected from Cl, $CH_3$, $CF_3$, and —$OCF_3$; and
$R^2$ is independently selected from hydroxy, —$OCH_3$, —$OCH_2CHF_2$, —$OCH_2CF_3$, —$OCH_2CF_2CHF_2$, —$OCH_2C(O)OH$, and —$OCH_2C(O)N(CH_3)(CH_2)_2NH(CH_3)$.

In a 4th aspect, within the scope of the 2nd or 3rd aspect, wherein:
$Ar^2$ is independently selected from:

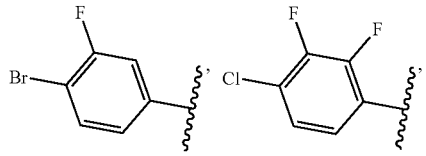

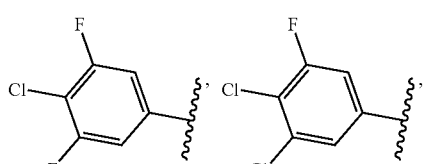

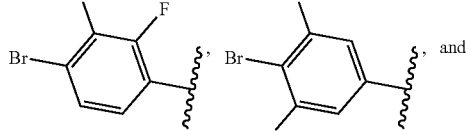

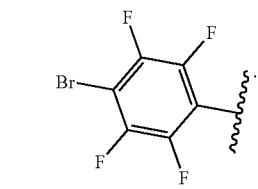

In a 5th aspect, within the scope of any of the 2nd to 4th aspects,
$Ar^3$ is independently selected from:

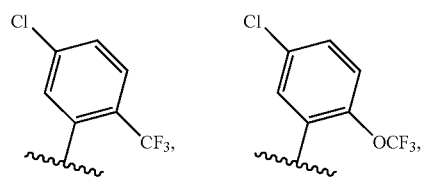

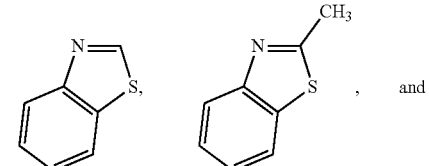

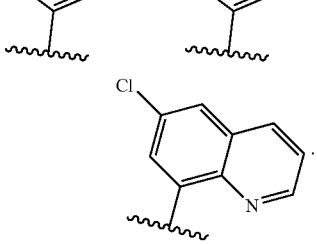

In a 6th aspect, within the scope of the 1st aspect, wherein the compound is of Formula (Ia):

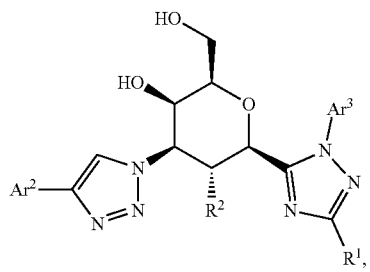

(Ia)

or a pharmaceutically acceptable salt thereof, wherein:
$Ar^2$ is independently phenyl or naphthyl; and wherein each ring moiety is substituted with 1 to 4 substituents selected from cyano, halogen, $C_{1-4}$ alkyl, $C_{1-4}$ alkoxy, $C_{1-4}$ haloalkyl, and $C_{1-4}$ haloalkoxy;
$Ar^3$ is independently selected from phenyl, pyridinyl and benzothiazolyl; and wherein each ring moiety is substituted with 0 to 3 substituents selected from cyano, halogen, $C_{1-4}$ alkyl, $C_{1-4}$ haloalkyl, $C_{1-4}$ alkoxy, $C_{1-4}$ haloalkoxy and $C_{3-6}$ cycloalkyl;
$R^1$ is independently $C_{1-4}$ alkyl; and
$R^2$ is independently selected from hydroxy, $C_{1-4}$ alkoxy, —OCH$_2$C(O)—($C_{3-6}$ cycloalkyl), and —OCH$_2$C(O)NH ($C_{1-4}$ alkyl).

In a seventh aspect, within the scope of the 6th aspect, wherein:
$Ar^2$ is independently phenyl or naphthyl; and wherein each ring moiety is substituted with 1 to 3 substituents selected from cyano, F, Cl, Br, CH$_3$, and —OCH$_3$;
$Ar^3$ is independently selected from phenyl, pyridinyl and benzothiazolyl; and wherein each ring moiety is substituted with 0 to 3 substituents selected from Cl, CF$_3$, —OCF$_3$, and cyclopropyl;
$R^1$ is CH$_3$; and
$R^2$ is independently selected from hydroxy, —OCH$_3$, —OCH$_2$C(O)-(cyclopropyl), and —OCH$_2$C(O)NH(CH$_3$).

In an eighth aspect, within the scope of the 6th or 7th aspect, wherein:
$Ar^2$ is independently selected from:

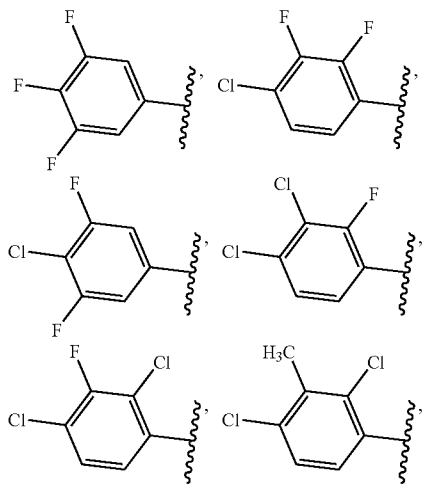

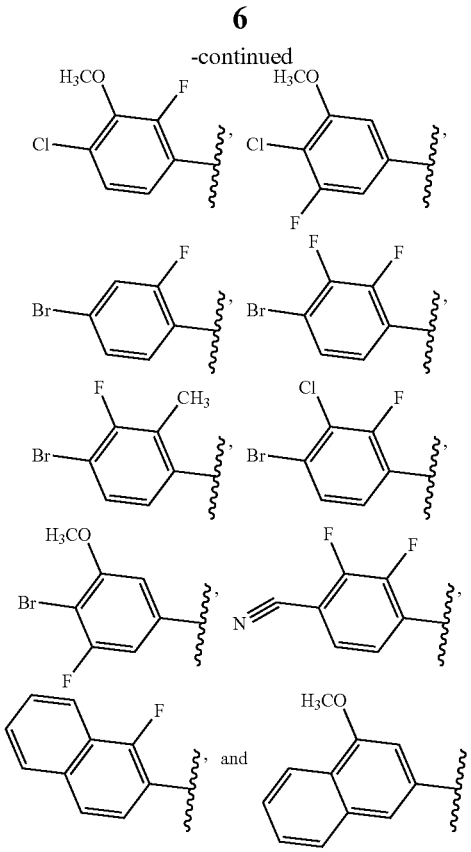

In a 9th aspect, within the scope of any of the 6th to 8th aspects,
$Ar^2$ is independently selected from:

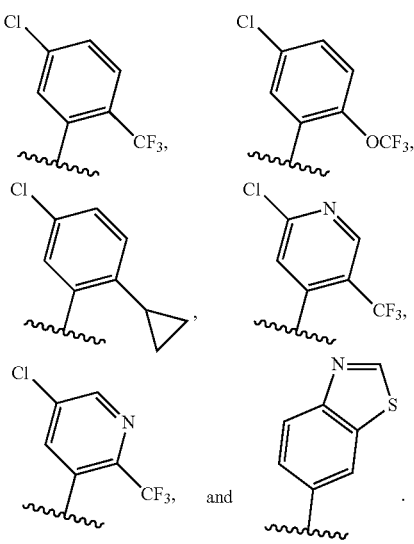

In a 10th aspect, within the scope of any of the 1st to 9th aspects, wherein $R^2$ is hydroxy.

In another aspect, the invention provides a compound selected from the exemplified examples or a pharmaceutically acceptable salt thereof.

In another aspect, the invention provides a compound selected from the Examples 1 to 75 or a pharmaceutically acceptable salt thereof.

In another aspect, the invention provides a compound selected from the Examples 1 to 25 or a pharmaceutically acceptable salt thereof.

In another aspect, the invention provides a compound selected from the Examples 26 to 75 or a pharmaceutically acceptable salt thereof.

Unless specified otherwise, these terms have the following meanings. "Alkyl" means a straight or branched alkyl group composed of 1 to 6 carbons. "Cycloalkyl" means a monocyclic ring system composed of 3 to 7 carbons. Terms with a hydrocarbon moiety (e.g. alkoxy) include straight and branched isomers for the hydrocarbon portion which are composed of 1 to 6 carbons. "Halo" includes fluoro, chloro, bromo, and iodo. "Haloalkyl" and "haloalkoxy" include all halogenated isomers from monohalo to perhalo. "Aryl" means a monocyclic or bicyclic aromatic ring system having 5 to 12 carbon atoms wherein one or both of the rings are aromatic. Representative examples of aryl groups include, but are not limited to, indanyl, indenyl, naphthyl, phenyl, and tetrahydronaphthyl. "Heteroaryl" means a 5 to 7 membered monocyclic or 8 to 11 membered bicyclic aromatic ring system with 1-5 heteroatoms independently selected from nitrogen, oxygen, and sulfur. Where a bonding attachment location is not specified, the bonding may be attached at any appropriate location as understood by practitioners in the art. Combinations of substituents and bonding patterns are only those that result in stable compounds as understood by practitioners in the art. Parenthetic and multiparenthetic terms are intended to clarify bonding relationships to those skilled in the art. For example, a term such as ((R)alkyl) means an alkyl substituent further substituted with the substituent R.

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

Some of the compounds of the invention exist in stereoisomeric forms. The invention includes all stereoisomeric forms of the compounds including enantiomers and diastereomers. Methods of making and separating stereoisomers are known in the art. The invention includes all tautomeric forms of the compounds. The invention includes atropisomers and rotational isomers.

The invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

Biological Methods

ASSAY BUFFER Composition: 25 mM HEPES, 100 mM NaCl, 0.005% Tween 20, 0.05% BSA prepared in sterile water (all reagents from Sigma).

CONTROLS:

Positive Control: 100% DMSO (1 µL)+His-tagged hGal-3 (20 µL)+β-ASF (20 µL)+Anti-His Terbium Antibody (5 µL)+Strep d2 Antibody (5 µL).

Negative Control: 100% DMSO (1 µL)+His-tagged hGal-3 (20 µL)+Anti His Terbium Antibody (5 µL)+Strep d2 Aantibody (5 µL).

| STOCKS PREPARATION: | | | | |
|---|---|---|---|---|
| | Stock Conc. | Intermediate Conc. | Final Assay Conc. | Volume |
| His-tagged hGal-3 | 49.82 µM or can vary batch to batch | 2.525× | 15 nM | 20 µL |
| B-ASF | 25 µM | 2.525× | 15 nM | 20 µL |
| Compounds | 20 mM in 100% DMSO | Various concentration100% DMSO | Various concentration 2% DMSO | 1 µL |
| Anti-His Tb Ab | 5.75 µM | (10×) 10 nM | 1 nM | 5 µL |
| Strep d2 | 16.67 µM | (10×) 200 nM | 20 nM | 5 µL |
| Total Assay volume | | | | 51 µL |

PROTOCOL: The Gal-3 assays were performed in 384 white Opti plates in three replicates at room temperature with gentle shaking at 250-300 rpm From the original stocks, 2.525× working stock concentrations of His-tagged recombinant human Gal-3 (hGal-3) and that of B-ASF were prepared. From the working stock, 20 µL of hGal-3 (15 nM) and 20 µL B-ASF (15 nM) were added to the plates. In Negative Control, only hGal-3 was added. A concentration range of 50× working stocks were prepared for the compounds in 100% DMSO. Aliquots of 1 µL of the compounds were added to the wells and pre-incubated with 20 µL hGal-3 per well for 30 minutes Then 20 µL B-ASF were added and incubated for another 1 hour. To detect the signal, 5 µL (final conc. of 1.0 nM) terbium labelled Anti-His antibody was added and incubated for 30 min followed by adding 5 μL (final conc. of 20 nM) Streptavidin d2 and incubation for another 1 hour. The assay signal was detected using HTRF screen protocol (Excitation wavelength=340 nm, emission wavelength=615 nm/665 nm) on Envision 2104 Multilabel Reader. Data analysed using Toolset and Curve Master. Results are reported in the experimental section ($IC_{50}$ in μM).

Pharmaceutical Composition and Methods of Use

The compounds of this invention inhibit Gal-3. Accordingly, another aspect of the invention is a pharmaceutical composition comprising a therapeutically effective amount of a compound of the present invention, or a pharmaceutically acceptable salt thereof, and a pharmaceutically acceptable carrier.

Another aspect of the invention is a method for treating a patient afflicted with a disease or condition selected from fibrosis of organs (including liver, kidney, lung, heart and skin), liver diseases and conditions (including acute hepatitis, chronic hepatitis, liver fibrosis, liver cirrhosis, portal hypertension, regenerative failure, non-alcoholic steatohepatitis (NASH), liver hypofunction, and hepatic blood flow disorder), cell proliferative diseases, cancers, and conditions (including solid tumor, solid tumor metastasis, vascular fibroma, myeloma, multiple myeloma, Kaposi's sarcoma, leukemia, chronic lymphocytic leukemia (CLL)) and invasive metastasis of cancer cell), inflammatory diseases and conditions (including psoriasis, nephropathy, and pneumonia), gastrointestinal tract diseases and conditions (including irritable bowel syndrome (IBS), inflammatory bowel disease (IBD), and abnormal pancreatic secretion), renal diseases and conditions, urinary tract-associated diseases and conditions (including benign prostatic hyperplasia or symptoms associated with neuropathic bladder disease, spinal cord tumor, hernia of intervertebral disk, spinal canal stenosis, and symptoms derived from diabetes), lower urinary tract diseases and conditions (including obstruction of lower urinary tract), inflammatory diseases and conditions of lower urinary tract (including dysuria and frequent urination), pancreatic diseases and conditions, abnormal angiogenesis-associated diseases and conditions (including arterial obstruction), scleroderma, brain-associated diseases and conditions (including cerebral infarction and cerebral hemorrhage), neuropathic pain and peripheral neuropathy, ocular diseases and conditions (including age-related macular degeneration (AMD), diabetic retinopathy, proliferative vitreoretinopathy (PVR), cicatricial pemphigoid, and glaucoma filtration surgery scarring) with a compound of the present invention.

Another aspect of the invention is a method of treating renal fibrosis, pulmonary fibrosis, hepatic fibrosis, arterial fibrosis and systemic sclerosis comprising administering to a compound of the present invention to a patient.

Another aspect of the invention is a method for treating fibrosis of organs (including liver, kidney, lung, heart and skin) comprising administering to a compound of the present invention to a patient.

Another aspect of the invention is a method for treating liver diseases and conditions (including acute hepatitis, chronic hepatitis, liver fibrosis, liver cirrhosis, portal hypertension, regenerative failure, non-alcoholic steatohepatitis (NASH), liver to hypofunction, and hepatic blood flow disorder) comprising administering to a compound of the present invention to a patient.

Another aspect of the invention is a method for treating cell proliferative diseases, cancers, and conditions (including solid tumor, solid tumor metastasis, vascular fibroma, myeloma, multiple myeloma, Kaposi's sarcoma, leukemia, chronic lymphocytic leukemia (CLL)) and invasive metastasis of cancer cell) comprising administering to a compound of the present invention to a patient.

Another aspect of the invention is a method for treating inflammatory diseases and conditions (including psoriasis, nephropathy, and pneumonia) comprising administering to a compound of the present invention to a patient.

Another aspect of the invention is a method for treating gastrointestinal tract diseases and conditions (including irritable bowel syndrome (IBS), inflammatory bowel disease (IBD), and abnormal pancreatic secretion) comprising administering to a compound of the present invention to a patient.

Another aspect of the invention is a method for treating renal diseases and conditions comprising administering to a compound of the present invention to a patient.

Another aspect of the invention is a method for treating urinary tract-associated diseases and conditions (including benign prostatic hyperplasia or symptoms associated with neuropathic bladder disease, spinal cord tumor, hernia of intervertebral disk, spinal canal stenosis, and symptoms derived from diabetes) comprising administering to a compound of the present invention to a patient.

Another aspect of the invention is a method for treating lower urinary tract diseases and conditions (including obstruction of lower urinary tract), inflammatory diseases and conditions of lower urinary tract (including dysuria and frequent urination) comprising administering to a compound of the present invention to a patient.

Another aspect of the invention is a method for treating pancreatic diseases and conditions comprising administering to a compound of the present invention to a patient.

Another aspect of the invention is a method for treating abnormal angiogenesis-associated diseases and conditions (including arterial obstruction) comprising administering to a compound of the present invention to a patient.

Another aspect of the invention is a method for treating brain-associated diseases and conditions (including cerebral infarction and cerebral hemorrhage) comprising administering to a compound of the present invention to a patient.

Another aspect of the invention is a method for treating neuropathic pain and peripheral neuropathy comprising administering to a compound of the present invention to a patient.

Another aspect of the invention is a method for treating ocular diseases and conditions (including age-related macular degeneration (AMD), diabetic retinopathy, proliferative vitreoretinopathy (PVR), cicatricial pemphigoid, and glaucoma filtration surgery scarring) comprising administering to a compound of the present invention to a patient.

The compounds of the invention may be used in the treatment and/or prophylaxis of conditions in which Gal-3 plays a role.

The compounds of the present invention may be used for the manufacture of a medicament for the treatment and/or prophylaxis of a condition in which inhibition of the physiological activity of Gal-3 is useful, such as diseases in which a Gal-3 receptor participates, is involved in the etiology or pathology of the disease, or is otherwise associated with at least one symptom of the disease.

The compounds of the invention can be used alone, in combination with other compounds of the present invention, or in combination with one or more, preferably one to two other agent(s).

"Therapeutically effective" means the amount of agent required to provide a meaningful patient benefit as understood by practitioners in the field of pain.

"Patient" means a person afflicted with pain and suitable for therapy as understood by practitioners in the field.

"Treatment," "therapy," "regimen," and related terms are used as understood by practitioners in the field.

The compounds of this invention are generally given as pharmaceutical compositions comprised of a therapeutically effective amount of a compound of the present invention or its pharmaceutically acceptable salt and a pharmaceutically acceptable carrier and may contain conventional excipients. A therapeutically effective amount is that which is needed to provide a meaningful patient benefit. Pharmaceutically acceptable carriers are those conventionally known carriers having acceptable safety profiles. Compositions encompass all common solid and liquid forms including capsules, tablets, losenges, and powders as well as liquid suspensions, syrups, elixers, and solutions. Compositions are made using common formulation techniques, and conventional excipients (such as binding and wetting agents) and vehicles (such as water and alcohols) are generally used for compositions. See, for example, *Remington's Pharmaceutical Sciences*, 17th edition, Mack Publishing Company, Easton, PA (1985).

Solid compositions are normally formulated in dosage units and compositions providing from about 1 to 1000 mg of the active ingredient per dose are preferred. Some examples of dosages are 1 mg, 10 mg, 100 mg, 250 mg, 500 mg, and 1000 mg. Generally, other antiretroviral agents will be present in a unit range similar to agents of that class used clinically. Typically, this is 0.25-1000 mg/unit.

Liquid compositions are usually in dosage unit ranges. Generally, the liquid composition will be in a unit dosage range of 1-100 mg/mL. Some examples of dosages are 1 mg/mL, 10 mg/mL, 25 mg/mL, 50 mg/mL, and 100 mg/mL.

The invention encompasses all conventional modes of administration; oral and parenteral methods are preferred. Generally, the dosing regimen will be similar to other agents used clinically. Typically, the daily dose will be 1-100 mg/kg body weight daily. Generally, more compound is required orally and less parenterally. The specific dosing regime, however, will be determined by a physician using sound medical judgement.

Chemical Methods

It will be evident to one skilled in the art that the present disclosure is not limited to the foregoing illustrative examples, and that it can be embodied in other specific forms without departing from the essential attributes thereof. The examples therefore should be considered in all respects as illustrative and not restrictive, reference being made to the appended claims, rather than to the foregoing examples, and all changes which come within the meaning and range of equivalency of the claims are therefore intended to be embraced.

LCMS Conditions:

LCMS analyses were performed on Waters Acquity UPLC system coupled with Waters TUV and SQ mass detector (UV at 200 nm) using the following methods:

Method A: Column: BEH C18 2.1×50 mm; Mobile Phase A: water with 0.05% TFA; Mobile Phase B: acetonitrile with 0.05% TFA; Gradient: 2-98% B over 1.6 minutes; Flow: 0.8 mL/min.

Method B: Column: XBridge BEH XP C18 (2.1×50 mm); 2.5 μm; Mobile phase A: 0.1% TFA in water, Acetonitrile (95:5); Mobile phase B: 0.1% TFA in water, Acetonitrile (5:95); Gradient=0-100% B over 3 minutes; Temperature: 50° C.; Flow rate: 1.1 mL/min.

Method C: Column: XBridge C18 2.1×50 mm, 1.7 μM; Mobile phase A: 5% ACN-95% Water-10 mM ammonium acetate; Mobile phase B: 95% ACN-5% Water-10 mM ammonium acetate; Gradient=0-100 B over 3 minutes; Flow Rate: 1 ml/min. Temperature: 50° C.

HPLC analyses were performed on Shimadzu LC10-AT HPLC system coupled with SPD-10AV UV detector with one of the following methods. All final compounds were determined to be ≥95% pure.

Method A: (Column YMC S5 Combiscreen ODS 4.6×50 mm; Mobile Phase A: 5:95 acetonitrile:water with 0.1% TFA; Mobile Phase B: 95:5 acetonitrile:water with 0.1% TFA; Gradient: 0-100% B over 4 minutes, then a 1-minute hold at 100% B; Flow: 1 mL/min).

Method B: Column Phenomenex Luna 3u C18 4.6×50 mm; Mobile Phase A: 10:90 acetonitrile:water with 0.1% TFA; Mobile Phase B: 90:10 acetonitrile:water with 0.1% TFA; Gradient: 0-100% B over 4 or 8 minutes, then a 1-minute hold at 100% B; Flow: 4 mL/min);

Method C: Column Orthagonal Column Sunfire C18 3.5 um, 3.0×150 mm; Mobile Phase A: 5:95 acetonitrile:water with 0.05% TFA; Mobile Phase B: 95:5 acetonitrile:water with 0.05% TFA; Gradient: 10-100% B over 15 minutes; Flow: 0.5 mL/min).

Preparative HPLC purifications were conducted on Shimadzu LC-8 preparative HPLC system coupled with SPD 20 UV detector. Detailed conditions are described in experimental procedures.

Preparation of Hydrazine Intermediates 1. (5-Chloro-2-(trifluoromethyl)phenyl)hydrazine

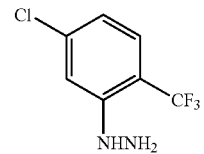 [SMILES: NNc1cc(Cl)ccc1C(F)(F)F]

To a solution of 5-chloro-2-(trifluoromethyl)aniline (6.0 g, 30.7 mmol) in acetic acid (16.1 mL, 281 mmol) at rt was added concentrated HCl (32 mL, 1053 mmol). To the resulting suspension at 0° C. was added a solution of sodium nitrite (2.54 g, 36.8 mmol) in water (9.2 mL) over 10 min. The mixture was stirred at rt for 4 h before a solution of tin(II) chloride dihydrate (15.23 g, 67.5 mmol) in concentrated HCl (32 mL, 1053 mmol) was added over 10 min. The mixture was stirred at rt for 1.5 h. The precipitating solid was collected by suction filtration, then dissolved in water (100 mL), basified with 6N NaOH solution to pH 9, and extracted with EtOAc (4×50 mL). The combined extract was dried over $MgSO_4$ and concentrated to a crude solid. The crude was purified with a silica gel flash column, eluting with 0-5% MeOH in DCM to afford (5-chloro-2-(trifluoromethyl)phenyl)hydrazine (5.35 g, 25.4 mmol, 83% yield) as an off-white solid. MS (ESI) m/z: 210.9/212.9 (M+H)$^+$; $^1$H NMR (400 MHz, METHANOL-d$_4$) δ 7.36-7.44 (m, 2H), 6.79 (br d, J=7.92 Hz, 1H).

2. 5-Chloro-3-hydrazineyl-2-(trifluoromethyl)pyridine hydrochloride

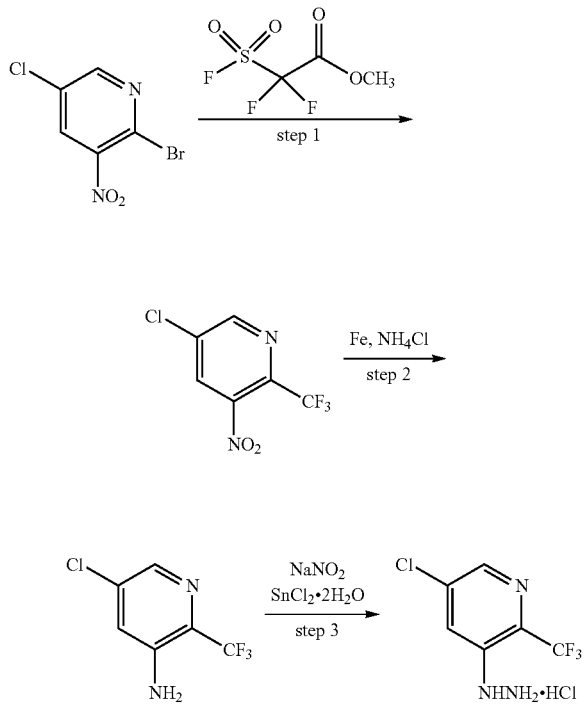

Step 1. 5-Chloro-3-nitro-2-(trifluoromethyl)pyridine

A mixture of 2-bromo-5-chloro-3-nitropyridine (1.00 g, 4.21 mmol), methyl 2,2-difluoro-2-(fluorosulfonyl)acetate (0.971 g, 5.05 mmol), and copper(I) iodide (0.963 g, 5.05 mmol) in DMF (10 mL) was heated at 85° C. for 16 h. Upon cooling to rt, the mixture was diluted with ethyl acetate (20 mL) and filtered through Celite. The filtrate was concentrated under vacuum to almost dryness. The residue was diluted with ethyl acetate (180 mL), washed with water (3×40 mL) and brine (30 mL), and dried over anhydrous MgSO$_4$. The desired product, 5-chloro-3-nitro-2-(trifluoromethyl)pyridine (0.578 g, 2.55 mmol, 60.6% yield), was isolated as a light yellow oil by flash chromatograph (80 g silica gel, solid loading, 5-20% ethyl acetate/hexane). $^1$H NMR (500 MHz, chloroform-d) δ 8.89 (d, J=2.2 Hz, 1H), 8.25 (d, J=1.7 Hz, 1H).

Step 2. 5-Chloro-2-(trifluoromethyl)pyridin-3-amine

A mixture of 5-chloro-3-nitro-2-(trifluoromethyl)pyridine (0.578 g, 2.55 mmol), ammonium chloride (0.682 g, 12.76 mmol), and iron mesh (0.570 g, 10.21 mmol) in ethanol (15 mL) and water (1.5 mL) was heated at 80° C. for 15 h. Upon cooling to rt, the mixture was diluted with THF (15 mL) and filtered through Celite. The filtrate was concentrated under vacuum to dryness. To the residue was added water (15 mL) and saturated NaHCO$_3$ solution (3 mL). The mixture was extracted with dichloromethane (4×40 mL). The combined extract was dried over anhydrous Na$_2$SO$_4$ and concentrated under vacuum. The residue was subjected to flash chromatograph (40 g silica gel, solid loading, 10-20% ethyl acetate/hexane) to provide 5-chloro-2-(trifluoromethyl)pyridin-3-amine (0.371 g, 1.887 mmol, 74.0% yield) as a white solid. MS (ESI) m/z: 196.9 [M+H]$^+$.

Step 3. 5-Chloro-3-hydrazineyl-2-(trifluoromethyl)pyridine hydrochloride

To a solution of 5-chloro-2-(trifluoromethyl)pyridin-3-amine (0.300 g, 1.526 mmol) in acetic acid (0.8 mL, 13.97 mmol) at rt was added concentrated hydrochloric acid (1.6 mL, 52.7 mmol). To the resulting mixture at −5 to 0° C. was added a solution of sodium nitrite (0.126 g, 1.832 mmol) in water (0.5 mL) over 5 min. The mixture was stirred at −5 to 5° C. for 45 min before a solution of tin(II) chloride dihydrate (0.758 g, 3.36 mmol) in concentrated hydrochloric acid (1.6 mL, 52.7 mmol), pre-cooled at 0° C., over 10 min. The mixture was stirred at −5 to 5° C. for 2 h. To the mixture was added methanol (5 mL), and the insoluble inorganic salt was removed by suction filtration. The filtrate was concentrated under vacuum to a volume of approximately 12 mL. The residue was subjected to prep. HPLC (Column: Sunfire C18 OBD 5u 30×100 mm; Solvent A: 90% H$_2$O-10% methanol-0.1% TFA, Solvent B: 10% methanol-90% H$_2$O 0.1% TFA; Gradient: 0-100% B over 10 min; Flow rate: 40 ml/min) with multiple injections. The correct fractions were combined and concentrated under vacuum to a volume of approximately 20 mL. To the residue was added concentrated hydrochloric acid (5 mL). The mixture was cooled to −78° C. and lyophilized to provide 5-chloro-3-hydrazineyl-2-(trifluoromethyl)pyridine, HCl (50 mg, 0.202 mmol, 13.2% yield) as a beige solid.

3. (5-Chloro-2-(trifluoromethoxy)phenyl)hydrazine hydrochloride

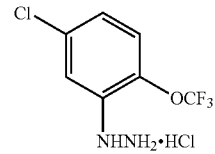

To a solution of 5-chloro-2-(trifluoromethoxy)aniline (1.269 g, 6.0 mmol) in acetic acid (3.0 mL, 52.4 mmol) at rt was added concentrated hydrochloric acid (6.0 mL, 197 mmol) in one portion. To the resulting mixture at −10 to −5° C. was added a solution of sodium nitrite (0.497 g, 7.20 mmol) in water (1.8 mL) over 10 min. The mixture was stirred at −5 to 0° C. for 45 min before a solution of tin(II) chloride dihydrate (2.98 g, 13.20 mmol) in concentrated hydrochloric acid (6.0 mL, 197 mmol), pre-cooled at 0° C., was added over 10 min. The mixture was stirred at −10 to 0° C. for 2 h. The precipitating product, (5-chloro-2-(trifluoromethoxy)phenyl)hydrazine, HCl (2 g, 6.0 mmol, 100% yield), was collected as a pale solid by suction filtration and dried at 50° C. under vacuum. MS (ESI) m/z: 226.9 [M+H]$^+$; $^1$H NMR (400 MHz, methanol-d$_4$) δ 7.36 (dq, J=8.8, 1.7 Hz, 1H), 7.19-7.16 (m, 1H), 7.13 (dd, J=8.7, 2.4 Hz, 1H).

4. 6-Hydrazineylbenzo[d]thiazole dihydrochloride

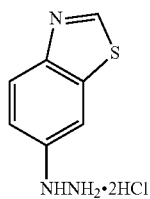

To a solution of benzo[d]thiazol-6-amine (0.901 g, 6.0 mmol) in acetic acid (3.0 mL, 52.4 mmol) at rt was added concentrated hydrochloric acid (6.0 mL, 197 mmol) in one portion. To the resulting mixture at −10 to −5° C. was added a solution of sodium nitrite (0.497 g, 7.20 mmol) in water (1.8 mL) over 10 min. The mixture was stirred at −5 to 0° C. for 45 min before a solution of tin(II) chloride dihydrate (2.98 g, 13.20 mmol) in concentrated hydrochloric acid (6.0 mL, 197 mmol), pre-cooled at 0° C., was added over 10 min. The mixture was stirred at −10 to 0° C. for 2 h. The precipitating product, 6-hydrazineylbenzo[d]thiazole, 2 HCl (1.68 g, 6.0 mmol, 100% yield, 85% pure), was collected as a pale solid by suction filtration and dried under vacuum. MS (ESI) m/z: 165.9 [M+H]$^+$; $^1$H NMR (400 MHz, methanol-$d_4$) δ 9.19 (s, 1H), 8.04 (d, J=8.8 Hz, 1H), 7.65 (d, J=2.3 Hz, 1H), 7.25 (dd, J=8.9, 2.4 Hz, 1H).

5. 5-Chloro-2-cyclopropylphenyl)hydrazine hydrochloride

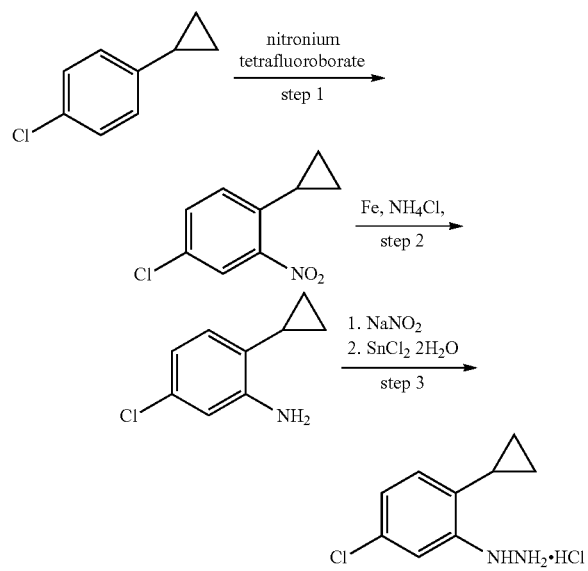

Step 1. 4-Chloro-1-cyclopropyl-2-nitrobenzene

To a solution of 1-chloro-4-cyclopropylbenzene (1.0 g, 6.55 mmol) in acetonitrile (1.5 mL) at 0° C. was added nitronium tetrafluoroborate (14.41 mL, 7.21 mmol, 0.5 M solution in sulfolane). The reaction mixture was stirred at rt for 0.5 h. Aqueous saturated NaHCO$_3$ solution (40 mL) and water (20 mL) were added. The resulting mixture was extracted with EtOAc (2×125 mL). The combined organic layers were dried over MgSO$_4$, filtered and concentrated to give a crude product, which was subjected to flash chromatography (80 g silica gel, 0-20% ethyl acetate/hexane) to afford 4-chloro-1-cyclopropyl-2-nitrobenzene (350 mg, 1.771 mmol, 27.0% yield) as yellow oil. $^1$H NMR (400 MHz, chloroform-d) δ 7.84 (d, J=2.2 Hz, 1H), 7.47 (dd, J=8.4, 2.2 Hz, 1H), 7.13 (d, J=8.3 Hz, 1H), 2.37 (tt, J=8.6, 5.4 Hz, 1H), 1.15-1.05 (m, 2H), 0.77-0.65 (m, 2H).

Step 2. 5-Chloro-2-cyclopropylaniline

A mixture of 4-chloro-1-cyclopropyl-2-nitrobenzene (0.33 g, 1.670 mmol), ammonium chloride (0.447 g, 8.35 mmol) and iron mesh (0.373 g, 6.68 mmol) in ethanol (7.6 mL) and water (0.76 mL) was heated at 80° C. for 5 h. Additional iron mesh (200 mg), water (0.1 mL) and ammonium chloride (300 mg) were added. The reaction mixture was heated at 80° C. for another 5 h. Upon cooling to rt, the solvent was removed under vacuum. The residue was diluted with CH$_2$Cl$_2$ (20 mL), water (10 mL) and filtered through Celite. The organic layer of the filtrate was separated and concentrated under vacuum to dryness. The residue was subjected to flash chromatography (24 g silica gel, 0-35% ethyl acetate/hexane) to afford 5-chloro-2-cyclopropylaniline (280 mg, 99% yield) as a white solid. MS (ESI) m/z: 168.0 [M+H]$^+$; $^1$H NMR (500 MHz, chloroform-d) δ 6.96 (dt, J=7.4, 1.1 Hz, 1H), 6.69-6.60 (m, 2H), 1.60-1.68 (m, 1H), 0.97-0.88 (m, 2H), 0.63-0.44 (m, 2H).

Step 3. 5-Chloro-2-cyclopropylphenyl)hydrazine hydrochloride

To a solution of 5-chloro-2-cyclopropylaniline (0.312 g, 1.861 mmol) in acetic acid (0.94 mL, 16.4 mmol) at rt was added concentrated hydrochloric acid (1.8 mL, 59.2 mmol) in one portion. To the resulting mixture at −10 to −5° C. was added a solution of sodium nitrite (0.154 g, 2.23 mmol) in water (0.55 mL) over 10 min. The mixture was stirred at −5 to 0° C. for 45 min before a solution of tin(II) chloride dihydrate (0.776 g, 4.09 mmol) in concentrated hydrochloric acid (1.8 mL, 59.2 mmol), pre-cooled at 0° C., was added over 10 min. The mixture was stirred at −10 to 5° C. for 2 h. The precipitating product, 5-chloro-2-cyclopropylphenyl) hydrazine, HCl (465 mg, 114% yield), was collected as a pale solid by suction filtration and dried under vacuum. MS (ESI) m/z: 183.2 [M+H]$^+$.

Example 1

(2S,3R,4R,5R,6R)-2-(1-(Benzo[d]thiazol-6-yl)-3-methyl-1H-1,2,4-triazol-5-yl)-4-(4-(4-bromo-2,3-difluorophenyl)-1H-1,2,3-triazol-1-yl)-6-(hydroxymethyl)tetrahydro-2H-pyran-3,5-diol

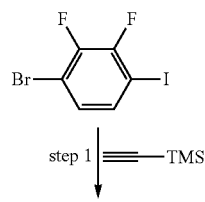

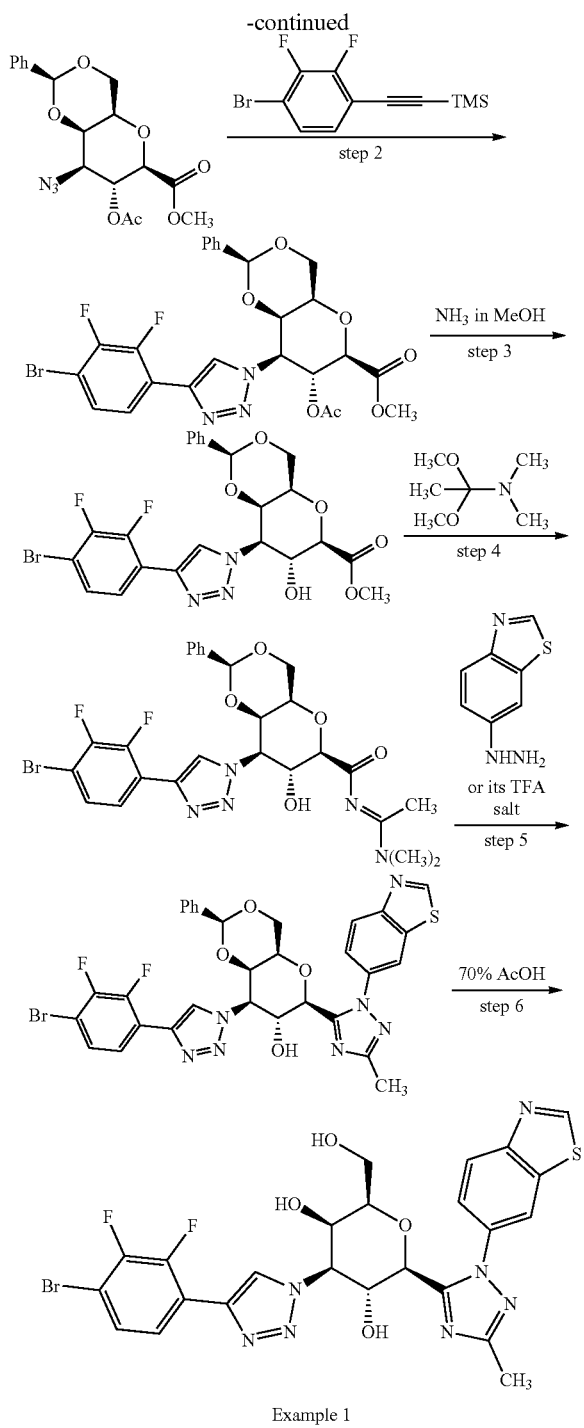

Example 1

Step 1. ((4-Bromo-2,3-difluorophenyl)ethynyl)trimethylsilane

To a degassed mixture of 1-bromo-2,3-difluoro-4-iodobenzene (0.512 g, 1.606 mmol), copper(I) iodide (0.007 g, 0.037 mmol), and bis(triphenylphosphine)palladium(II) chloride (0.023 g, 0.032 mmol) in TEA (3 ml) at rt was added ethynyltrimethylsilane (0.238 ml, 1.69 mmol) over 20 min. A slightly exothermic reaction was observed. The mixture was heated in a sealed tube at 65° C. for 3 h, then diluted with hexanes (10 ml) and filtered through Celite. The filtrate was concentrated in vacuo, and the residue was purified with a silica gel flash column, eluting with hexane to afford ((4-bromo-2,3-difluorophenyl)ethynyl)trimethylsilane (425 mg, 1.470 mmol, 92% yield) as an oil. $^1$H NMR (400 MHz, chloroform-d) δ 7.20-7.24 (m, 1H), 7.03-7.13 (m, 1H), 0.24-0.29 (m, 9H).

Step 2. Methyl (2S,4aR,6R,7R,8S,8aR)-7-acetoxy-8-(4-(4-bromo-2,3-difluorophenyl)-1H-1,2,3-triazol-1-yl)-2-phenylhexahydropyrano[3,2-d][1,3]dioxine-6-carboxylate To a solution of methyl (4aR,6R,7R,8S,8aR)-7-acetoxy-8-azido-2-phenylhexahydropyrano[3,2-d][1,3]dioxine-6-carboxylate (0.425 g, 1.126 mmol) in DMF (3.85 mL) and H$_2$O (1.54 mL) were added (+)-sodium L-ascorbate (0.223 g, 1.13 mmol), copper(II) sulfate pentahydrate (0.253 g, 1.01 mmol), and ((4-bromo-2,3-difluorophenyl)ethynyl)trimethylsilane (0.425 g, 1.470 mmol). The reaction mixture was heated at 85° C. for 1 h. Upon cooling to room temperature, the mixture was mixed with ice cold water (12 mL). The resulting mixture was stirred at rt for 10 min. The brown solid was collected by suction filtration. The solid was mixed with a mixture of CHCl$_3$ (40 mL) and MeOH (4 mL). The resulting mixture was heated to reflux, stirred for 10 min and subjected to filtration when it was hot. The solid residue was washed with CHCl$_3$ (8 mL). The organic layers were combined and concentrated under vacuum to dryness. The residue was suspended into MeOH (15 mL), stirred at rt for 5 min, and subjected to filtration. The filter cake was collected and dried under vacuum at 50° C. overnight to give methyl (2S,4aR,6R,7R,8S,8aR)-7-acetoxy-8-(4-(4-bromo-2,3-difluorophenyl)-1H-1,2,3-triazol-1-yl)-2-phenylhexahydropyrano-[3,2-d][1,3]dioxine-6-carboxylate (0.668 g, 100% yield). MS (ESI) m/z: 594.2 [M+H]$^+$; $^1$H NMR (400 MHz, chloroform-d) δ 8.30 (d, J=3.4 Hz, 1H), 7.90 (ddd, J=8.8, 6.7, 2.1 Hz, 1H), 7.59-7.33 (m, 6H), 5.88 (dd, J=11.0, 9.6 Hz, 1H), 5.54 (s, 1H), 5.22 (dd, J=11.0, 3.3 Hz, 1H), 4.58-4.37 (m, 2H), 4.22 (d, J=9.6 Hz, 1H), 4.12 (dd, J=12.8, 1.8 Hz, 1H), 3.77-3.83 (m, 4H), 1.86 (s, 3H).

Step 3. (2S,4aR,6R,7R,8R,8aR)-8-(4-(4-Bromo-2,3-difluorophenyl)-1H-1,2,3-triazol-1-yl)-7-hydroxy-2-phenylhexahydropyrano[3,2-d][1,3]dioxine-6-carboxamide Ammonia in methanol (7 N) (700 mL, 490 mmol), pre-cooled in refrigerator, was added to methyl (2S,4aR,6R,7R,8S,8aR)-7-acetoxy-8-(4-(4-bromo-2,3-difluorophenyl)-1H-1,2,3-triazol-1-yl)-2-phenylhexahydropyrano[3,2-d][1,3]dioxine-6-carboxylate (0.668 g, 1.13 mmol) in one portion. The mixture was stirred at room temperature in a sealed flask for 18 h. The mixture (now clear solution) was concentrated under vacuum to give (2S,4aR,6R,7R,8R,8aR)-8-(4-(4-bromo-2,3-difluorophenyl)-1H-1,2,3-triazol-1-yl)-7-hydroxy-2-phenylhexahydropyrano[3,2-d][1,3]dioxine-6-carboxamide (0.604 g, 100% yield) as a white solid: MS (ESI) m/z: 537.2 [M+H]$^+$.

Step 4. (2S,4aR,6R,7R,8R,8aR)-8-(4-(4-Bromo-2,3-difluorophenyl)-1H-1,2,3-triazol-1-yl)-N-((E)-1-(dimethylamino)ethylidene)-7-hydroxy-2-phenylhexahydropyrano[3,2-d][1,3]dioxine-6-carboxamide A heterogeneous mixture of (2S,4aR,6R,7R,8R,8aR)-8-(4-(4-bromo-2,3-difluorophenyl)-1H-1,2,3-triazol-1-yl)-7-hydroxy-2-phenylhexahydropyrano[3,2-d][1,3]dioxine-6- carboxamide (0.604 g, 1.13 mmol) and 1,1-dimethoxy-N,N-dimethylethan-1-amine (0.777 g, 5.83 mmol) in 1,4-dioxane (16 mL) was heated at 60° C. for 4.5 h. The volatiles were removed under vacuum to give (2S,4aR,6R,7R,8R,8aR)-8-(4-(4-bromo-2,3-difluorophenyl)-1H-1,2,3-triazol-1-yl)-N-((E)-1-(dimethylamino)ethylidene)-7-hydroxy-2-phenylhexahydropyrano[3,2-d][1,3]dioxine-6-carboxamide (0.737 g, 99% yield) as a beige solid. MS (ESI) m/z: 605.9 [M+H]+.

Step 5. (2S,4aR,6S,7R,8R,8aR)-6-(1-(Benzo[d]thiazol-6-yl)-3-methyl-1H-1,2,4-triazol-5-yl)-8-(4-(4-bromo-2,3-difluorophenyl)-1H-1,2,3-triazol-1-yl)-2-phenylhexahydropyrano[3,2-d][1,3]dioxin-7-ol A mixture of (2S,4aR,6R,7R,8R,8aR)-8-(4-(4-bromo-2,3-difluorophenyl)-1H-1,2,3-triazol-1-yl)-N-((E)-1-(dimethylamino)ethylidene)-7-hydroxy-2-phenylhexahydropyrano[3,2-d][1,3]dioxine-6-carboxamide (90 mg, 0.137 mmol) and 6-hydrazineylbenzo[d]thiazole, TFA (40 mg, 0.142 mmol) in dioxane (0.5 mL) and acetic acid (0.5 mL) was stirred at 50° C. for 60 min. The mixture was concentrated under vacuum to almost dryness. This crude product was dissolved in CH$_2$Cl$_2$ (10 mL) and 2 g silica gel was added. The solvent was evaporate under vacuum. The solid residue was loaded into a solid loading cartridge and purified by ISCO automated chromatography (12 g silica gel, 0-3% MeOH/CH$_2$Cl$_2$ in 12 min gradient) to give (2S,4aR,6S,7R,8R,8aR)-6-(1-(benzo[d]thiazol-6-yl)-3-methyl-1H-1,2,4-triazol-5-yl)-8-(4-(4-bromo-2,3-difluorophenyl)-1H-1,2,3-triazol-1-yl)-2-phenylhexahydropyrano[3,2-d][1,3]dioxin-7-ol (60 mg, 62% yield) as a white solid. MS (ESI) m/z: 708.3 [M+H]+; 1H NMR (400 MHz, chloroform-d) δ 9.13 (s, 1H), 8.35 (d, J=3.5 Hz, 1H), 8.21-8.26 (m, 2H), 7.94 (ddd, J=8.8, 6.8, 2.1 Hz, 1H), 7.74 (dd, J=8.8, 2.1 Hz, 1H), 7.31-7.47 (m, 6H), 5.49 (s, 1H), 5.07-5.20 (m, 2H), 4.67-4.53 (m, 1H), 4.54-4.42 (m, 1H), 4.14 (dd, J=12.6, 1.6 Hz, 1H), 4.04 (dd, J=12.6, 1.8 Hz, 1H), 3.89 (s, 1H), 3.67-3.70 (m, 1H), 2.46 (s, 3H).

Step 6. (2S,3R,4R,5R,6R)-2-(1-(Benzo[d]thiazol-6-yl)-3-methyl-1H-1,2,4-triazol-5-yl)-4-(4-(4-bromo-2,3-difluorophenyl)-1H-1,2,3-triazol-1-yl)-6-(hydroxymethyl)tetrahydro-2H-pyran-3,5-diol A suspension of (4aR,6S,7R,8R,8aR)-6-(1-(benzo[d]thiazol-6-yl)-3-methyl-1H-1,2,4-triazol-5-yl)-8-(4-(4-bromo-2,3-difluorophenyl)-1H-1,2,3-triazol-1-yl)-2-phenylhexahydropyrano[3,2-d][1,3]dioxin-7-ol (60 mg, 0.021 mmol) in 70% acetic acid (5 mL) was heated at 70° C. for 15 h. The resulting solution was subjected to prep. HPLC (Column: Sunfire Prep C18 OBD 5u 30×100 mm (10 min); Solvent A: 10% ACN-90% H$_2$O-0.1% TFA, Solvent B: 90% ACN-10% H$_2$O-0.1% TFA; Gradient: 20-100% B over 10 min; Flow rate: 20 ml/min). The correct fractions were combined, concentrated under vacuum, basified with saturated NaHCO$_3$ solution to pH 9-10, and extracted with CHCl$_3$ (2×30 mL). The combined extract was dried over anhydrous Na$_2$SO$_4$. Removal of the solvent under vacuum provided the (2S,3R,4R,5R,6R)-2-(1-(benzo[d]thiazol-6-yl)-3-methyl-1H-1,2,4-triazol-5-yl)-4-(4-(4-bromo-2,3-difluorophenyl)-1H-1,2,3-triazol-1-yl)-6-(hydroxymethyl)tetrahydro-2H-pyran-3,5-diol (14.7 mg, 27.4% yield) as a white solid. MS (ESI) m/z: 619.7 [M+H]+; 1H NMR (400 MHz, Methanol-d4) δ 9.30 (s, 1H), 8.43 (d, J=2.1 Hz, 1H), 8.38 (d, J=3.4 Hz, 1H), 8.15 (d, J=8.7 Hz, 1H), 7.81-7.72 (m, 2H), 7.43 (ddd, J=8.5, 6.2, 2.0 Hz, 1H), 4.96-4.82 (m, 2H), 4.53-4.44 (m, 1H), 4.05 (dd, J=2.5, 1.0 Hz, 1H), 3.86-3.68 (m, 2H), 3.63 (dd, J=11.4, 4.0 Hz, 1H), 2.38 (s, 3H). hGal-3 IC$_{50}$=0.007 µM.

Example 2

(2R,3R,4S,5R,6S)-6-(1-(Benzo[d]thiazol-6-yl)-3-methyl-1H-1,2,4-triazol-5-yl)-4-(4-(4-bromo-2,3-difluorophenyl)-1H-1,2,3-triazol-1-yl)-2-(hydroxymethyl)-5-methoxytetrahydro-2H-pyran-3-ol

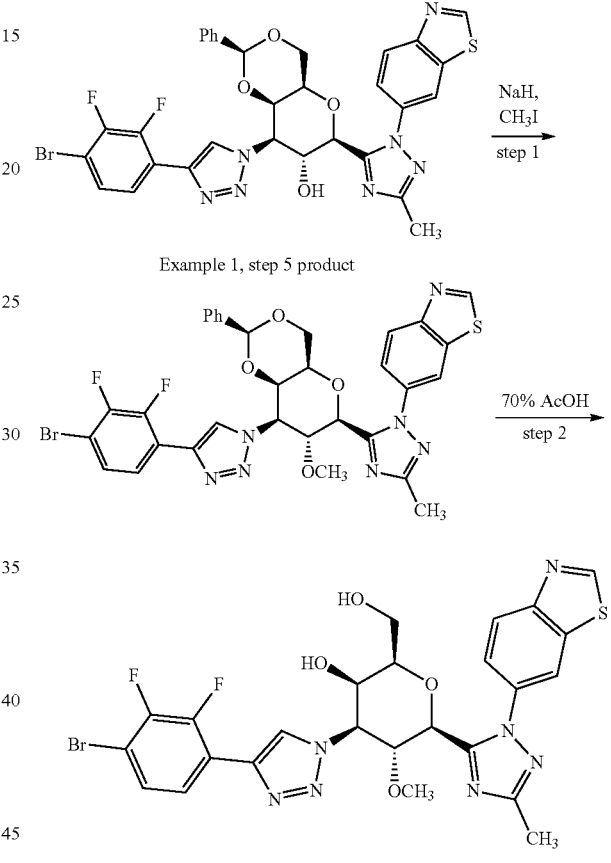

Example 2

Step 1. 6-(5-((2S,4aR,6S,7R,8R,8aR)-8-(4-(4-Bromo-2,3-difluorophenyl)-1H-1,2,3-triazol-1-yl)-7-methoxy-2-phenylhexahydropyrano[3,2-d][1,3]dioxin-6-yl)-3-methyl-1H-1,2,4-triazol-1-yl)benzo[d]thiazole A mixture of (4aR,6S,7R,8R,8aR)-6-(1-(benzo[d]thiazol-6-yl)-3-methyl-1H-1,2,4-triazol-5-yl)-8-(4-(4-bromo-2,3-difluorophenyl)-1H-1,2,3-triazol-1-yl)-2-phenylhexahydropyrano[3,2-d][1,3]dioxin-7-ol (39 mg, 0.055 mmol) in THF (1.6 ml) at rt was added NaH (60% in mineral oil) (6.60 mg, 0.165 mmol). The mixture was stirred at for 5 min before MeI (17 µl, 0.275 mmol) was added. The reaction mixture was stirred at rt for 60 min and then quenched with saturated NH$_4$Cl solution. The volatiles were removed and the residue was purified ISCO automated chromatography (12 g silica gel, 0-100% Heaxane/EtOAc in 12 min gradient) to give 6-(5-((4aR,6S,7R,8R,8aR)-8-(4-(4-bromo-2,3-difluorophenyl)-1H-1,2,3-triazol-1-yl)-7-methoxy-2-phenylhexahydropyrano[3,2-d][1,3]dioxin-6-yl)-3-methyl-1H-1,2,4-triazol-1-yl)benzo[d]thiazole (39 mg, 0.025 mmol, 98% yield) as a beige solid. MS (ESI) m/z: 721.5 [M+H]+; 1H NMR (400 MHz, chloroform-d) δ 9.13 (s, 1H), 8.41 (d, J=3.6 Hz, 1H), 8.26-8.16 (m, 2H), 7.97 (ddd, J=8.8, 6.8, 2.1 Hz, 1H), 7.74 (dd, J=8.7, 2.1 Hz, 1H), 7.55-7.46 (m, 2H), 7.46-7.38 (m, 4H), 5.57 (s, 1H), 5.09 (dd, J=10.3, 3.3 Hz, 1H), 4.68 (dd, J=10.3, 9.2 Hz, 1H), 4.59 (d, J=9.3 Hz, 1H), 4.53-4.35 (m, 2H), 4.09-4.12 (m, 1H), 3.69-3.75 (m, 1H), 2.91 (s, 3H), 2.50 (s, 3H).

Step 2. (2R,3R,4S,5R,6S)-6-(1-(Benzo[d]thiazol-6-yl)-3-methyl-1H-1,2,4-triazol-5-yl)-4-(4-(4-bromo-2,3-difluorophenyl)-1H-1,2,3-triazol-1-yl)-2-(hydroxymethyl)-5-methoxytetrahydro-2H-pyran-3-ol A suspension of 6-(5-((4aR,6S,7R,8R,8aR)-8-(4-(4-bromo-2,3-difluorophenyl)-1H-1,2,3-triazol-1-yl)-7-methoxy-2-phenylhexahydropyrano[3,2-d][1,3]dioxin-6-yl)-3-methyl-1H-1,2,4-triazol-1-yl)benzo[d]thiazole (39 mg, 0.054 mmol) in 70% acetic acid (3 mL) was heated at 70° C. for 15 h. The reaction mixture was diluted with methanol and subjected to prep. HPLC (Phenomenex Luna AXIA 5u C18 30.0×100 (10 min); Solvent A: 10% ACN-90% H2O-0.1% TFA, Solvent B: 90% ACN-10% H2O-0.1% TFA; Gradient: 20-100% B over 10 min; Flow rate: 20 ml/min). The correct fractions were combined, concentrated under vacuum, basified with satu. NaHCO3 solution to pH 9-10, and extracted with CHCl3 (2×30 mL). The combined extract was dried over anhydrous Na2SO4. Removal of the solvent under vacuum provided the (2R,3R,4S,5R,6S)-6-(1-(benzo[d]thiazol-6-yl)-3-methyl-1H-1,2,4-triazol-5-yl)-4-(4-(4-bromo-2,3-difluorophenyl)-1H-1,2,3-triazol-1-yl)-2-(hydroxymethyl)-5-methoxytetrahydro-2H-pyran-3-ol (16.4 mg, 0.025 mmol, 46.9% yield) as beige soild. MS (ESI) m/z: 634.0 [M+H]+; 1H NMR (400 MHz, methanol-d4) δ 9.42 (s, 1H), 8.63 (d, J=3.4 Hz, 1H), 8.53 (d, J=2.2 Hz, 1H), 8.28 (d, J=8.7 Hz, 1H), 7.96-7.83 (m, 2H), 7.55 (ddd, J=8.5, 6.2, 2.0 Hz, 1H), 5.05 (dd, J=10.5, 3.0 Hz, 1H), 4.76 (dd, J=10.5, 9.4 Hz, 1H), 4.61 (d, J=9.3 Hz, 1H), 4.14 (d, J=2.9 Hz, 1H), 3.94-3.83 (m, 2H), 3.80-3.71 (m, 1H), 2.95 (s, 3H), 2.50 (s, 3H). hGal-3 IC50=0.013 µM.

Example 3

(2S,3R,4R,5R,6R)-2-(1-(5-Chloro-2-(trifluoromethyl)phenyl)-3-methyl-1H-1,2,4-triazol-5-yl)-4-(4-(4-chloro-3-fluoro-5-methoxyphenyl)-1H-1,2,3-triazol-1-yl)-6-(hydroxymethyl)tetrahydro-2H-pyran-3,5-diol

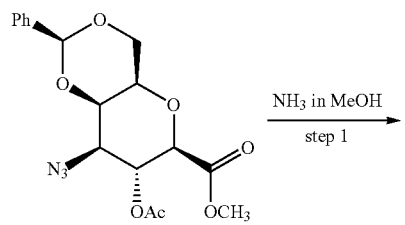

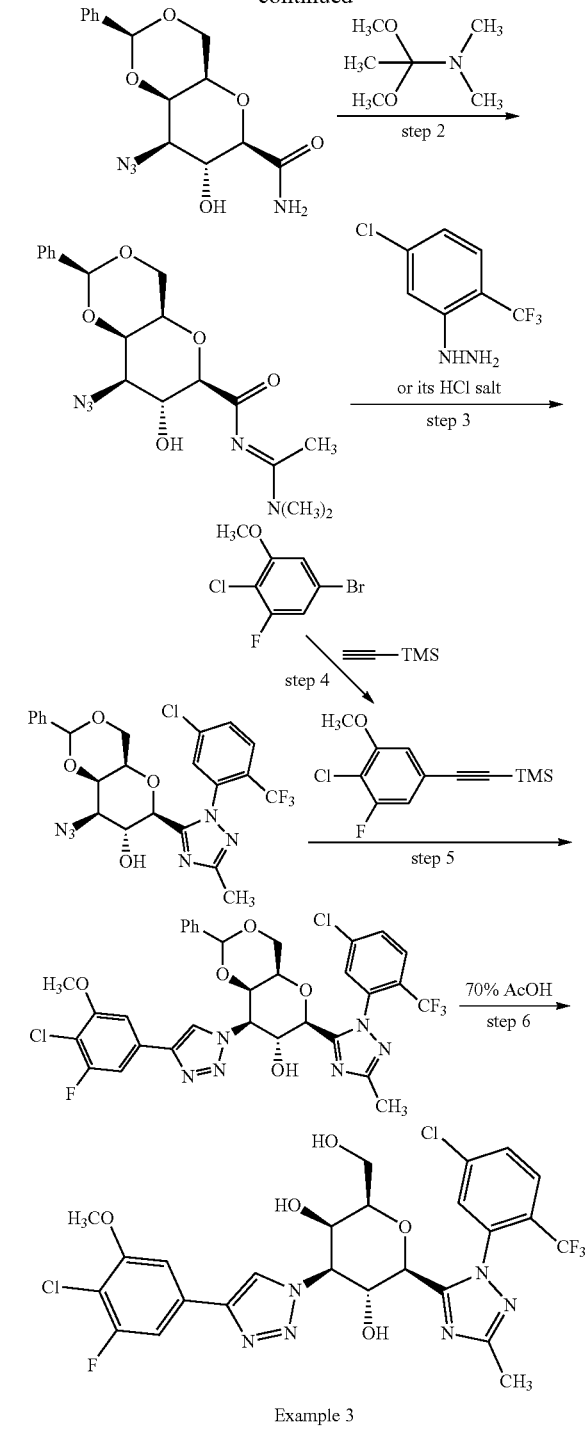

Example 3

Step 1. (4aR,6R,7R,8R,8aR)-8-Azido-7-hydroxy-2-phenylhexahydropyrano[3,2-d][1,3]dioxine-6-carboxamide A solution of methyl (4aR,6R,7R,8S,8aR)-7-acetoxy-8-azido-2-phenylhexahydropyrano[3,2-d][1,3]dioxine-6-carboxylate (592 mg, 1.569 mmol) in 7M ammonia in MeOH (20 ml, 140 mmol) was stirred at rt overnight. The reaction was concentrated under vacuum to afford (4aR,6R,7R,8R,8aR)-8-azido-7-hydroxy-2-phenylhexahydropyrano[3,2-d]

[1,3]dioxine-6-carboxamide (482 mg, 1.505 mmol, 96% yield) as a tan solid. MS (ESI) m/z: 321.0 [M+H]+; 1H NMR (400 MHz, methanol-d4) δ 7.47-7.56 (m, 2H), 7.32-7.41 (m, 3H), 5.68 (s, 1H), 4.37 (d, J=3.30 Hz, 1H), 4.27 (dd, J=1.54, 12.54 Hz, 1H), 4.14-4.21 (m, 1H), 4.06 (t, J=9.79 Hz, 1H), 3.80 (d, J=9.46 Hz, 1H), 3.64 (s, 1H), 3.45 (dd, J=3.41, 10.01 Hz, 1H).

Step 2. (4aR,6R,7R,8R,8aR)-8-Azido-N-((E)-1-(dimethylamino)ethylidene)-7-hydroxy-2-phenyl-hexahydropyrano[3,2-d][1,3]dioxine-6-carboxamide To a solution of (4aR,6R,7R,8R,8aR)-8-azido-7-hydroxy-2-phenylhexahydropyrano[3,2-d][1,3]dioxine-6-carboxamide (395 mg, 1.233 mmol) in dioxane (4111 μl) at rt was added 1,1-dimethoxy-N,N-dimethylethan-1-amine (493 mg, 3.70 mmol). The mixture was stirred at 80° C. for 2 h and then concentrated in vacuo to dryness. The residue was triturated with diethyl ether to give (4aR,6R,7R,8R,8aR)-8-azido-N-((E)-1-(dimethylamino)ethylidene)-7-hydroxy-2-phenylhexahydropyrano[3,2-d][1,3]dioxine-6-carboxamide (480 mg, 1.233 mmol, 100% yield) as an oil. MS (ESI) m/z: 390.1 [M+H]+.

Step 3. (4aR,6S,7R,8R,8aR)-8-Azido-6-(1-(5-chloro-2-(trifluoromethyl)phenyl)-3-methyl-1H-1,2,4-triazol-5-yl)-2-phenylhexahydropyrano[3,2-d][1,3]dioxin-7-ol To (4aR,6R,7R,8R,8aR)-8-azido-N-((E)-1-(dimethylamino)ethylidene)-7-hydroxy-2-phenylhexahydropyrano[3,2-d][1,3]dioxine-6-carboxamide (600 mg, 1.448 mmol) in acetic acid (7 mL) and dioxane (7 mL) was added (5-chloro-2-(trifluoromethyl)phenyl)hydrazine (335 mg, 1.593 mmol). The resulting mixture was stirred at 80° C. for 1 h and then concentrated under vacuum. The residue was purified by ISCO automated chromatography (80 g silica gel, 0-65% ethyl acetate/hexanes) to afford (4aR,6S,7R,8R,8aR)-8-azido-6-(1-(5-chloro-2-(trifluoromethyl)phenyl)-3-methyl-1H-1,2,4-triazol-5-yl)-2-phenylhexahydropyrano[3,2-d][1,3]dioxin-7-ol (639 mg, 0.833 mmol, 57.5% yield) as a tan solid. MS (ESI) m/z: 537.2 [M+H]+.

Step 4. ((4-Chloro-3-fluoro-5-methoxyphenyl)ethynyl)trimethylsilane

To a degassed mixture of 5-bromo-2-chloro-1-fluoro-3-methoxybenzene (0.25 g, 1.044 mmol), copper(I) iodide (3.38 mg, 0.018 mmol), and bis(triphenylphosphine)palladium(II) chloride (0.015 g, 0.021 mmol) in TEA (1.740 ml) was added ethynyltrimethylsilane (0.155 ml, 1.096 mmol) over 5 min. The mixture was stirred at rt overnight and then concentrated under vacuum. The residue was purified by ISCO automated chromatography (40 g silica gel, 0-20% ethyl acetate/hexanes) to afford ((4-chloro-3-fluoro-5-methoxyphenyl)ethynyl)trimethylsilane (251 mg, 0.978 mmol, 94% yield) as an off-white solid. 1H NMR (400 MHz, chloroform-d) δ 6.91 (dd, J=1.65, 8.91 Hz, 1H), 6.81 (t, J=1.43 Hz, 1H), 3.92 (s, 3H), 0.25-0.28 (m, 9H).

Step 5. (4aR,6S,7R,8R,8aR)-6-(1-(5-Chloro-2-(trifluoromethyl)phenyl)-3-methyl-1H-1,2,4-triazol-5-yl)-8-(4-(4-chloro-3-fluoro-5-methoxyphenyl)-1H-1,2,3-triazol-1-yl)-2-phenylhexahydropyrano[3,2-d][1,3]dioxin-7-ol To (4aR,6S,7R,8R,8aR)-8-azido-6-(1-(5-chloro-2-(trifluoromethyl)phenyl)-3-methyl-1H-1,2,4-triazol-5-yl)-2-phenylhexahydropyrano[3,2-d][1,3]dioxin-7-ol (38 mg, 0.052 mmol) in dioxane (1076 μl) and water (215 μl) were added (+)-sodium L-ascorbate (10.24 mg, 0.052 mmol), copper(II) sulfate pentahydrate (11.61 mg, 0.047 mmol), and ((4-chloro-3-fluoro-5-methoxyphenyl)ethynyl)trimethylsilane (23.88 mg, 0.093 mmol). The reaction mixture was degassed and then heated at 85° C. for 2 h. The mixture was concentrated under vacuum, and the residue was purified by ISCO automated chromatography (40 g silica gel, 0-50% ethyl acetate/dichloromethane) to afford (4aR,6S,7R,8R,8aR)-6-(1-(5-chloro-2-(trifluoromethyl)phenyl)-3-methyl-1H-1,2,4-triazol-5-yl)-8-(4-(4-chloro-3-fluoro-5-methoxyphenyl)-1H-1,2,3-triazol-1-yl)-2-phenylhexahydropyrano[3,2-d][1,3]dioxin-7-ol (33 mg, 0.032 mmol, 61.2% yield) as a tan solid. MS (ESI) m/z: 721.4 [M+H]+.

Step 6. (2S,3R,4R,5R,6R)-2-(1-(5-Chloro-2-(trifluoromethyl)phenyl)-3-methyl-1H-1,2,4-triazol-5-yl)-4-(4-(4-chloro-3-fluoro-5-methoxyphenyl)-1H-1,2,3-triazol-1-yl)-6-(hydroxymethyl)tetrahydro-2H-pyran-3,5-diol A mixture of (4aR,6S,7R,8R,8aR)-6-(1-(5-chloro-2-(trifluoromethyl)phenyl)-3-methyl-1H-1,2,4-triazol-5-yl)-8-(4-(4-chloro-3-fluoro-5-methoxyphenyl)-1H-1,2,3-triazol-1-yl)-2-phenylhexahydropyrano[3,2-d][1,3]dioxin-7-ol (33 mg, 0.032 mmol) in acetic acid (1.05 mL) and water (0.45 mL) was stirred at 90° C. for 2 h. The mixture was diluted with methanol and injected to prep. HPLC (Column: Phenomenex Luna AXIA 30×100 C18 5u (10 min): Solvent A: 90% H2O-10% ACN-0.1% TFA, Solvent B: 10% ACN-90% H2O 0.1% TFA Gradient: 30-50% B over 15 min; Flow rate: 40 ml/min). The correct fractions were combined, concentrated under vacuum, basified to pH 9-10 with saturated NaHCO3 solution, and extracted with dichloromethane (3×30 mL). Removal of the solvent under vacuum provided the desired product, (2S,3R,4R,5R,6R)-2-(1-(5-chloro-2-(trifluoromethyl)phenyl)-3-methyl-1H-1,2,4-triazol-5-yl)-4-(4-(4-chloro-3-fluoro-5-methoxyphenyl)-1H-1,2,3-triazol-1-yl)-6-(hydroxymethyl)tetrahydro-2H-pyran-3,5-diol (10 mg, 0.015 mmol, 49.0% yield) as a white solid. MS (ESI) m/z: 721.4 [M+H]+; 1H NMR (400 MHz, METHANOL-d4) δ 8.58 (s, 1H), 7.96 (br d, J=8.58 Hz, 1H), 7.86 (br d, J=8.36 Hz, 1H), 7.76 (br s, 1H), 7.43 (s, 1H), 7.35 (br d, J=9.68 Hz, 1H), 4.85-4.90 (m, 2H), 4.33-4.40 (m, 1H), 4.13 (s, 1H), 4.00 (s, 3H), 3.71-3.77 (m, 1H), 3.64-3.70 (m, 2H), 2.45 (s, 3H). hGal-3 IC50=0.014 μM.

Example 4

2-(((2S,3R,4S,5R,6R)-2-(1-(5-chloro-2-(trifluoromethyl)phenyl)-3-methyl-1H-1,2,4-triazol-5-yl)-4-(4-(4-chloro-3,5-difluorophenyl)-1H-1,2,3-triazol-1-yl)-5-hydroxy-6-(hydroxymethyl)tetrahydro-2H-pyran-3-yl)oxy)-N-methylacetamide

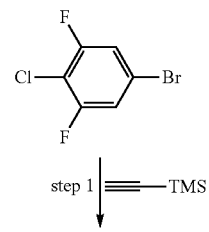

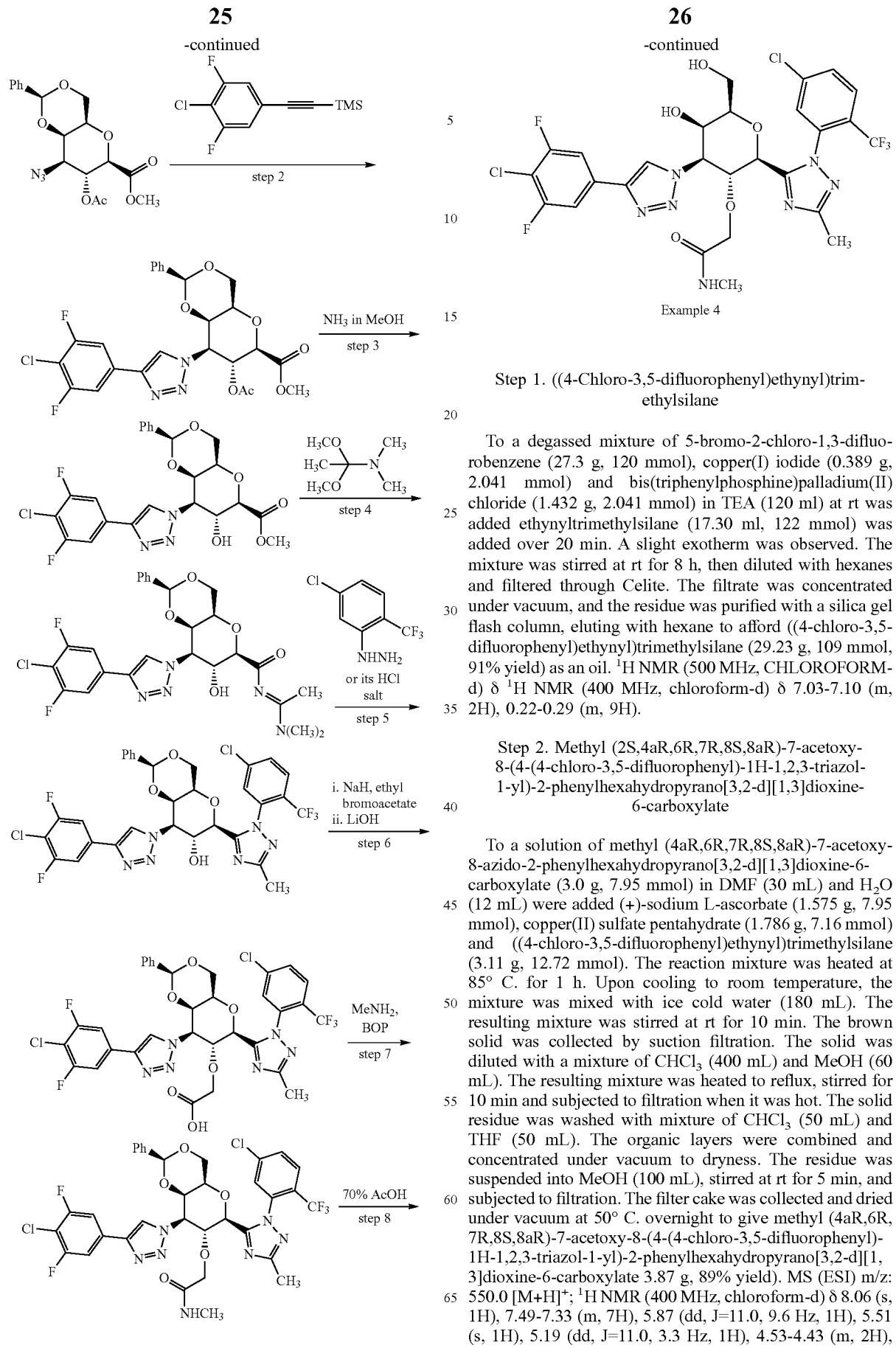

Example 4

Step 1. ((4-Chloro-3,5-difluorophenyl)ethynyl)trimethylsilane

To a degassed mixture of 5-bromo-2-chloro-1,3-difluorobenzene (27.3 g, 120 mmol), copper(I) iodide (0.389 g, 2.041 mmol) and bis(triphenylphosphine)palladium(II) chloride (1.432 g, 2.041 mmol) in TEA (120 ml) at rt was added ethynyltrimethylsilane (17.30 ml, 122 mmol) was added over 20 min. A slight exotherm was observed. The mixture was stirred at rt for 8 h, then diluted with hexanes and filtered through Celite. The filtrate was concentrated under vacuum, and the residue was purified with a silica gel flash column, eluting with hexane to afford ((4-chloro-3,5-difluorophenyl)ethynyl)trimethylsilane (29.23 g, 109 mmol, 91% yield) as an oil. $^1$H NMR (500 MHz, CHLOROFORM-d) δ $^1$H NMR (400 MHz, chloroform-d) δ 7.03-7.10 (m, 2H), 0.22-0.29 (m, 9H).

Step 2. Methyl (2S,4aR,6R,7R,8S,8aR)-7-acetoxy-8-(4-(4-chloro-3,5-difluorophenyl)-1H-1,2,3-triazol-1-yl)-2-phenylhexahydropyrano[3,2-d][1,3]dioxine-6-carboxylate To a solution of methyl (4aR,6R,7R,8S,8aR)-7-acetoxy-8-azido-2-phenylhexahydropyrano[3,2-d][1,3]dioxine-6-carboxylate (3.0 g, 7.95 mmol) in DMF (30 mL) and H$_2$O (12 mL) were added (+)-sodium L-ascorbate (1.575 g, 7.95 mmol), copper(II) sulfate pentahydrate (1.786 g, 7.16 mmol) and ((4-chloro-3,5-difluorophenyl)ethynyl)trimethylsilane (3.11 g, 12.72 mmol). The reaction mixture was heated at 85° C. for 1 h. Upon cooling to room temperature, the mixture was mixed with ice cold water (180 mL). The resulting mixture was stirred at rt for 10 min. The brown solid was collected by suction filtration. The solid was diluted with a mixture of CHCl$_3$ (400 mL) and MeOH (60 mL). The resulting mixture was heated to reflux, stirred for 10 min and subjected to filtration when it was hot. The solid residue was washed with mixture of CHCl$_3$ (50 mL) and THF (50 mL). The organic layers were combined and concentrated under vacuum to dryness. The residue was suspended into MeOH (100 mL), stirred at rt for 5 min, and subjected to filtration. The filter cake was collected and dried under vacuum at 50° C. overnight to give methyl (4aR,6R,7R,8S,8aR)-7-acetoxy-8-(4-(4-chloro-3,5-difluorophenyl)-1H-1,2,3-triazol-1-yl)-2-phenylhexahydropyrano[3,2-d][1,3]dioxine-6-carboxylate 3.87 g, 89% yield). MS (ESI) m/z: 550.0 [M+H]$^+$; $^1$H NMR (400 MHz, chloroform-d) δ 8.06 (s, 1H), 7.49-7.33 (m, 7H), 5.87 (dd, J=11.0, 9.6 Hz, 1H), 5.51 (s, 1H), 5.19 (dd, J=11.0, 3.3 Hz, 1H), 4.53-4.43 (m, 2H), 4.22 (d, J=9.6 Hz, 1H), 4.11 (dd, J=12.8, 1.8 Hz, 1H), 3.83-3.75 (m, 4H), 3.49 (d, J=4.7 Hz, 1H), 1.87 (s, 3H).

Step 3 (4aR,6R,7R,8R,8aR)-8-(4-(4-Chloro-3,5-difluorophenyl)-1H-1,2,3-triazol-1-yl)-7-hydroxy-2-phenylhexahydropyrano[3,2-d][1,3]dioxine-6-carboxamide Ammonia in methanol (7 N) (700 mL, 4900 mmol), pre-cooled in refrigerator, was added to methyl (4aR,6R,7R,8S,8aR)-7-acetoxy-8-(4-(4-chloro-3,5-difluorophenyl)-1H-1,2,3-triazol-1-yl)-2-phenylhexahydropyrano[3,2-d][1,3]dioxine-6-carboxylate (9.84 g, 17.89 mmol) in one portion. The mixture was stirred at room temperature in a sealed flask for 18 h. The mixture (now clear solution) was concentrated under vacuum to dryness. To the residue was added dichloromethane (30 mL) and the mixture was concentrated under vacuum to give (4aR,6R,7R,8R,8aR)-8-(4-(4-chloro-3,5-difluorophenyl)-1H-1,2,3-triazol-1-yl)-7-hydroxy-2-phenylhexahydropyrano[3,2-d][1,3]dioxine-6-carboxamide (9.28 g, 17.89 mmol, 100% yield, 95% pure) as a white solid: MS (ESI) m/z: 493.0 [M+H]$^+$; $^1$H NMR (400 MHz, chloroform-d) δ 8.03 (s, 1H), 7.47-7.40 (m, 2H), 7.40-7.31 (m, 5H), 6.88 (s, 1H), 5.66 (s, 1H), 5.49 (s, 1H), 5.04 (dd, J=10.5, 3.3 Hz, 1H), 4.92 (s, 1H), 4.66-4.49 (m, 2H), 4.43 (dd, J=12.8, 1.7 Hz, 1H), 4.15 (dd, J=12.8, 1.7 Hz, 1H), 4.04 (d, J=9.5 Hz, 1H), 3.84 (d, J=1.4 Hz, 1H).

Step 4. (4aR,6R,7R,8R,8aR)-8-(4-(4-Chloro-3,5-difluorophenyl)-1H-1,2,3-triazol-1-yl)-N-((E)-1-(dimethylamino)ethylidene)-7-hydroxy-2-phenylhexahydropyrano[3,2-d][1,3]dioxine-6-carboxamide A heterogeneous mixture of (4aR,6R,7R,8R,8aR)-8-(4-(4-chloro-3,5-difluorophenyl)-1H-1,2,3-triazol-1-yl)-7-hydroxy-2-phenylhexahydropyrano[3,2-d][1,3]dioxine-6-carboxamide (3.75 g, 7.30 mmol) and 1,1-dimethoxy-N,N-dimethylethan-1-amine (3.30 g, 22.30 mmol) in 1,4-dioxane (100 mL) was heated at 60° C. for 5 h. The volatiles were removed under vacuum. To the residue was added hexane (100 mL) and diethyl ether (20 mL). The mixture was stirred at rt for 5 min and the insoluble product, (4aR,6R,7R,8R,8aR)-8-(4-(4-chloro-3,5-difluorophenyl)-1H-1,2,3-triazol-1-yl)-N-((E)-1-(dimethylamino)ethylidene)-7-hydroxy-2-phenylhexahydropyrano[3,2-d][1,3]dioxine-6-carboxamide (4.34 g, 7.34 mmol, 100% yield, 95% pure), was collected as a beige solid by suction filtration and dried under vacuum overnight. MS (ESI) m/z: 562.1 [M+H]$^+$; $^1$H NMR (400 MHz, chloroform-d) δ 8.05 (s, 1H), 7.52-7.29 (m, 7H), 6.25 (s, 1H), 5.47 (s, 1H), 5.05 (dd, J=10.5, 3.4 Hz, 1H), 4.57 (dd, J=12.6, 1.5 Hz, 1H), 4.52-4.36 (m, 2H), 4.15-3.89 (m, 2H), 3.76 (d, J=1.5 Hz, 1H), 3.16 (s, 3H), 3.09 (s, 3H), 2.43 (s, 3H).

Step 5. (4aR,6S,7R,8R,8aR)-6-(1-(5-Chloro-2-(trifluoromethyl)phenyl)-3-methyl-1H-1,2,4-triazol-5-yl)-8-(4-(4-chloro-3,5-difluorophenyl)-1H-1,2,3-triazol-1-yl)-2-phenylhexahydropyrano[3,2-d][1,3]dioxin-7-ol A mixture of (4aR,6R,7R,8R,8aR)-8-(4-(4-chloro-3,5-difluorophenyl)-1H-1,2,3-triazol-1-yl)-N-((E)-1-(dimethylamino)ethylidene)-7-hydroxy-2-phenylhexahydropyrano[3,2-d][1,3]dioxine-6-carboxamide (3.00 g, 5.07 mmol) and (5-chloro-2-(trifluoromethyl)phenyl)hydrazine (1.175 g, 5.58 mmol) in dioxane (24 mL) and acetic Acid (24 mL) was stirred at 80° C. for 60 min. The mixture was concentrated under vacuum to almost dryness. The residue was diluted with ethyl acetate (450 mL), washed with 1M K$_2$HPO$_4$ solution (2×80 mL) and brine (80 mL). The organic layer was dried over anhydrous MgSO$_4$, filtered, and concentrated to give a crude product. This crude product was dissolved in CH$_2$Cl$_2$ (100 mL) and 15 g silica gel was added. The solvent was evaporate to give a solid residue, which was loaded into a solid loading cartridge and purified by ISCO automated chromatography (330 g silica gel, 0-2.5% MeOH/CH$_2$Cl$_2$ in 60 min gradient). The product thus obtain was further recrystallized from hexane and EtOAc to give (4aR,6S,7R,8R,8aR)-6-(1-(5-chloro-2-(trifluoromethyl)phenyl)-3-methyl-1H-1,2,4-triazol-5-yl)-8-(4-(4-chloro-3,5-difluorophenyl)-1H-1,2,3-triazol-1-yl)-2-phenylhexahydropyrano[3,2-d][1,3]dioxin-7-ol (1.899 g, 2.68 mmol, 52.8% yield) as a white solid. MS (ESI) m/z: 709.1 [M+H]$^+$; $^1$H NMR (400 MHz, chloroform-d) δ 8.04 (s, 1H), 7.75 (d, J=8.4 Hz, 1H), 7.69-7.57 (m, 2H), 7.47-7.39 (m, 2H), 7.39-7.28 (m, 5H), 5.38 (s, 1H), 5.07 (dd, J=10.8, 3.3 Hz, 1H), 4.78 (ddd, J=10.9, 9.0, 2.1 Hz, 1H), 4.60 (d, J=2.1 Hz, 1H), 4.55 (d, J=9.0 Hz, 1H), 4.46 (dd, J=3.3, 1.1 Hz, 1H), 3.92 (dd, J=12.8, 1.8 Hz, 1H), 3.76-3.67 (m, 1H), 3.52 (q, J=1.6 Hz, 1H), 2.43 (s, 3H).

Step 6. 2-(((4aR,6S,7R,8R,8aR)-6-(1-(5-Chloro-2-(trifluoromethyl)phenyl)-3-methyl-1H-1,2,4-triazol-5-yl)-8-(4-(4-chloro-3,5-difluorophenyl)-1H-1,2,3-triazol-1-yl)-2-phenylhexahydropyrano[3,2-d][1,3]dioxin-7-yl)oxy)acetic acid To a solution of (4aR,6S,7R,8R,8aR)-6-(1-(5-chloro-2-(trifluoromethyl)phenyl)-3-methyl-1H-1,2,4-triazol-5-yl)-8-(4-(4-chloro-3,5-difluorophenyl)-1H-1,2,3-triazol-1-yl)-2-phenylhexahydropyrano[3,2-d][1,3]dioxin-7-ol (500 mg, 0.705 mmol) in THF (10 mL) at 0° C. was added sodium hydride (60% oil dispersion) (56.4 mg, 1.410 mmol) in one portion. The mixture was stirred at 0° C. for 15 min before ethyl 2-bromoacetate (0.094 mL, 0.846 mmol) in THF (2 mL) was added over 1 min. The mixture was stirred at 0° C. for 45 min, then quenched with EtOH (2 mL), diluted with ethyl acetate (150 mL), washed with water (3×30 mL) and brine (30 mL), dried over anhydrous MgSO$_4$, and concentrated under vacuum to dryness. The residue was dissolved in THF (25 mL) and a solution of lithium hydroxide (67.2 mg, 2.81 mmol) in water (5 mL) was added at rt over 1 min. The mixture was stirred at rt for 1.5 h and then concentrated under vacuum to a volume of approximately 5 mL. The residue was diluted with water (15 mL) and acidified with 1 N HCl solution to pH 5-6. The insoluble product, 2-(((4aR, 6S,7R,8R,8aR)-6-(1-(5-chloro-2-(trifluoromethyl)phenyl)-3-methyl-1H-1,2,4-triazol-5-yl)-8-(4-(4-chloro-3,5-difluorophenyl)-1H-1,2,3-triazol-1-yl)-2-phenylhexahydropyrano[3,2-d][1,3]dioxin-7-yl)oxy)acetic acid (532 mg, 0.693 mmol, 98% yield), was collected as a white solid bu suction filtration and dried at 50° C. under vacuum. MS (ESI) m/z: 767.4 [M+H]$^+$.

Step 7. 2-(((4aR,6S,7R,8R,8aR)-6-(1-(5-Chloro-2-(trifluoromethyl)phenyl)-3-methyl-1H-1,2,4-triazol-5-yl)-8-(4-(4-chloro-3,5-difluorophenyl)-1H-1,2,3-triazol-1-yl)-2-phenylhexahydropyrano[3,2-d][1,3]dioxin-7-yl)oxy)-N-methylacetamide A mixture of 2-(((4aR,6S,7R,8R,8aR)-6-(1-(5-chloro-2-(trifluoromethyl)phenyl)-3-methyl-1H-1,2,4-triazol-5-yl)-8-(4-(4-chloro-3,5-difluorophenyl)-1H-1,2,3-triazol-1-yl)-2-phenylhexahydropyrano[3,2-d][1,3]dioxin-7-yl)oxy)acetic acid (30 mg, 0.039 mmol), methylamine in THF (0.039 mL, 0.078 mmol), BOP (25.9 mg, 0.059 mmol), and N,N-diisopropylethylamine (0.020 mL, 0.117 mmol) in DMF (0.5 mL) was stirred at rt for 2 h. It was diluted with ethyl acetate (50 mL), washed with water (2×20 mL), 0.5 N HCl solution (20 mL) and brine (20 mL), and dried over anhydrous $MgSO_4$. Removal of the solvent under vacuum provided 2-(((4aR,6S,7R,8R,8aR)-6-(1-(5-chloro-2-(trifluoromethyl)phenyl)-3-methyl-1H-1,2,4-triazol-5-yl)-8-(4-(4-chloro-3,5-difluorophenyl)-1H-1,2,3-triazol-1-yl)-2-phenylhexahydropyrano[3,2-d][1,3]dioxin-7-yl)oxy)-N-methylacetamide (30 mg, 0.038 mmol, 98% yield) as a white solid, which was used in the next step without further purification.

Step 8. 2-(((2S,3R,4S,5R,6R)-2-(1-(5-Chloro-2-(trifluoromethyl)phenyl)-3-methyl-1H-1,2,4-triazol-5-yl)-4-(4-(4-chloro-3,5-difluorophenyl)-1H-1,2,3-triazol-1-yl)-5-hydroxy-6-(hydroxymethyl)tetrahydro-2H-pyran-3-yl)oxy)-N-methylacetamide A mixture of 2-(((4aR,6S,7R,8R,8aR)-6-(1-(5-chloro-2-(trifluoromethyl)phenyl)-3-methyl-1H-1,2,4-triazol-5-yl)-8-(4-(4-chloro-3,5-difluorophenyl)-1H-1,2,3-triazol-1-yl)-2-phenylhexahydropyrano[3,2-d][1,3]dioxin-7-yl)oxy)-N-methylacetamide (30 mg, 0.038 mmol) and 70% acetic acid (2.5 mL, 0.038 mmol) was heated at 70° C. for 9 h. The mixture was diluted with methano and injected to prep. HPLC (Column: Phenomenex Luna AXIA 5u C18 21.2×100 (10 min); Solvent A: 90% $H_2O$-10% methanol-0.1% TFA, Solvent B: 10% methanol-90% $H_2O$ 0.1% TFA; Gradient: 20-100% B over 15 min; Flow rate: 20 ml/min). The correct fractions were combined, concentrated under vacuum, basified to pH 9-10 with saturated $NaHCO_3$ solution, and extracted with dichloromethane (3×30 mL). The combined extract was dried over anhydrous $Na_2SO_4$. Removal of the solvent under vacuum provided the desired product, 2-(((2S,3R,4S,5R,6R)-2-(1-(5-chloro-2-(trifluoromethyl)phenyl)-3-methyl-1H-1,2,4-triazol-5-yl)-4-(4-(4-chloro-3,5-difluorophenyl)-1H-1,2,3-triazol-1-yl)-5-hydroxy-6-(hydroxymethyl)tetrahydro-2H-pyran-3-yl)oxy)-N-methylacetamide (18 mg, 0.026 mmol, 67.6% yield), as a white solid. MS (ESI) m/z: 692.0 $[M+H]^+$. $^1H$ NMR (500 MHz, methanol-$d_4$) δ 8.82 (s, 1H), 7.99 (d, J=9.1 Hz, 1H), 7.94-7.85 (m, 2H), 7.74-7.64 (m, 2H), 5.11 (dd, J=10.6, 2.9 Hz, 1H), 4.96 (br t, J=9.8 Hz, 1H), 4.50 (d, J=9.1 Hz, 1H), 4.13 (d, J=3.0 Hz, 1H), 3.93 (br d, J=15.1 Hz, 1H), 3.77-3.58 (m, 4H), 2.54 (s, 3H), 2.46 (s, 3H). hGal-3 $IC_{50}$=0.023 µM.

Examples 5 to 25 in the table below were synthesized using the procedures described for Examples 1 to 4.

| EX # | Structure | LCMS (Method A)/ $^1$H NMR (400 MHz, methanol-$d_4$, unless otherwise indicated) | hGal-3 $IC_{50}$ (nM) |
|---|---|---|---|
| 5 | 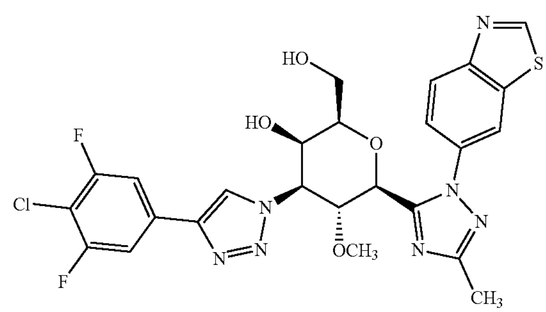 [SMILES: CO[C@@H]1[C@@H](n2cc(-c3cc(F)c(Cl)c(F)c3)nn2)[C@@H](O)[C@@H](CO)O[C@H]1c1nc(C)nn1-c1ccc2ncsc2c1] | MS (ESI) m/z: 590.2. δ 9.42 (s, 1H), 8.80 (s, 1H), 8.52 (d, J = 2.2 Hz, 1H), 8.28 (d, J = 8.7 Hz, 1H), 7.86 (dd, J = 8.7, 2.1 Hz, 1H), 7.75-7.59 (m, 2H), 5.01 (dd, J = 10.5, 2.9 Hz, 1H), 4.74 (dd, J = 10.5, 9.3 Hz, 1H), 4.61 (d, J = 9.4 Hz, 1H), 4.12 (d, J = 2.9 Hz, 1H), 3.96-3.82 (m, 2H), 3.81-3.68 (m, 1H), 2.97 (s, 3H), 2.51 (s, 3H). | 20 |
| 6 | 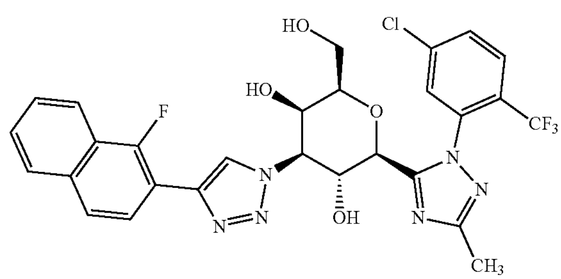 [SMILES: Cc1nc([C@@H]2O[C@H](CO)[C@H](O)[C@H](n3cc(-c4ccc5ccccc5c4F)nn3)[C@H]2O)n(-c2cc(Cl)ccc2C(F)(F)F)n1] | MS (ESI) m/z: 619.0. δ 8.59 (d, J = 3.30 Hz, 1H), 8.23 (dd, J = 7.15, 8.69 Hz, 1H), 8.17 (d, J = 7.92 Hz, 1H), 7.96 (t, J = 9.13 Hz, 2H), 7.85-7.90 (m, 1H), 7.80 (d, J = 8.80 Hz, 2H), 7.56-7.65 (m, 2H), 4.89-4.96 (m, 2H), 4.39 (d, J = 8.80 Hz, 1H), 4.16 (d, J = 1.54 Hz, 1H), 3.76 (d, J = 6.16 Hz, 1H), 3.66-3.72 (m, 2H), 2.46 (s, 3H). | 62 |
| 7 | 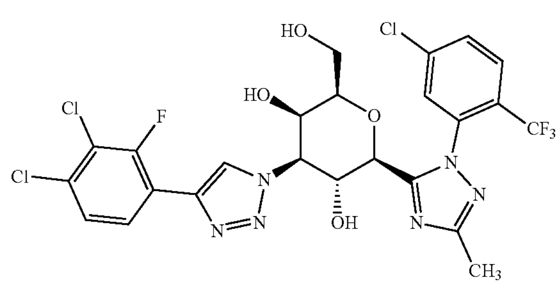 [SMILES: Cc1nc([C@@H]2O[C@H](CO)[C@H](O)[C@H](n3cc(-c4ccc(Cl)c(Cl)c4F)nn3)[C@H]2O)n(-c2cc(Cl)ccc2C(F)(F)F)n1] | MS (ESI) m/z: 637.2. δ 8.47 (d, J = 3.52 Hz, 1H), 8.08 (dd, J = 7.48, 8.58 Hz 1H), 7.96 (d, J = 8.58 Hz, 1H), 7.82-7.90 (m, 1H), 7.72-7.82 (m, 1H), 7.50 (dd, J = 1.54, 8.58 Hz, 1H), 4.86-4.95 (m, 2H), 4.37 (d, J = 8.80 Hz, 1H), 4.12 (d, J = 1.76 Hz, 1H), 3.71-3.76 (m, 1H), 3.64-3.68 (m, 2H), 2.45 (s, 3H). | 6 |

-continued

| EX # | Structure | LCMS (Method A)/ ¹H NMR (400 MHz, methanol-d₄, unless otherwise indicated) | hGal-3 IC₅₀ (nM) |
|---|---|---|---|
| 8 | 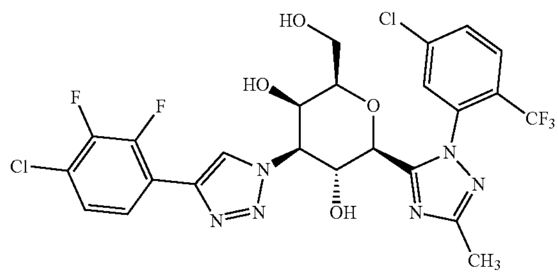 | MS (ESI) m/z: 636.8. δ 8.36 (d, J = 3.4 Hz, 1H), 7.82 (ddd, J = 9.1, 7.0, 2.2 Hz, 1H), 7.69 (d, J = 2.6 Hz, 1H), 7.64 (dd, J = 8.9, 2.6 Hz, 1H), 7.51 (dq, J = 9.0, 1.5 Hz, 1H), 7.31 (ddd, J = 8.8, 6.7, 2.0 Hz, 1H), 4.83 (dd, J = 10.8, 2.9 Hz, 1H), 4.71-4.76 (m, 1H), 4.32 (d, J = 9.2 Hz, 1H), 4.05 (dd, J = 2.9, 1.1 Hz, 1H), 3.70 (td, J = 6.2, 5.7, 1.0 Hz, 1H), 3.58 (d, J = 6.1 Hz, 2H), 2.35 (s, 3H). | 17 |
| 9 | 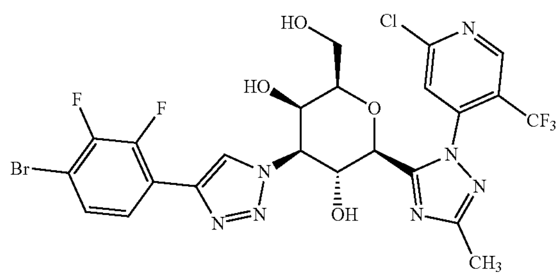 [SMILES: Cc1nc([C@@H]2O[C@H](CO)[C@H](O)[C@H](n3cc(-c4ccc(Br)c(F)c4F)nn3)[C@H]2O)n(-c2cc(Cl)ncc2C(F)(F)F)n1] | MS (ESI) m/z: 666.2. ¹H NMR (500 MHz, methanol-d₄) δ 8.97 (d, J = 1.9 Hz, 1H), 8.47 (d, J = 3.3 Hz, 1H), 8.35 (d, J = 1.1 Hz, 1H), 7.90 (ddd, J = 8.7, 6.8, 2.1 Hz, 1H), 7.56 (ddd, J = 8.7, 6.5, 1.9 Hz, 1H), 4.93 (dd, J = 10.7, 3.0 Hz, 1H), 4.83-4.75 (m, 1H), 4.52 (d, J = 9.4 Hz, 1H), 4.15-4.10 (m, 1H), 3.81-3.75 (m, 1H), 3.68-3.58 (m, 2H), 2.47 (s, 3H). | 12 |
| 10 | 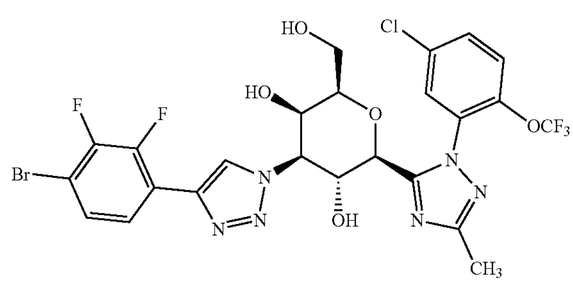 [SMILES: Cc1nc([C@@H]2O[C@H](CO)[C@H](O)[C@H](n3cc(-c4ccc(Br)c(F)c4F)nn3)[C@H]2O)n(-c2cc(Cl)ccc2OC(F)(F)F)n1] | MS (ESI) m/z: 680.8. δ 8.37 (d, J = 3.4 Hz, 1H), 7.77 (ddd, J = 8.9, 6.8, 2.1 Hz, 1H), 7.69 (d, J = 2.6 Hz, 1H), 7.64 (dd, J = 8.9, 2.6 Hz, 1H), 7.51 (dq, J = 8.9, 1.5 Hz, 1H), 7.43 (ddd, J = 8.5, 6.2, 2.0 Hz, 1H), 4.83 (dd, J = 10.8, 2.9 Hz, 1H), 4.68-4.76 (m, 1H), 4.32 (d, J = 9.1 Hz, 1H), 4.05 (dd, J = 2.8, 1.1 Hz, 1H), 3.70 (td, J = 6.1, 5.7, 1.1 Hz, 1H), 3.58 (d, J = 6.1 Hz, 2H), 2.35 (s, 3H). | 11 |
| 11 | 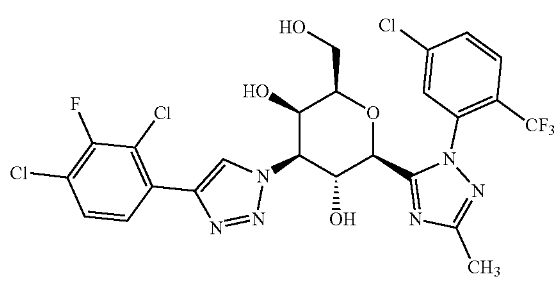 | MS (ESI) m/z: 636.8. δ 8.68 (s, 1H), 7.96 (br d, J = 8.58 Hz, 1H), 7.82-7.93 (m, 2H), 7.77 (br s, 1H), 7.53-7.60 (m, 1H), 4.88-4.95 (m, 2H), 4.37 (br d, J = 9.02 Hz, 1H), 4.13 (br s, 1H), 3.71-3.77 (m, 1H), 3.67 (br d, J = 5.28 Hz, 2H), 2.44 (s, 3H). | 14 |
| 12 | 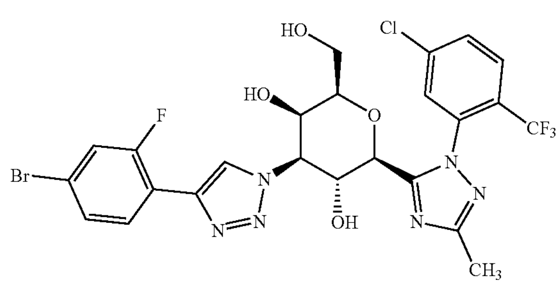 [SMILES: Cc1nc([C@@H]2O[C@H](CO)[C@H](O)[C@H](n3cc(-c4ccc(Br)cc4F)nn3)[C@H]2O)n(-c2cc(Cl)ccc2C(F)(F)F)n1] | MS (ESI) m/z: 647.3. δ 8.41 (d, J = 3.52 Hz, 1H), 8.00-8.10 (m, 1H), 7.92-7.98 (m, 1H), 7.83-7.89 (m, 1H), 7.73-7.79 (m, 1H), 7.45-7.53 (m, 2H), 4.84-4.91 (m, 2H), 4.36 (d, J = 9.02 Hz, 1H), 4.11 (d, J = 1.54 Hz, 1H), 3.70-3.76 (m, 1H), 3.62-3.68 (m, 2H), 2.44 (s, 3H). | 56 |

| EX # | Structure | LCMS (Method A)/ $^1$H NMR (400 MHz, methanol-$d_4$, unless otherwise indicated) | hGal-3 IC$_{50}$ (nM) |
|---|---|---|---|
| 13 | 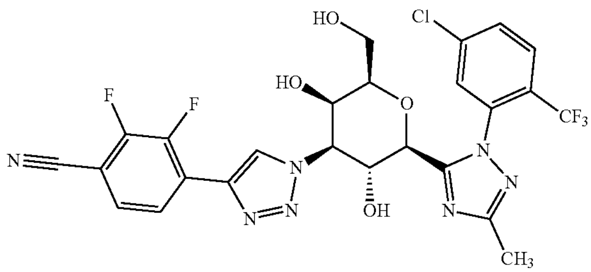 [SMILES: Cc1nc([C@@H]2O[C@H](CO)[C@H](O)[C@H](n3cc(-c4ccc(C#N)c(F)c4F)nn3)[C@H]2O)n(-c2cc(Cl)ccc2C(F)(F)F)n1] | MS (ESI) m/z: 612.4. δ 8.56-8.62 (m, 1H), 8.15 (ddd, J = 1.76, 6.38, 8.36 Hz, 1H), 7.94-8.00 (m, 1H), 7.83-7.90 (m, 1H), 7.77 (br s, 1H), 7.68 (ddd, J = 1.76, 6.11, 8.20 Hz, 1H), 4.88-4.98 (m, 2H), 4.38 (d, J = 9.02 Hz, 1H), 4.13 (d, J = 1.98 Hz, 1H), 3.74 (d, J = 6.16 Hz, 1H), 3.63-3.71 (m, 2H), 2.46 (s, 3H). | 19 |
| 14 | 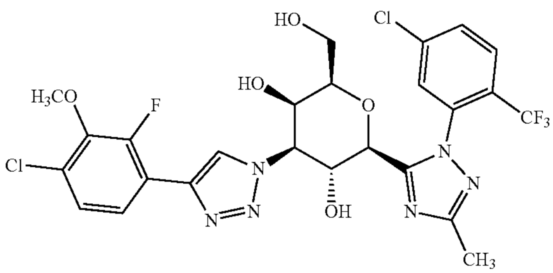 [SMILES: COc1c(Cl)ccc(-c2cn([C@H]3[C@@H](O)[C@@H](CO)O[C@@H](c4nc(C)nn4-c4cc(Cl)ccc4C(F)(F)F)[C@@H]3O)nn2)c1F] | MS (ESI) m/z: 633.4. δ 8.44 (d, J = 3.52 Hz, 1H), 7.96 (d, J = 8.58 Hz, 1H), 7.79-7.89 (m, 2H), 7.73-7.79 (m, 1H), 7.33 (dd, J = 1.54, 8.80 Hz, 1H), 4.88-4.92 (m, 2H), 4.36 (br d, J = 9.02 Hz, 1H), 4.12 (br d, J = 1.32 Hz, 1H), 3.99 (s, 3H), 3.71-3.77 (m, 1H), 3.67 (br d, J = 5.50 Hz, 2H), 2.45 (s, 3H). | 137 |
| 15 | 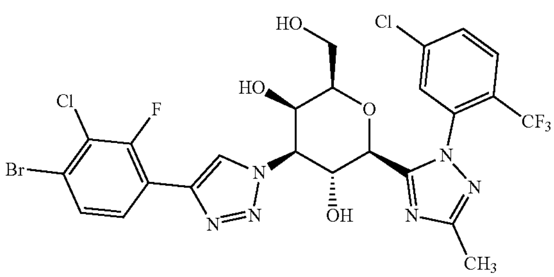 [SMILES: Cc1nc([C@@H]2O[C@H](CO)[C@H](O)[C@H](n3cc(-c4ccc(Br)c(Cl)c4F)nn3)[C@H]2O)n(-c2cc(Cl)ccc2C(F)(F)F)n1] | MS (ESI) m/z: 681.2. $^1$H NMR (500 MHz, methanol-$d_4$) δ 8.48 (d, J = 3.85 Hz, 1H), 8.03 (dd, J = 7.29, 8.39 Hz, 1H), 7.97 (d, J = 8.80 Hz, 1H), 7.87 (br d, J = 8.80 Hz, 1H), 7.78 (br d, J = 3.03 Hz, 1H), 7.66 (dd, J = 1.51, 8.67 Hz, 1H), 4.87-4.94 (m, 2H), 4.37 (br d, J = 9.08 Hz, 1H), 4.13 (d, J = 1.65 Hz, 1H), 3.74 (d, J = 6.33 Hz, 1H), 3.65-3.69 (m, 2H), 2.46 (s, 3H). | 96 |
| 16 | 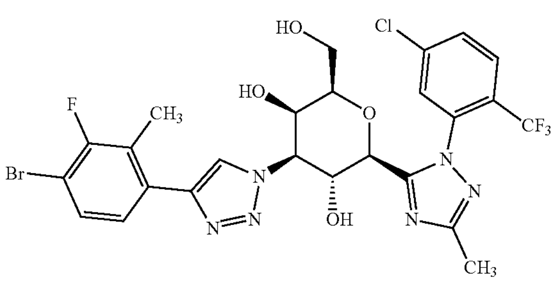 [SMILES: Cc1nc([C@@H]2O[C@H](CO)[C@H](O)[C@H](n3cc(-c4ccc(Br)c(F)c4C)nn3)[C@H]2O)n(-c2cc(Cl)ccc2C(F)(F)F)n1] | MS (ESI) m/z: 661.2. δ 8.30 (s, 1H), 7.92-7.99 (m, 1H), 7.86 (br d, J = 1.10 Hz, 1H), 7.76 (br s, 1H), 7.48-7.56 (m, 1H), 7.40 (dd, J = 0.99, 8.47 Hz, 1H), 4.85-4.92 (m, 2H), 4.36 (d, J = 8.80 Hz, 1H), 4.12 (d, J = 1.54 Hz, 1H), 3.70-3.76 (m, 1H), 3.62-3.70 (m, 2H), 2.43 (s, 3H), 2.42 (d, J = 2.42 Hz, 3H). | 74 |
| 17 | 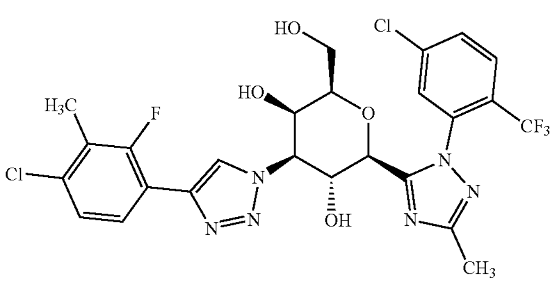 [SMILES: Cc1nc([C@@H]2O[C@H](CO)[C@H](O)[C@H](n3cc(-c4ccc(Cl)c(C)c4F)nn3)[C@H]2O)n(-c2cc(Cl)ccc2C(F)(F)F)n1] | MS (ESI) m/z: 617.2. δ 8.41 (d, J = 3.74 Hz, 1H), 7.90-7.97 (m, 2H), 7.82-7.88 (m, 1H), 7.76 (br s, 1H), 7.29-7.35 (m, 1H), 4.85-4.91 (m, 2H), 4.35 (d, J = 8.0 Hz, 1H), 4.11 (d, J = 1.54 Hz, 1H), 3.70-3.75 (m, 1H), 3.63-3.68 (m, 2H), 2.44 (s, 3H), 2.38 (d, J = 2.42 Hz, 3H). | 18 |

-continued

| EX # | Structure | LCMS (Method A)/ ¹H NMR (400 MHz, methanol-d₄, unless otherwise indicated) | hGal-3 IC$_{50}$ (nM) |
|---|---|---|---|
| 18 | 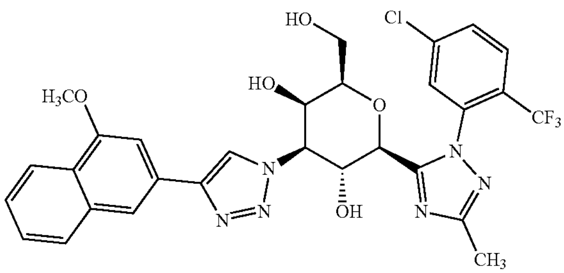 [SMILES: COc1cc(-c2cn([C@H]3[C@@H](O)[C@@H](CO)O[C@@H](c4nc(C)nn4-c4cc(Cl)ccc4C(F)(F)F)[C@@H]3O)nn2)cc2ccccc12] | MS (ESI) m/z: 630.8. δ 8.42 (s, 1H), 8.16 (d, J = 1.6 Hz, 1H), 7.86 (d, J = 8.6 Hz, 1H), 7.81 (dd, J = 8.5, 1.7 Hz, 1H), 7.79-7.70 (m, 3H), 7.68 (s, 1H), 7.16 (d, J = 2.5 Hz, 1H), 7.06 (dd, J = 8.9, 2.5 Hz, 1H), 4.77 (s, 2H), 4.32-4.21 (m, 1H), 4.05 (q, J = 1.1 Hz, 1H), 3.83 (s, 3H), 3.61-3.67 (m, 1H), 3.61-3.47 (m, 2H), 2.35 (s, 3H). | 1330 |
| 19 | 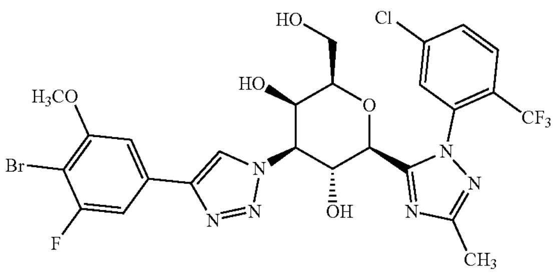 [SMILES: COc1cc(-c2cn([C@H]3[C@@H](O)[C@@H](CO)O[C@@H](c4nc(C)nn4-c4cc(Cl)ccc4C(F)(F)F)[C@@H]3O)nn2)cc(F)c1Br] | MS (ESI) m/z: 677.2. δ 8.59 (s, 1H), 7.96 (br d, J = 8.58 Hz, 1H), 7.86 (br d, J = 8.36 Hz, 1H), 7.70-7.80 (m, 1H), 7.39 (s, 1H), 7.27-7.36 (m, 1H), 4.86 (br s, 2H), 4.32-4.40 (m, 1H), 4.10-4.15 (m, 1H), 4.00 (s, 3H), 3.73 (q, J = 6.09 Hz, 1H), 3.63-3.71 (m, 2H), 2.45 (s, 3H). | 23 |
| 20 | 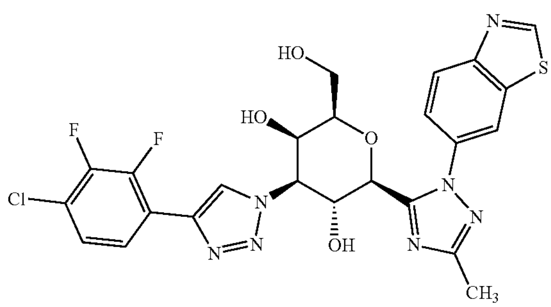 [SMILES: Cc1nc([C@@H]2O[C@H](CO)[C@H](O)[C@H](n3cc(-c4ccc(Cl)c(F)c4F)nn3)[C@H]2O)n(-c2ccc3ncsc3c2)n1] | MS (ESI) m/z: 575.7 (Method A). ¹H NMR (400 MHz, methanol-d4) δ 9.25 (s, 1H), 8.37 (d, J = 2.1 Hz, 1H), 8.32 (d, J = 3.4 Hz, 1H), 8.10 (d, J = 8.8 Hz, 1H), 7.75 (ddd, J = 9.0, 7.0, 2.2 Hz, 1H), 7.71 (dd, J = 8.7, 2.1 Hz, 1H), 7.24 (ddd, J = 8.7, 6.7, 2.0 Hz, 1H), 4.89-4.76 (m, 2H), 4.52-4.31 (m, 1H), 4.06-3.96 (m, 1H), 3.74 (ddd, J = 7.3, 4.1, 1.0 Hz, 1H), 3.68 (dd, J = 11.4, 7.4 Hz, 1H), 3.57 (dd, J = 11.4, 4.0 Hz, 1H), 2.32 (s, 3H). | 9 |
| 21 | 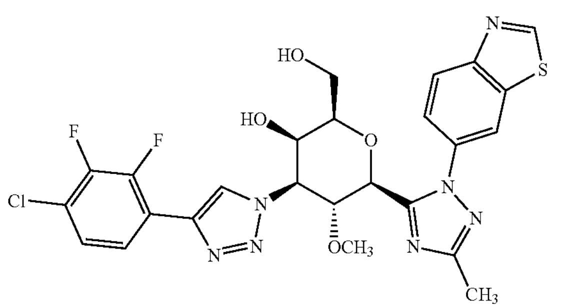 [SMILES: CO[C@@H]1[C@@H](n2cc(-c3ccc(Cl)c(F)c3F)nn2)[C@@H](O)[C@@H](CO)O[C@H]1c1nc(C)nn1-c1ccc2ncsc2c1] | MS (ESI) m/z: 589.8. δ 9.40 (s, 1H), 8.60 (d, J = 3.4 Hz, 1H) 8.50 (d, J = 2.1 Hz, 1H), 8.25 (d, J = 8.8 Hz, 1H), 7.91 (ddd, J = 9.0, 7.0, 2.2 Hz, 1H), 7.84 (dd, J = 8.7, 2.2 Hz, 1H), 7.40 (ddd, J = 8.7, 6.7, 2.0 Hz, 1H), 5.01 (dd, J = 10.5, 3.0 Hz, 1H), 4.73 (dd, J = 10.5, 9.4 Hz, 1H), 4.58 (d, J = 9.4 Hz, 1H), 4.11 (d, J = 2.9 Hz, 1H), 3.94-3.80 (m, 2H), 3.79-3.66 (m, 1H), 2.93 (s, 3H), 2.48 (s, 3H). | 10 |
| 22 | 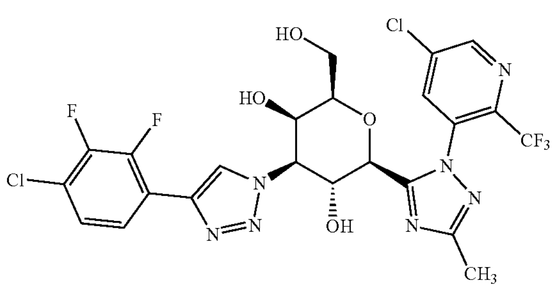 [SMILES: Cc1nc([C@@H]2O[C@H](CO)[C@H](O)[C@H](n3cc(-c4ccc(Cl)c(F)c4F)nn3)[C@H]2O)n(-c2cc(Cl)cnc2C(F)(F)F)n1] | MS (ESI) m/z: 622.1. δ 8.93-8.98 (m, 1H), 8.46 (d, J = 3.52 Hz, 1H), 8.33 (s, 1H), 7.93 (s, 1H), 7.42 (ddd, J = 1.98, 6.71, 8.69 Hz, 1H), 4.73-4.98 (m, 2H), 4.52 (s, 1H), 4.11 (d, J = 2.20 Hz, 1H), 3.77 (s, 1H), 3.58-3.65 (m, 2H), 2.46 (s, 3H). | 55 |

| EX # | Structure | LCMS (Method A)/ $^1$H NMR (400 MHz, methanol-$d_4$, unless otherwise indicated) | hGal-3 IC$_{50}$ (nM) |
|---|---|---|---|
| 23 | 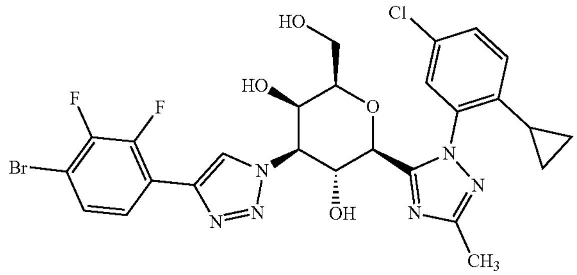 [SMILES: Cc1nc([C@@H]2O[C@H](CO)[C@H](O)[C@H](n3cc(-c4ccc(Br)c(F)c4F)nn3)[C@H]2O)n(-c2cc(Cl)ccc2C2CC2)n1] | MS (ESI) m/z: 636.6. δ 8.48 (d, J = 3.4 Hz, 1H), 7.89 (ddd, J = 8.8, 6.9, 2.1 Hz, 1H), 7.54 (ddd, J = 14.2, 8.4, 2.1 Hz, 2H), 7.46 (s, 1H), 7.14 (d, J = 8.5 Hz, 1H), 4.92 (dd, J = 10.7, 2.9 Hz, 1H), 4.79-4.88 (m, 1H), 4.46-4.33 (m, 1H), 4.14 (dd, J = 2.4, 0.9 Hz, 1H), 3.84-3.76 (m, 1H), 3.76-3.66 (m, 2H), 2.48 (s, 3H), 1.59 (td, J = 8.5, 4.3 Hz, 1H), 0.81-1.06 (m, 2H), 0.81-0.64 (m, 2H). | 20 |
| 24 | 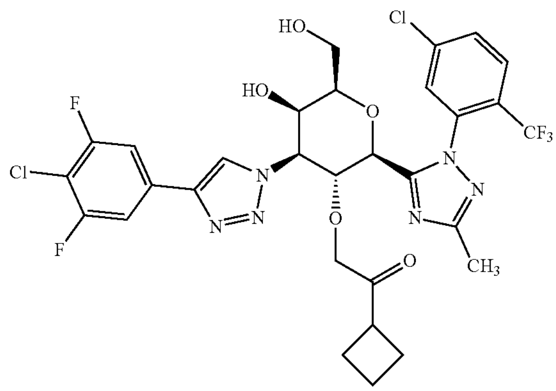 [SMILES: Cc1nc([C@@H]2O[C@H](CO)[C@H](O)[C@H](n3cc(-c4cc(F)c(Cl)c(F)c4)nn3)[C@H]2OCC(=O)C2CCC2)n(-c2cc(Cl)ccc2C(F)(F)F)n1] | MS (ESI) m/z: 718.0. $^1$H NMR (500 MHz, methanol-$d_4$) δ 8.78 (s, 1H), 7.99 (d, J = 8.5 Hz, 1H), 7.93 (d, J = 1.7 Hz, 1H), 7.90 (d, J = 8.3 Hz, 1H), 7.71 (d, J = 8.0 Hz, 2H), 5.08 (dd, J = 10.6, 2.9 Hz, 1H), 4.46 (d, J = 9.1 Hz, 1H), 4.11 (d, J = 2.8 Hz, 1H), 4.02-3.86 (m, 3H), 3.84-3.64 (m, 7H), 2.48 (s, 3H), 2.22-2.13 (m, 2H). | 28 |
| 25 | 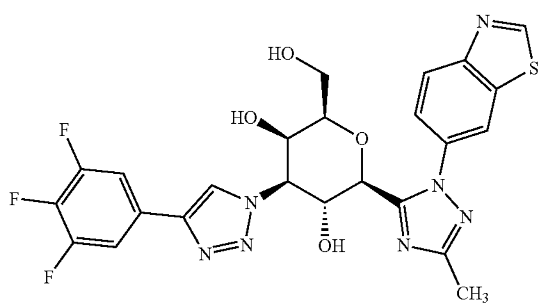 [SMILES: Cc1nc([C@@H]2O[C@H](CO)[C@H](O)[C@H](n3cc(-c4cc(F)c(F)c(F)c4)nn3)[C@H]2O)n(-c2ccc3ncsc3c2)n1] | MS (ESI) m/z: 559.6. $^1$H NMR (500 MHz, DMSO-$d_6$) δ 9.55 (s, 1H), 8.86 (s, 1H), 8.59 (d, J = 2.3 Hz, 1H), 8.27 (d, J = 8.6 Hz, 1H), 7.96-7.78 (m, 3H), 5.35-5.48 (m, 2H), 5.08-4.84 (m, 3H), 4.49 (d, J = 8.1 Hz, 1H), 3.97 (s, 1H), 3.86 (dd, J = 7.6, 4.3 Hz, 1H), 3.56-3.65 (m, 1H), 3.45-3.56 (m, 1H), 2.41 (s, 3H). | |

Preparation of 4-chloro-2-isothiocyanato-1-(trifluoromethyl)benzene

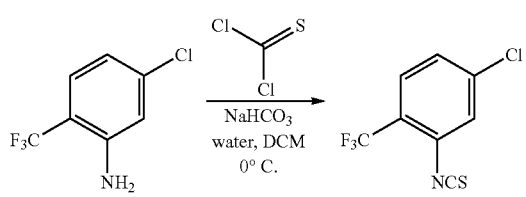

To a 200 mL pear shaped flask were added sodium bicarbonate (7.7 g, 92 mmol) and water (30 mL). After stirring 10 min, DCM (30 mL) and 5-chloro-2-(trifluoromethyl)aniline (2.1 mL, 15 mmol) were added. The mixture was cooled to 0° C., then thiophosgene (1.8 mL, 23 mmol) was added over a period of 10 min. The reaction was allowed to slowly reach rt and stirred. After 18 h, the reaction was diluted with water (200 mL) and extracted with DCM (2×100 mL). The organic phase was combined, washed with brine, dried over Na$_2$SO$_4$, filtered and concentrated. The residue was purified by flash column chromatography (80 g silica gel cartridge; A=Hex, B=EtOAc; 30 min grad.; 0% B to 40% B; flow rate=60 mL/min). The pure fractions were combined, concentrated and dried in vacuo to afford the title compound (2.0 g, 8.3 mmol, 54% yield) as a pale yellow oil. MS (ESI) m/z: 237.9 [M+H]$^+$ (Method B). $^1$H NMR (500 MHz, CHLOROFORM-d) δ 7.66-7.57 (m, 1H), 7.45-7.41 (m, 1H), 7.39-7.33 (m, 1H).

Preparation of 4-chloro-2-isothiocyanato-1-(trifluoromethoxy)benzene

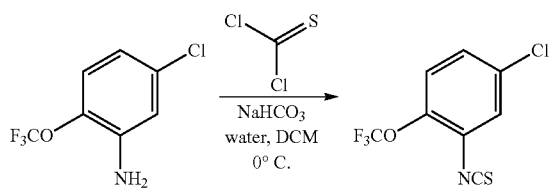

To a 200 mL pear shaped flask were added sodium bicarbonate (7.2 g, 85 mmol) and water (60 mL). After stirring 10 min, DCM (60 mL) and 5-chloro-2-(trifluoromethoxy)aniline (3.0 g, 14 mmol) were added. The mixture was cooled to 0° C., then thiophosgene (1.6 mL, 21 mmol) was added over a period of 10 min. The reaction was allowed to slowly reach rt and stirred. After 18 h, the reaction was diluted with water (200 mL) and extracted with DCM (2×100 mL). The organic phase was combined, washed with brine, dried over Na$_2$SO$_4$, filtered and concentrated. The residue was purified by flash column chromatography (80 g silica gel cartridge; A=Hex, B=EtOAc; 30 min grad.; 0% B to 40% B; flow rate=60 mL/min). The pure fractions were combined, concentrated and dried in vacuo to afford the title compound (3.2 g, 13 mmol, 90% yield) as a pale yellow oil. $^1$H NMR (500 MHz, CHLOROFORM-d) δ 7.30-7.25 (m, 3H).

Example 26

(2S,3R,4R,5R,6R)-4-(4-(4-bromo-2,3-difluorophenyl)-1H-1,2,3-triazol-1-yl)-2-(4-(5-chloro-2-(trifluoromethyl)phenyl)-4H-1,2,4-triazol-3-yl)-6-(hydroxymethyl)tetrahydro-2H-pyran-3,5-diol

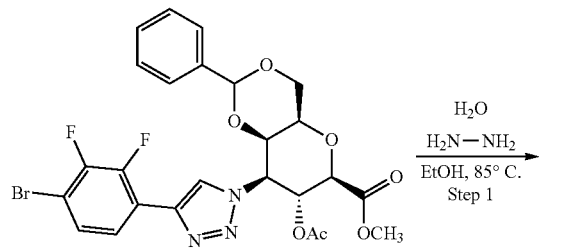

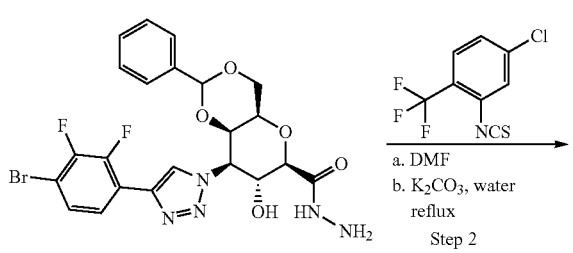

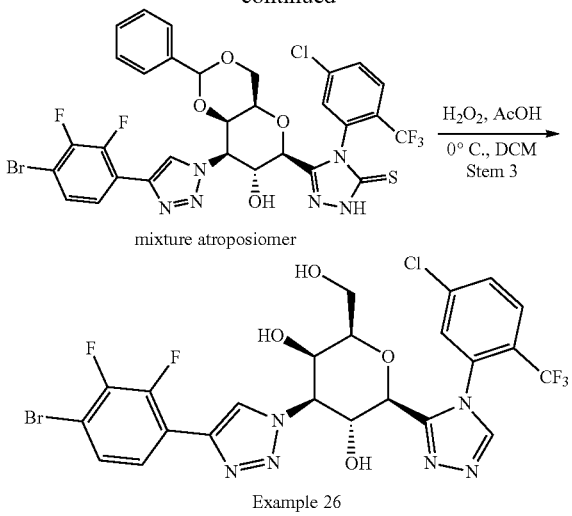

Example 26

Step 1: Preparation of (4aR,6R,7R,8R,8aR)-8-(4-(4-bromo-2,3-difluorophenyl)-1H-1,2,3-triazol-1-yl)-7-hydroxy-2-phenylhexahydropyrano[3,2-d][1,3]dioxine-6-carbohydrazide To a 200 mL pear shaped flask were added methyl (4aR,6R,7R,8S,8aR)-7-acetoxy-8-(4-(4-bromo-2,3-difluorophenyl)-1H-1,2,3-triazol-1-yl)-2-phenylhexahydropyrano[3,2-d][1,3]dioxine-6-carboxylate (250 mg, 0.42 mmol), hydrazine hydrate (0.31 mL, 4.2 mmol), and ethanol (8 mL). The reaction was stirred at 85° C. After 18 h, the solvent was concentrated and the residue was purified by preparative HPLC (5×2 mL injection; Method: Grad. Solv. System: From 40% A: 60% B to 0% A:100% B; (A=10% MeCN/90% H$_2$O+0.1% TFA); (B=90% MeCN/10% H$_2$O+0.1% TFA); Detection at 220 nm; 10 min grad; Phenomenex AXIA 5u C18, 30×100 mm). The pure fractions were combined and concentrated. The resultant residue was dried in vacuo to provide the title compound (150 mg, 0.23 mmol, 54% yield) as a white solid. MS (ESI) m/z: 554.9 [M+H]$^+$ (Method B). $^1$H NMR (500 MHz, DMSO-d$_6$) δ 8.46-8.43 (m, 1H), 7.94-7.89 (m, 1H), 7.71-7.65 (m, 1H), 7.40-7.37 (m, 5H), 5.63-5.60 (m, 1H), 5.30-5.22 (m, 1H), 4.59-4.51 (m, 2H), 4.19-4.11 (m, 2H), 4.06-4.00 (m, 1H), 3.96-3.92 (m, 1H).

Step 2: Preparation of 5-((4aR,6S,7R,8R,8aR)-8-(4-(4-bromo-2,3-difluorophenyl)-1H-1,2,3-triazol-1-yl)-7-hydroxy-2-phenylhexahydropyrano[3,2-d][1,3]dioxin-6-yl)-4-(5-chloro-2-(trifluoromethyl)phenyl)-2,4-dihydro-3H-1,2,4-triazole-3-thione (mixture atropoisomer)

Step 2a: To a 100 pear shaped flask were added (4aR,6R,7R,8R,8aR)-8-(4-(4-bromo-2,3-difluorophenyl)-1H-1,2,3-triazol-1-yl)-7-hydroxy-2-phenylhexahydropyrano[3,2-d][1,3]dioxine-6-carbohydrazide (150 mg, 0.23 mmol), 4-chloro-2-isothiocyanato-1-(trifluoromethyl)benzene (63 mg, 0.270 mmol), and DMF (10 mL). The reaction was stirred. After 18 h, the reaction was diluted with water, and the resultant white ppt. was collected by vacuum filtration. Step 2b: The product of Step 2a was suspended in water (10 mL), and K$_2$CO$_3$ (1.0 g, 7.2 mmol) was added. The reaction was stirred vigorously at reflux. After 18 h, the reaction was cooled, diluted with water (100 mL), and extracted with EtOAc (2×50 mL). The organic phase was combined, washed with water, brine, dried over Na₂SO₄, filtered and concentrated. The residue was purified by preparative HPLC (4×2 mL injection; Method: Grad. Solv. System: From 20% A:80% B to 0% A:100% B; (A=10% MeCN/90% H₂O+ 0.1% TFA); (B=90% MeCN/10% H₂O+0.1% TFA); Detection at 220 nm; 10 min grad; Phenomenex AXIA 5u C18, 30×100 mm). The pure fractions were combined and concentrated. The resultant residue was dried in vacuo to afford the title compound (42 mg, 0.054 mmol, 23% yield) as a tan solid. MS (ESI) m/z: 774.1 [M+H]⁺ (Method B) (observed two closely eluting peaks with identical mass).

Step 3: Preparation of Example 26

To a 50 mL round bottomed flask were added 5-((4aR, 6S,7R,8R,8aR)-8-(4-(4-bromo-2,3-difluorophenyl)-1H-1,2, 3-triazol-1-yl)-7-hydroxy-2-phenylhexahydropyrano[3,2-d] [1,3]dioxin-6-yl)-4-(5-chloro-2-(trifluoromethyl)phenyl)-2, 4-dihydro-3H-1,2,4-triazole-3-thione (42 mg, 0.054 mmol) and DCM (3 mL). After cooling to 0° C., a solution of hydrogen peroxide (50% aq) (0.012 mL, 0.19 mmol) in AcOH (3 mL) was added dropwise. The reaction was then allowed to slowly reach rt and stirred. After 18 h, the reaction was cooled to 0° C., diluted with 1 N NaOH (50 mL) and extracted with EtOAc (2×25 mL). The organic phase was combined, washed with brine, dried over Na₂SO₄, filtered and concentrated. The resultant residue was purified by preparative HPLC (Column:)(Bridge C18, 200 mm×19 mm, 5-μm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 18% B, 18-58% B over 20 minutes, then a 4-minute hold at 100% B; Flow Rate: 20 mL/min; Column Temperature: 25 C. Fraction collection was triggered by MS signals). Fractions containing the desired product were combined and dried via centrifugal evaporation to afford the title compound (14 mg, 0.022 mmol, 41% yield). MS (ESI) m/z: 651.1 [M+H]⁺ (Method C). ¹H NMR (500 MHz, DMSO-d₆) δ 8.86-8.77 (m, 1H), 8.46-8.37 (m, 1H), 8.07-8.01 (m, 1H), 7.99-7.87 (m, 3H), 7.72-7.64 (m, 1H), 5.61-5.55 (m, 1H), 5.36-5.26 (m, 1H), 5.00-4.85 (m, 2H), 4.70-4.60 (m, 1H), 4.39-4.24 (m, 1H), 3.97-3.86 (m, 1H), 3.63-3.54 (m, 1H), 3.49-3.33 (m, 2H). hGal-3 IC₅₀=10 nM.

Example 27 and Example 28

5-((2S,3R,4R,5R,6R)-4-(4-(4-bromo-2,3-difluorophenyl)-1H-1,2,3-triazol-1-yl)-3,5-dihydroxy-6-(hydroxymethyl)tetrahydro-2H-pyran-2-yl)-4-(5-chloro-2-(trifluoromethyl)phenyl)-2,4-dihydro-3H-1,2,4-triazole-3-thione (single atropoisomer)

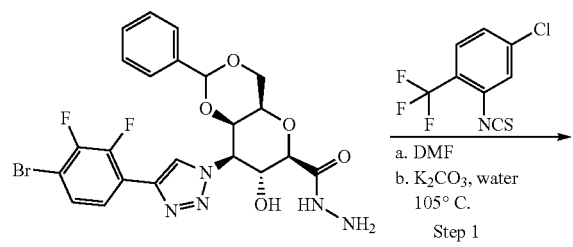

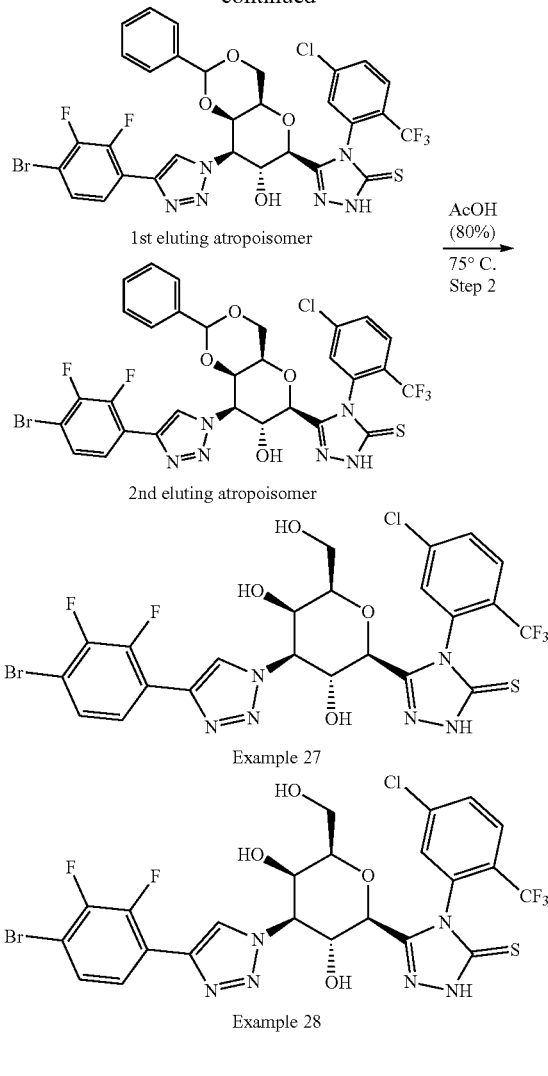

Step 1: Preparation of 5-((4aR,6S,7R,8R,8aR)-8-(4-(4-bromo-2,3-difluorophenyl)-1H-1,2,3-triazol-1-yl)-7-hydroxy-2-phenylhexahydropyrano[3,2-d][1,3] dioxin-6-yl)-4-(5-chloro-2-(trifluoromethyl)phenyl)-2,4-dihydro-3H-1,2,4-triazole-3-thione (single atropoisomer)

The mixture of atropoisomers were synthesized according to methods described for the synthesis of Example 26 (Step 2) starting from (4aR,6R,7R,8R,8aR)-8-(4-(4-bromo-2,3-difluorophenyl)-1H-1,2,3-triazol-1-yl)-7-hydroxy-2-phenylhexahydropyrano[3,2-d][1,3]dioxine-6-carbohydrazide (440 mg, 0.80 mmol). The atropoisomer mixture was separated by preparative HPLC (7×2 mL injection; Method: Grad. Solv. System: From 50% A:50% B to 0% A:100% B; (A=10% MeCN/90% H₂O+0.1% TFA); (B=90% MeCN/ 10% H₂O+0.1% TFA); Detection at 220 nm; 10 min grad; Phenomenex AXIA 5u C18, 30×100 mm). The respective pure fractions (1ˢᵗ and 2ⁿᵈ eluting) were combined and concentrated. The resultant residue was dried in vacuo to afford the respective pure atropoisomer:

1ˢᵗ eluting atropoisomer (110 mg, 0.14 mmol, 18% yield). MS (ESI) m/z: 772.7 [M+H]⁺ r.t.=1.06 min (Method B).

2<sup>nd</sup> eluting atropoisomer (90 mg, 0.12 mmol, 15% yield). MS (ESI) m/z: 772.7 [M+H]$^+$ r.t.=1.08 min (Method B).

Step 2: Preparation of Example 27 (Atropoisomer of Example 28)

To a 40 mL vial were added 5-((4aR,6S,7R,8R,8aR)-8-(4-(4-bromo-2,3-difluorophenyl)-1H-1,2,3-triazol-1-yl)-7-hydroxy-2-phenylhexahydropyrano[3,2-d][1,3]dioxin-6-yl)-4-(5-chloro-2-(trifluoromethyl)phenyl)-2,4-dihydro-3H-1,2,4-triazole-3-thione (1st eluting atropoisomer) (110 mg, 0.14 mmol) and AcOH (80%) (4 mL). The vial was capped and the reaction was stirred at 75° C. After 18 h, the solvent was concentrated and the residue was purified by preparative HPLC (Column: XBridge C18, 200 mm×19 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: a 0-minute hold at 21% B, 21-61% B over 20 minutes, then a 4-minute hold at 100% B; Flow Rate: 20 mL/min; Column Temperature: 25 C. Fraction collection was triggered by MS signals). Fractions containing the desired product were combined and dried via centrifugal evaporation to afford the title compound (36 mg, 0.053 mmol, 38% yield). MS (ESI) m/z: 682.8 [M+H]$^+$ r.t.=1.651 min (Method C). $^1$H NMR (500 MHz, DMSO-d$_6$) δ 8.45-8.40 (m, 1H), 8.07-8.02 (m, 1H), 7.97-7.93 (m, 1H), 7.93-7.88 (m, 1H), 7.70-7.63 (m, 1H), 7.60-7.55 (m, 1H), 5.71-5.63 (m, 1H), 5.40-5.31 (m, 1H), 5.00-4.89 (m, 1H), 4.73-4.64 (m, 1H), 4.60-4.49 (m, 1H), 4.18-4.11 (m, 1H), 3.97-3.85 (m, 1H). hGal-3 IC$_{50}$=76 nM.

Step 2: Preparation of Example 28 (atropoisomer of Example 27)

To a 40 mL vial were added 5-((4aR,6S,7R,8R,8aR)-8-(4-(4-bromo-2,3-difluorophenyl)-1H-1,2,3-triazol-1-yl)-7-hydroxy-2-phenylhexahydropyrano[3,2-d][1,3]dioxin-6-yl)-4-(5-chloro-2-(trifluoromethyl)phenyl)-2,4-dihydro-3H-1,2,4-triazole-3-thione (2nd eluting atropoisomer) (90 mg, 0.117 mmol) and AcOH (80%) (4 mL). The vial was capped and the reaction was stirred at 75° C. After 18 h, the solvent was concentrated and the residue was purified by preparative HPLC (Column: XBridge C18, 200 mm×19 mm, 5-μm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 17% B, 17-57% B over 20 minutes, then a 4-minute hold at 100% B; Flow Rate: 20 mL/min; Column Temperature: 25 C. Fraction collection was triggered by MS signals). Fractions containing the desired product were combined and dried via centrifugal evaporation to afford the title compound (29 mg, 0.042, 35% yield). MS (ESI) m/z: 683.1 [M+H]$^+$ r.t.=1.618 min (Method C). $^1$H NMR (500 MHz, DMSO-d$_6$) δ 8.32 (d, J=3.1 Hz, 1H), 8.00-7.96 (m, 1H), 7.95-7.88 (m, 2H), 7.78 (d, J=1.8 Hz, 1H), 7.65 (s, 1H), 5.75-5.65 (m, 1H), 5.24-5.17 (m, 1H), 4.93-4.84 (m, 1H), 4.64-4.56 (m, 1H), 4.28-4.19 (m, 1H), 3.87-3.80 (m, 1H), 3.58-3.49 (m, 1H), 3.31-3.23 (m, 2H). hGal-3 IC$_{50}$=6.9 nM.

Example 29

(2R,3R,4S,5R,6S)-4-(4-(4-bromo-2,3-difluorophenyl)-1H-1,2,3-triazol-1-yl)-6-(4-(5-chloro-2-(trifluoromethyl)phenyl)-4H-1,2,4-triazol-3-yl)-5-(2,2-difluoroethoxy)-2-(hydroxymethyl)tetrahydro-2H-pyran-3-ol

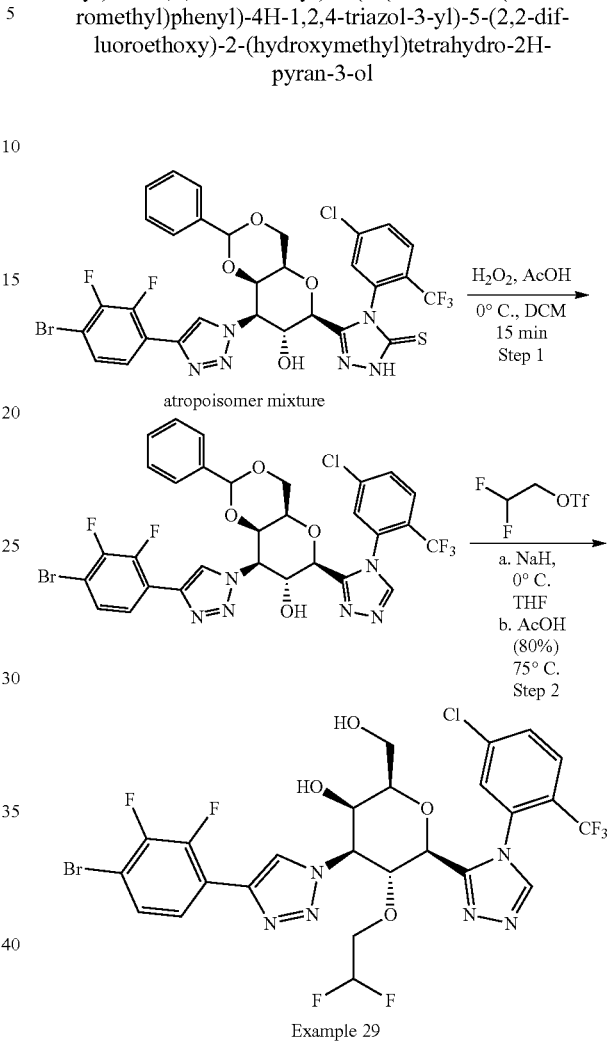

Example 29

Step 1: Preparation of (4aR,6S,7R,8R,8aR)-8-(4-(4-bromo-2,3-difluorophenyl)-1H-1,2,3-triazol-1-yl)-6-(4-(5-chloro-2-(trifluoromethyl)phenyl)-4H-1,2,4-triazol-3-yl)-2-phenylhexahydropyrano[3,2-d][1,3]dioxin-7-ol To a 50 mL round bottomed flask were added 5-((4aR,6S,7R,8R,8aR)-8-(4-(4-bromo-2,3-difluorophenyl)-1H-1,2,3-triazol-1-yl)-7-hydroxy-2-phenylhexahydropyrano[3,2-d][1,3]dioxin-6-yl)-4-(5-chloro-2-(trifluoromethyl)phenyl)-2,4-dihydro-3H-1,2,4-triazole-3-thione (atropoisomer mixture) (210 mg, 0.27 mmol) and DCM (5 mL). After cooling to 0° C., a solution of hydrogen peroxide (50% aq) (0.12 mL, 1.9 mmol) in AcOH (5 mL) was added dropwise. After stirring at this temperature for 15 min, the reaction was quenched with 1 M NaOH (50 mL) and extracted with EtOAc (2×25 mL). The organic phase was combined, washed with brine, dried over Na$_2$SO$_4$, filtered and concentrated. The product was dried in vacuo to afford the title compound (200 mg, 0.27 mmol, 99% yield) as an off white solid. MS (ESI) m/z: 740.5 [M+H]$^+$ (Method B). $^1$H NMR (500 MHz, DMSO-d$_6$) δ 8.89-8.80 (m, 1H), 8.48-8.29 (m, 1H), 8.00-7.85 (m, 3H), 7.74-7.64 (m, 2H), 7.44-7.34 (m, 5H), 5.78-5.67 (m, 1H), 5.59-5.47 (m, 1H), 5.35-5.25 (m, 1H), 4.80-4.67 (m, 2H), 4.49-4.43 (m, 1H), 4.09-4.02 (m, 1H), 3.99-3.89 (m, 1H), 3.86-3.77 (m, 1H).

Step 2: Preparation of Example 29

Step 2a: To a 25 mL pear shaped flask were added (4aR,6S,7R,8R,8aR)-8-(4-(4-bromo-2,3-difluorophenyl)-1H-1,2,3-triazol-1-yl)-6-(4-(5-chloro-2-(trifluoromethyl)phenyl)-4H-1,2,4-triazol-3-yl)-2-phenylhexahydropyrano[3,2-d][1,3]dioxin-7-ol (60 mg, 0.081 mmol) and THF (5 mL). The reaction was cooled to 0° C., then sodium hydride (60% dispersion in mineral oil) (27 mg, 0.68 mmol) was added. The reaction was stirred at the above temperature for 20 min, then 2,2-difluoroethyl trifluoromethanesulfonate (0.089 mL, 0.68 mmol) was added dropwise over a period of 5 min. The reaction was continued at 0° C. After 1.5 h, the reaction was diluted with sat. NH$_4$Cl (100 mL) and extracted with EtOAc (2×50 mL). The organic phase was combined, washed with brine, dried over Na$_2$SO$_4$, filtered and concentrated. The residue was purified by flash column chromatography (12 g silica gel cartridge; A=Hex, B=EtOAc; 10 min grad.; 0% B to 100% B; flow rate=8 mL/min). The pure fractions were combined, concentrated and dried in vacuo.

Step 2b: The product of Step 2a was dissolved in 80% AcOH (4 mL) and stirred at 75° C. After 30 h, the solvent was concentrated and the resultant residue was dissolved in THF (2 mL) and 1 M NaOH (2 mL) and the vial was vigorously stirred. After 30 min, the reaction was diluted with 5% citric acid (15 mL) and partitioned with EtOAc (15 mL). The layers were separated, the aqueous phase was extracted with EtOAc, the organic phase was combined, washed with brine, dried over MgSO$_4$, filtered and concentrated. The residue was purified by preparative HPLC (Column:)(Bridge C18, 200 mm×19 mm, 5-μm particles; Mobile Phase A: 5:95 acetonitrile:water with ammonium acetate; Mobile Phase B: 95:5 acetonitrile:water with ammonium acetate; Gradient: a 0-minute hold at 30% B, 30-70% B over 20 minutes, then a 0-minute hold at 100% B; Flow Rate: 20 mL/min; Column Temperature: 25 C. Fraction collection was triggered by MS and UV signals). Fractions containing the desired product were combined and dried via centrifugal evaporation to afford the title compound (23 mg, 0.032 mmol, 40% yield). MS (ESI) m/z: 715.1 [M+H]$^+$ (Method C). $^1$H NMR (500 MHz, DMSO-d$_6$) δ 8.90 (s, 1H), 8.80 (d, J=2.7 Hz, 1H), 8.05 (d, J=8.5 Hz, 1H), 7.99-7.85 (m, 2H), 7.66 (s, 2H), 5.56-5.50 (m, 2H), 5.16-5.05 (m, 2H), 4.83-4.76 (m, 1H), 4.38-4.28 (m, 1H), 3.97-3.91 (m, 1H), 3.63-3.56 (m, 1H), 3.48-3.35 (m, 2H). hGal-3 IC$_{50}$=11 nM.

Examples 30 to 65 in the table below were synthesized according to methods described for Examples 26 to 29, using appropriate starting materials.

| EX # | Structure | LCMS (Method C, unless otherwise indicated)/$^1$H NMR (500 MHz, DMSO-d$_6$, unless otherwise indicated) | hGal-3 IC$_{50}$ (nM) |
|---|---|---|---|
| 30 | 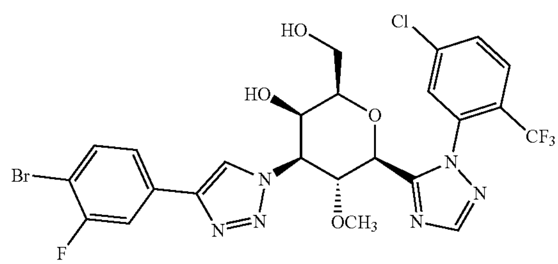 [SMILES: CO[C@@H]1[C@@H](n2cc(-c3ccc(Br)c(F)c3)nn2)[C@@H](O)[C@@H](CO)O[C@H]1c1ncnn1-c1cc(Cl)ccc1C(F)(F)F] | MS (ESI) m/z: 647.2. δ 9.01 (s, 1H), 8.88 (s, 1H), 8.05 (d, J = 8.6 Hz, 1H), 7.88 (s, 3H), 7.78 (br d, J = 7.1 Hz, 2H), 5.53-5.46 (m, 1H), 5.07-4.93 (m, 1H), 4.86-4.77 (m, 1H), 4.73-4.34 (m, 1H), 4.27-4.13 (m, 1H), 3.93-3.84 (m, 1H), 3.70 (s, 3H), 3.49-3.38 (m, 1H) | 22 |
| 31 | 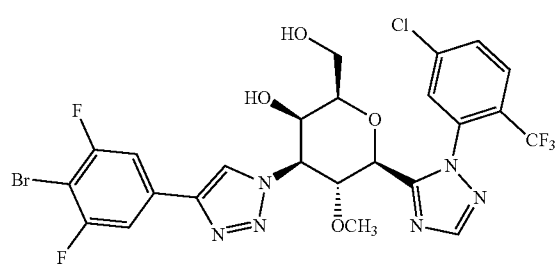 [SMILES: CO[C@@H]1[C@@H](n2cc(-c3cc(F)c(Br)c(F)c3)nn2)[C@@H](O)[C@@H](CO)O[C@H]1c1ncnn1-c1cc(Cl)ccc1C(F)(F)F] | MS (ESI) m/z: 665.0. δ 9.17-9.06 (m, 1H), 8.91-8.80 (m, 1H), 8.09-8.01 (m, 1H), 8.00-7.93 (m, 1H), 7.91-7.88 (m, 1H), 7.87-7.80 (m, 2H), 5.50-5.37 (m, 1H), 5.12-4.97 (m, 1H), 4.85-4.74 (m, 1H), 4.57-4.39 (m, 1H), 4.28-4.14 (m, 1H), 3.92-3.82 (m, 1H), 3.64-3.56 (m, 1H), 3.47 (s, 3H) | 24 |
| 32 | 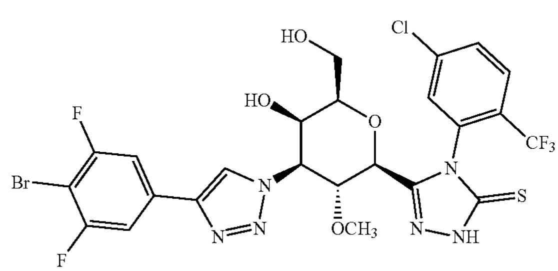 | MS (ESI) m/z: 696.9. δ 9.05 (s, 1H), 8.08-8.00 (m, 1H), 7.97-7.91 (m, 1H), 7.85-7.78 (m, 2H), 7.77-7.71 (m, 1H), 5.55-5.39 (m, 1H), 5.09-4.94 (m, 1H), 4.75-4.64 (m, 1H), 4.62-4.50 (m, 1H), 4.18-4.05 (m, 1H), 3.85-3.73 (m, 1H), 3.41-3.29 (m, 1H), 3.05 (s, 3H) | 20 |

Atropoisomer of Example 33

| EX # | Structure | LCMS (Method C, unless otherwise indicated)/¹H NMR (500 MHz, DMSO-d$_6$, unless otherwise indicated) | hGal-3 IC$_{50}$ (nM) |
|---|---|---|---|
| 33 | Atropoisomer of Example 32 | MS (ESI) m/z: 696.9. δ 9.08-9.03 (m, 1H), 8.04 (br d, J = 8.5 Hz, 1H), 7.99-7.93 (m, 1H), 7.80 (br d, J = 8.2 Hz, 1H), 7.61 (s, 1H), 5.53-5.46 (m, 1H), 5.09-5.02 (m, 1H), 4.48-4.35 (m, 1H), 4.29-4.18 (m, 1H), 3.92-3.82 (m, 1H), 3.57-3.51 (m, 2H), 2.99 (s, 3H) | 290 |
| 34 | 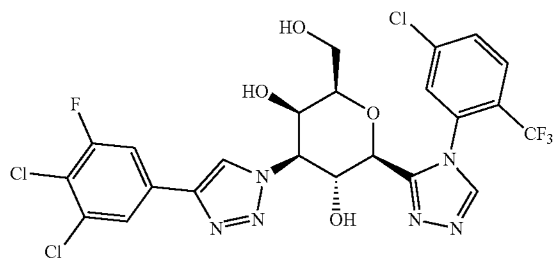 [SMILES: OC[C@H]1O[C@@H](c2nncn2-c2cc(Cl)ccc2C(F)(F)F)[C@H](O)[C@@H](n2cc(-c3cc(F)c(Cl)c(Cl)c3)nn2)[C@H]1O] | MS (ESI) m/z: 622.8. δ 8.92-8.87 (m, 1H), 8.87-8.79 (m, 1H), 8.09-8.03 (m, 2H), 7.99-7.93 (m, 2H), 7.92-7.67 (m, 1H), 5.56-5.47 (m, 1H), 5.45-5.31 (m, 1H), 5.01-4.85 (m, 2H), 4.80-4.63 (m, 2H), 4.38-4.15 (m, 1H), 3.97-3.86 (m, 1H) | 20 |
| 35 | 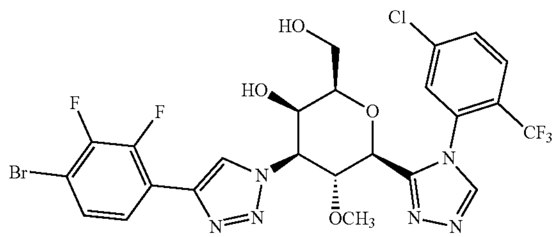 [SMILES: CO[C@@H]1[C@@H](n2cc(-c3ccc(Br)c(F)c3F)nn2)[C@@H](O)[C@@H](CO)O[C@H]1c1nncn1-c1cc(Cl)ccc1C(F)(F)F] | MS (ESI) m/z: 665.3. δ 8.88-8.80 (m, 1H), 8.68 (br d, J = 2.4 Hz, 1H), 8.03 (s, 1H), 7.95 (br s, 1H), 7.86 (br s, 2H), 7.70-7.60 (m, 1H), 5.58-5.49 (m, 1H), 5.12-4.96 (m, 1H), 4.84-4.73 (m, 1H), 4.54-4.35 (m, 1H), 4.27-4.16 (m, 1H), 3.96-3.87 (m, 1H), 3.61-3.54 (m, 1H), 2.97 (s, 3H) | 9.3 |
| 36 | 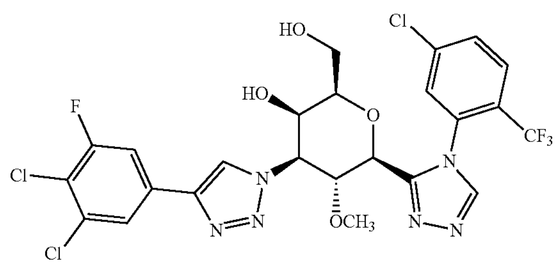 [SMILES: CO[C@@H]1[C@@H](n2cc(-c3cc(F)c(Cl)c(Cl)c3)nn2)[C@@H](O)[C@@H](CO)O[C@H]1c1nncn1-c1cc(Cl)ccc1C(F)(F)F] | MS (ESI) m/z: 638.1. δ 9.19-9.11 (m, 1H), 8.89 (s, 1H), 8.13 (s, 1H), 8.06 (d, J = 8.5 Hz, 1H), 8.03-7.94 (m, 2H), 7.91 (s, 1H), 5.49-5.06 (m, 1H), 5.06-4.99 (m, 1H), 4.86-4.73 (m, 1H), 4.62-4.35 (m, 1H), 4.28-4.20 (m, 1H), 3.92-3.85 (m, 1H), 3.65-3.53 (m, 1H), 3.04 (s, 3H). | 35 |
| 37 | 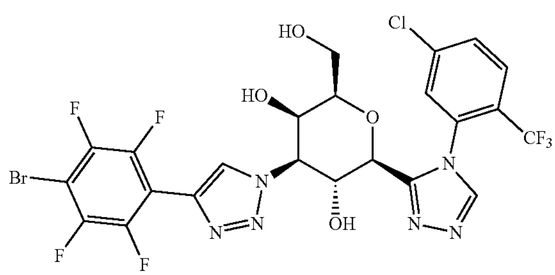 [SMILES: OC[C@H]1O[C@@H](c2nncn2-c2cc(Cl)ccc2C(F)(F)F)[C@H](O)[C@@H](n2cc(-c3c(F)c(F)c(Br)c(F)c3F)nn2)[C@H]1O] | MS (ESI) m/z: 687.2. δ 8.82 (d, J = 18.0 Hz, 1H), 8.53-8.44 (m, 1H), 8.07-8.01 (m, 1H), 7.93 (s, 1H), 7.89 (s, 1H), 5.69-5.33 (m, 1H), 5.02-4.95 (m, 1H), 4.95-4.60 (m, 1H), 4.41-4.23 (m, 1H), 4.01-3.91 (m, 1H), 3.71-3.56 (m, 1H), 3.43-3.36 (m, 1H). | 5.7 |

| EX # | Structure | LCMS (Method C, unless otherwise indicated)/¹H NMR (500 MHz, DMSO-d₆, unless otherwise indicated) | hGal-3 IC₅₀ (nM) |
|---|---|---|---|
| 38 | (structure) | MS (ESI) m/z: 667.2. δ 8.87 (s, 1H), 8.43 (d, J = 3.1 Hz, 1H), 7.91 (s, 2H), 7.88-7.82 (m, 1H), 7.79-7.73 (m, 1H), 7.71-7.63 (m, 1H), 5.65-5.54 (m, 1H), 5.36-5.28 (m, 1H), 5.04-4.96 (m, 1H), 4.89-4.77 (m, 1H), 4.74-4.66 (m, 1H), 4.45-4.33 (m, 1H), 4.02-3.94 (m, 1H), 3.79-3.66 (m, 1H). | 11 |
| 39 | (structure) Atropoisomer of Example 40 | MS (ESI) m/z: 719.2. δ 8.15 (s, 1H), 8.04 (s, 1H), 7.96 (s, 1H), 7.59 (s, 1H), 5.68-5.61 (m, 1H), 5.37-5.31 (m, 1H), 5.03-4.96 (m, 1H), 4.68-4.61 (m, 1H), 4.60-4.52 (m, 1H), 4.20-4.11 (m, 1H), 3.98-3.88 (m, 1H), 3.65-3.56 (m, 1H). | 160 |
| 40 | (structure) Atropoisomer of Example 39 | MS (ESI) m/z: 719.2. δ 8.43-8.37 (m, 1H), 8.01-7.98 (m, 1H), 7.97-7.93 (m, 1H), 7.84-7.78 (m, 1H), 5.74-5.60 (m, 1H), 5.25-5.06 (m, 1H), 5.02-4.93 (m, 1H), 4.70-4.52 (m, 2H), 4.30-4.22 (m, 1H), 3.93-3.80 (m, 1H), 3.35-3.16 (m, 1H). | 6.9 |
| 41 | (structure) Atropoisomer of Example 42 | MS (ESI) m/z: 735.0. δ 8.47-8.41 (m, 1H), 7.96 (s, 1H), 7.85-7.81 (m, 1H), 7.69-7.62 (m, 1H), 5.76-5.24 (m, 1H), 5.04-4.97 (m, 1H), 4.75-4.62 (m, 1H), 4.26-4.18 (m, 1H), 3.97-3.84 (m, 1H), 3.69-3.59 (m, 1H), 2.96-2.91 (m, 1H). | 10 |
| 42 | (structure) Atropoisomer of Example 41 | MS (ESI) m/z: 735.1. δ 8.50-8.45 (m, 1H), 7.97-7.95 (m, 1H), 7.85-7.80 (m, 1H), 7.67-7.62 (m, 1H), 5.72-5.31 (m, 1H), 5.08-4.99 (m, 1H), 4.60-4.49 (m, 1H), 4.29-4.41 (m, 1H), 3.97-3.92 (m, 1H), 3.91-3.84 (m, 1H), 3.67-3.57 (m, 1H). | 63 |

| EX # | Structure | LCMS (Method C, unless otherwise indicated)/¹H NMR (500 MHz, DMSO-d$_6$, unless otherwise indicated) | hGal-3 IC$_{50}$ (nM) |
|---|---|---|---|
| 43 | Atropoisomer of Example 44 | MS (ESI) m/z: 712.8. δ 8.76-8.60 (m, 1H), 7.96 (s, 1H), 7.94-7.88 (m, 1H), 7.87-7.84 (m, 1H), 7.84-7.77 (m, 1H), 7.67 (s, 1H), 5.52-5.38 (m, 1H), 5.18-5.07 (m, 1H), 4.67-4.57 (m, 1H), 4.49-4.31 (m, 1H), 4.16 (d, J = 9.4 Hz, 1H), 3.95-3.83 (m, 1H), 3.67-3.56 (m, 1H). | 18 |
| 44 | Atropoisomer of Example 43 | MS (ESI) m/z: 713.0. δ 8.74-8.57 (m, 1H), 7.97-7.93 (m, 1H), 7.93-7.88 (m, 1H), 7.87-7.79 (m, 1H), 7.77-7.64 (m, 2H), 5.15-5.04 (m, 1H), 4.67-4.54 (m, 1H), 4.46-4.30 (m, 1H), 4.17-4.10 (m, 1H), 3.92-3.86 (m, 1H), 3.57-3.33 (m, 1H), 3.23-3.05 (m, 1H). | 12 |
| 45 | Atropoisomer of Example 46 | MS (ESI) m/z: 655.0. δ 8.38-8.32 (m, 1H), 8.01-7.93 (m, 1H), 7.85-7.82 (m, 1H), 7.82-7.79 (m, 1H), 7.66-7.63 (m, 1H), 7.60-7.54 (m, 1H), 5.77-5.21 (m, 1H), 4.99-4.91 (m, 1H), 4.71-4.59 (m, 1H), 4.24-4.18 (m, 1H), 3.93-3.84 (m, 1H), 3.66-3.42 (m, 1H), 3.41-3.28 (m, 1H). | 8 |
| 46 | Atropoisomer of Example 45 | MS (ESI) m/z: 655.3. δ 8.42-8.34 (m, 1H), 8.00-7.90 (m, 1H), 7.86-7.77 (m, 1H), 7.72-7.66 (m, 1H), 7.66-7.62 (m, 1H), 7.59-7.53 (m, 1H), 5.74-5.30 (m, 1H), 5.04-4.92 (m, 1H), 4.58-4.47 (m, 1H), 4.29-4.19 (m, 1H), 3.96-3.89 (m, 1H), 3.59-3.49 (m, 2H), 3.47-3.41 (m, 1H), 3.34-3.24 (m, 1H). | 74 |
| 47 | 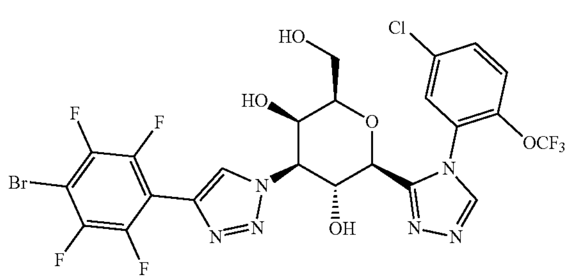 | MS (ESI) m/z: 703.2. δ 8.89-8.82 (m, 1H), 8.53-8.46 (m, 1H), 7.91-7.87 (m, 1H), 7.86-7.82 (m, 1H), 7.78-7.72 (m, 1H), 5.68-5.32 (m, 1H), 5.09-4.98 (m, 1H), 4.88-4.77 (m, 1H), 4.46-4.34 (m, 1H), 4.03-3.88 (m, 1H), 3.76-3.65 (m, 1H), 3.51-3.33 (m, 1H). | 14 |

-continued

| EX # | Structure | LCMS (Method C, unless otherwise indicated)/$^1$H NMR (500 MHz, DMSO-$d_6$, unless otherwise indicated) | hGal-3 IC$_{50}$ (nM) |
|---|---|---|---|
| 48 | 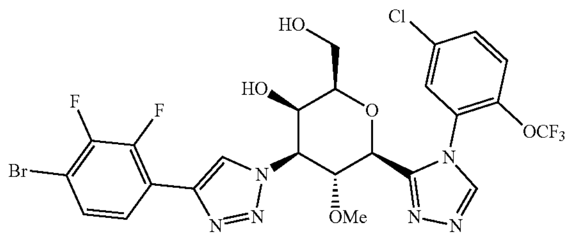 | MS (ESI) m/z: 681.1 [M + H]$^+$ 8.95-8.89 (m, 1H), 8.72-8.66 (m, 1H), 7.97-7.89 (m, 2H), 7.88-7.82 (m, 1H), 7.80-7.74 (m, 1H), 7.72-7.63 (m, 1H), 5.58-5.33 (m, 1H), 5.20-5.09 (m, 1H), 4.84-4.66 (m, 1H), 4.51-4.34 (m, 1H), 3.98-3.92 (m, 1H), 3.79-3.67 (m, 1H), 3.51-3.30 (m, 1H), 2.97 (s, 3H). | 14 |
| 49 | Atropoisomer of Example 50 | MS (ESI) m/z: 639.2. δ 8.46-8.38 (m, 1H), 8.08-8.03 (m, 1H), 7.96 (s, 2H), 7.61-7.54 (m, 2H), 5.71-5.30 (m, 1H), 5.02-4.90 (m, 1H), 4.61-4.50 (m, 1H), 4.21-4.11 (m, 1H), 3.97-3.86 (m, 1H), 3.65-3.53 (m, 1H), 3.37-3.24 (m, 1H). | 140 |
| 50 | Atropoisomer of Example 49 | MS (ESI) m/z: 639.2. δ 8.39-8.30 (m, 1H), 8.02-7.91 (m, 3H), 7.84-7.78 (m, 1H), 7.60-7.52 (m, 1H), 5.73-5.16 (m, 1H), 4.96-4.90 (m, 1H), 4.67-4.54 (m, 1H), 4.31-4.23 (m, 1H), 3.88-3.80 (m, 1H), 3.59-3.45 (m, 1H), 3.31-3.22 (m, 1H). | 8.7 |
| 51 | 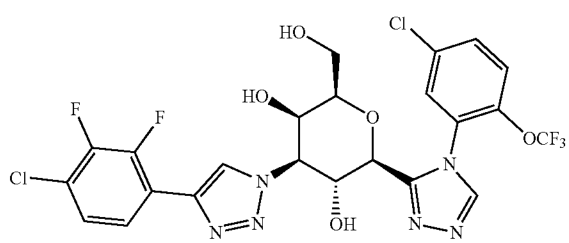 [SMILES: OC[C@H]1O[C@@H](c2nncn2-c2cc(Cl)ccc2OC(F)(F)F)[C@H](O)[C@@H](n2cc(-c3ccc(Br)c(F)c3F)nn2)[C@H]1O] | MS (ESI) m/z: 623.1. δ 8.86 (s, 1H), 8.46-8.39 (m, 1H), 7.98 (s, 1H), 7.91 (d, J = 2.1 Hz, 1H), 7.86-7.81 (m, 1H), 7.76 (s, 1H), 7.62-7.52 (m, 1H), 5.65-5.30 (m, 1H), 5.05-4.95 (m, 1H), 4.89-4.76 (m, 1H), 4.47-4.31 (m, 1H), 4.04-3.91 (m, 1H), 3.76-3.67 (m, 1H), 3.48-3.38 (m, 1H). | 14 |
| 52 | 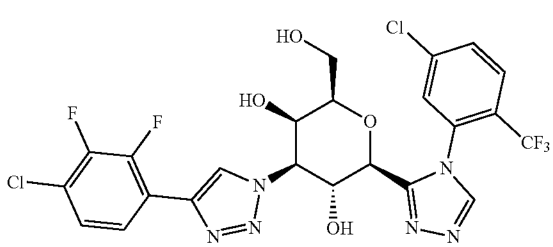 [SMILES: OC[C@H]1O[C@@H](c2nncn2-c2cc(Cl)ccc2C(F)(F)F)[C@H](O)[C@@H](n2cc(-c3ccc(Cl)c(F)c3F)nn2)[C@H]1O] | MS (ESI) m/z: 606.8. δ 8.88-8.79 (m, 1H), 8.48-8.38 (m, 1H), 8.09-8.03 (m, 1H), 8.02-7.95 (m, 2H), 7.94-7.70 (m, 1H), 7.58 (br t, J = 7.8 Hz, 1H), 5.64-5.25 (m, 1H), 5.05-4.86 (m, 2H), 4.73-4.59 (m, 1H), 4.43-4.27 (m, 1H), 3.94 (br d, J = 5.8 Hz, 1H), 3.61 (br s, 1H). | 9.7 |

| EX # | Structure | LCMS (Method C, unless otherwise indicated)/¹H NMR (500 MHz, DMSO-d₆, unless otherwise indicated) | hGal-3 IC₅₀ (nM) |
|---|---|---|---|
| 53 | 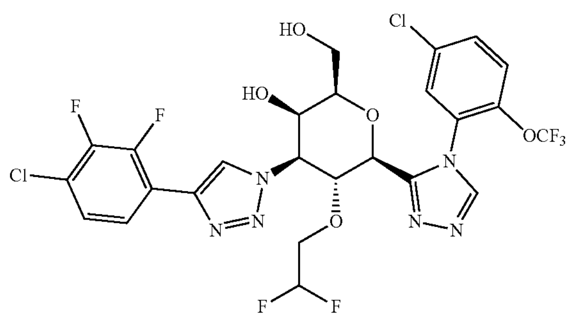 [SMILES: OC[C@H]1O[C@@H](c2nncn2-c2cc(Cl)ccc2OC(F)(F)F)[C@H](OCC(F)F)[C@@H](n2cc(-c3ccc(Cl)c(F)c3F)nn2)[C@H]1O] | MS (ESI) m/z: 687.2. δ 8.94 (s, 1H), 8.81 (d, J = 2.7 Hz, 1H), 7.93 (br s, 2H), 7.85 (br d, J = 2.7 Hz, 1H), 7.78 (s, 1H), 7.61-7.53 (m, 1H), 5.60-5.32 (m, 2H), 5.27-5.20 (m, 1H), 5.09-4.99 (m, 1H), 4.90-4.72 (m, 1H), 4.55-4.45 (m, 1H), 4.03-3.96 (m, 1H), 3.81-3.71 (m, 1H), 3.58-3.26 (m, 1H) (one proton obscured). | 19 |
| 54 | 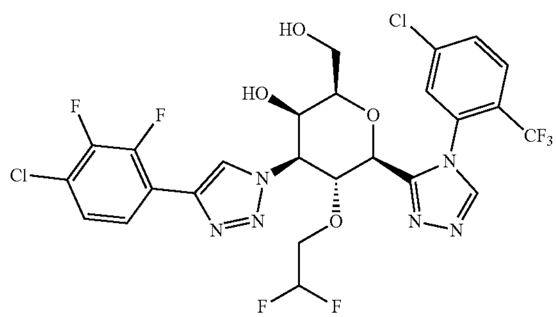 [SMILES: OC[C@H]1O[C@@H](c2nncn2-c2cc(Cl)ccc2C(F)(F)F)[C@H](OCC(F)F)[C@@H](n2cc(-c3ccc(Cl)c(F)c3F)nn2)[C@H]1O] | MS (ESI) m/z: 671.2. δ 8.94-8.91 (m, 1H), 8.86-8.83 (m, 1H), 8.10-8.06 (m, 1H), 8.02-7.92 (m, 3H), 7.61-7.54 (m, 1H), 5.61-5.43 (m, 2H), 5.37-5.22 (m, 1H), 5.22-5.15 (m, 1H), 5.14-5.06 (m, 1H), 4.98-4.70 (m, 1H), 4.43-4.35 (m, 1H), 3.98-3.91 (m, 1H), 3.84-3.72 (m, 1H), 3.68-3.60 (m, 1H). | 12 |
| 55 | 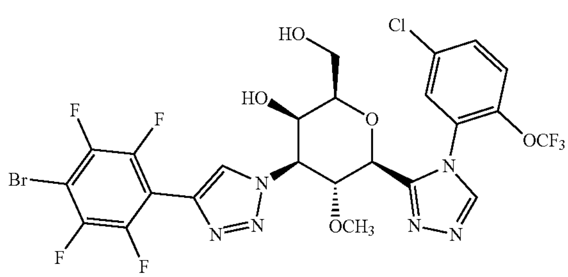 [SMILES: CO[C@@H]1[C@@H](n2cc(-c3c(F)c(F)c(Br)c(F)c3F)nn2)[C@@H](O)[C@@H](CO)O[C@H]1c1nncn1-c1cc(Cl)ccc1OC(F)(F)F] | MS (ESI) m/z: 717.0. δ 8.96-8.89 (m, 1H), 8.81-8.75 (m, 1H), 7.95-7.93 (m, 1H), 7.88-7.83 (m, 1H), 7.79-7.74 (m, 1H), 5.56-5.42 (m, 1H), 5.22-5.12 (m, 1H), 4.85-4.65 (m, 1H), 4.49-4.38 (m, 1H), 3.99-3.92 (m, 1H), 3.78-3.67 (m, 1H), 3.59-3.43 (m, 1H), 2.93 (s, 3H). | 11 |
| 56 | 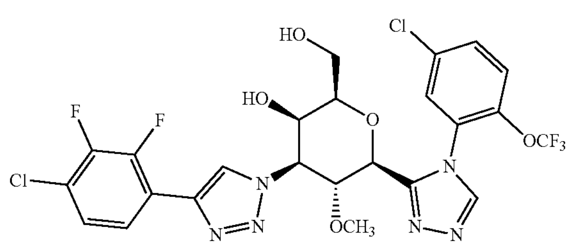 [SMILES: CO[C@@H]1[C@@H](n2cc(-c3ccc(Cl)c(F)c3F)nn2)[C@@H](O)[C@@H](CO)O[C@H]1c1nncn1-c1cc(Cl)ccc1OC(F)(F)F] | MS (ESI) m/z: 637.2. δ 8.91 (s, 1H), 8.68 (d, J = 2.4 Hz, 1H), 7.97-7.91 (m, 2H), 7.89-7.83 (m, 1H), 7.80-7.73 (m, 1H), 7.60-7.52 (m, 1H), 5.53-5.42 (m, 1H), 5.15-5.08 (m, 1H), 4.80-4.64 (m, 1H), 4.47-4.36 (m, 1H), 3.98-3.91 (m, 1H), 3.77-3.66 (m, 1H), 3.53-3.39 (m, 1H), 2.91 (s, 3H). | 11 |
| 57 | 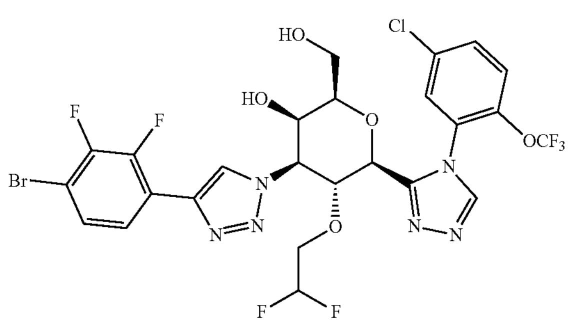 [SMILES: OC[C@H]1O[C@@H](c2nncn2-c2cc(Cl)ccc2OC(F)(F)F)[C@H](OCC(F)F)[C@@H](n2cc(-c3ccc(Br)c(F)c3F)nn2)[C@H]1O] | MS (ESI) m/z: 732.5 (Method B). ¹H NMR (500 MHz, METHANOL-d₄) δ 8.86 (s, 1H), 8.68 (d, J = 3.3 Hz, 1H), 7.98-7.93 (m, 1H), 7.93-7.88 (m, 1H), 7.83-7.78 (m, 1H), 7.72-7.66 (m, 1H), 7.60-7.53 (m, 1H), 5.50-5.21 (m, 1H), 5.15-5.00 (m, 2H), 4.60-4.51 (m, 1H), 4.21-4.12 (m, 1H), 3.83-3.77 (m, 1H), 3.76-3.58 (m, 3H) (one proton obscured). | 21 |

-continued

| EX # | Structure | LCMS (Method C, unless otherwise indicated)/¹H NMR (500 MHz, DMSO-d₆, unless otherwise indicated) | hGal-3 IC₅₀ (nM) |
|---|---|---|---|
| 58 | 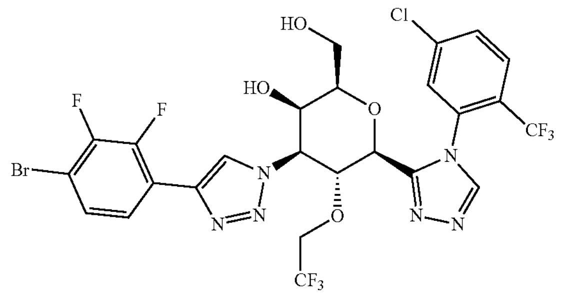 | MS (ESI) m/z: 733.1. δ 8.94-8.91 (m, 1H), 8.87-8.85 (m, 1H), 8.09-8.05 (m, 1H), 7.98-7.93 (m, 2H), 7.92-7.87 (m, 1H), 7.70-7.66 (m, 1H), 5.58-5.49 (m, 1H), 5.27-5.16 (m, 2H), 4.79-4.72 (m, 1H), 4.63-4.58 (m, 1H), 4.47-4.39 (m, 1H), 4.14-4.02 (m, 1H), 3.99-3.93 (m, 1H), 3.85-3.73 (m, 1H). | 14 |
| 59 | 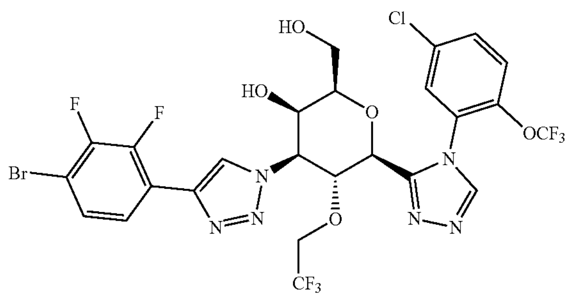 [SMILES: OC[C@H]1O[C@@H](c2nncn2-c2cc(Cl)ccc2OC(F)(F)F)[C@H](OCC(F)(F)F)[C@@H](n2cc(-c3ccc(Br)c(F)c3F)nn2)[C@H]1O] | MS (ESI) m/z: 750.4 (Method B). ¹H NMR (400 MHz, METHANOL-d₄) δ 8.86 (s, 1H), 8.68 (d, J = 3.3 Hz, 1H), 7.96 (s, 1H), 7.93-7.87 (m, 1H), 7.83-7.78 (m, 1H), 7.72-7.67 (m, 1H), 7.60-7.53 (m, 1H), 5.26-5.18 (m, 1H), 5.17-5.12 (m, 1H), 4.60-4.50 (m, 1H), 4.21-4.14 (m, 1H), 4.08-3.96 (m, 1H), 3.85-3.78 (m, 1H), 3.77-3.56 (m, 3H). | 57 |
| 60 | 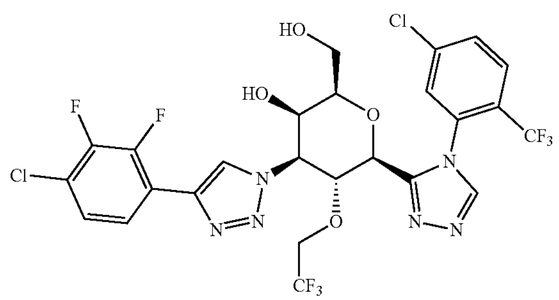 [SMILES: OC[C@H]1O[C@@H](c2nncn2-c2cc(Cl)ccc2C(F)(F)F)[C@H](OCC(F)(F)F)[C@@H](n2cc(-c3ccc(Cl)c(F)c3F)nn2)[C@H]1O] | MS (ESI) m/z: 689.0. δ 8.95-8.91 (m, 1H), 8.88-8.86 (m, 1H), 8.10-8.05 (m, 1H), 7.99-7.92 (m, 3H), 7.60-7.53 (m, 1H), 5.56-5.50 (m, 1H), 5.25-5.18 (m, 2H), 4.77-4.70 (m, 1H), 4.65-4.55 (m, 1H), 4.46-4.39 (m, 1H), 4.14-4.04 (m, 1H), 3.99-3.93 (m, 1H), 3.86-3.73 (m, 1H). | 14 |
| 61 | 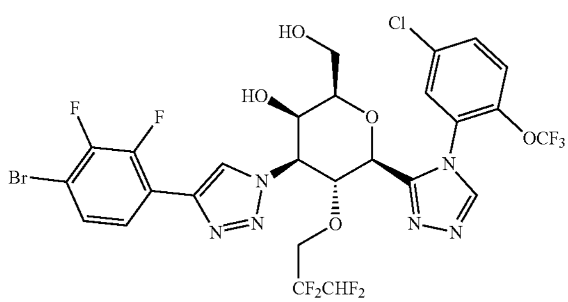 | MS (ESI) m/z: 780.9. δ 8.96 (s, 1H), 8.86-8.83 (m, 1H), 7.96-7.93 (m, 1H), 7.92-7.84 (m, 2H), 7.81-7.76 (m, 1H), 7.71-7.64 (m, 1H), 6.01-5.77 (m, 1H), 5.62-5.49 (m, 1H), 5.30-5.22 (m, 1H), 5.19-5.07 (m, 1H), 4.82-4.70 (m, 1H), 4.59-4.48 (m, 1H), 4.00-3.94 (m, 2H), 3.83-3.70 (m, 1H) (one proton obscured). | 49 |
| 62 | 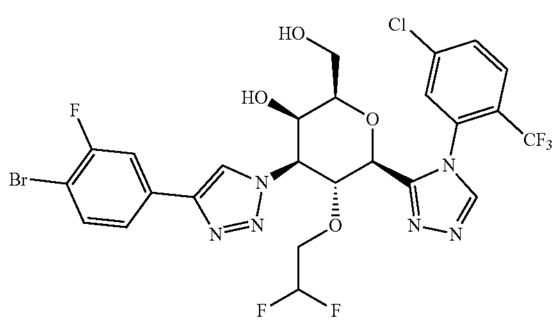 [SMILES: OC[C@H]1O[C@@H](c2nncn2-c2cc(Cl)ccc2C(F)(F)F)[C@H](OCC(F)F)[C@@H](n2cc(-c3ccc(Br)c(F)c3)nn2)[C@H]1O] | MS (ESI) m/z: 697.1. δ 9.13 (s, 1H), 8.93 (s, 1H), 8.07 (s, 1H), 8.02-7.87 (m, 3H), 7.85-7.80 (m, 1H), 7.78-7.72 (m, 1H), 5.60-5.31 (m, 1H), 5.24-5.11 (m, 1H), 5.08-5.01 (m, 1H), 4.91-4.76 (m, 1H), 4.38 (d, J = 9.1 Hz, 1H), 3.94-3.86 (m, 1H), 3.85-3.72 (m, 1H), 3.71-3.55 (m, 1H), 3.54-3.37 (m, 1H) (one proton obscured). | 40 |

| EX # | Structure | LCMS (Method C, unless otherwise indicated)/$^1$H NMR (500 MHz, DMSO-$d_6$, unless otherwise indicated) | hGal-3 IC$_{50}$ (nM) |
|---|---|---|---|
| 63 | 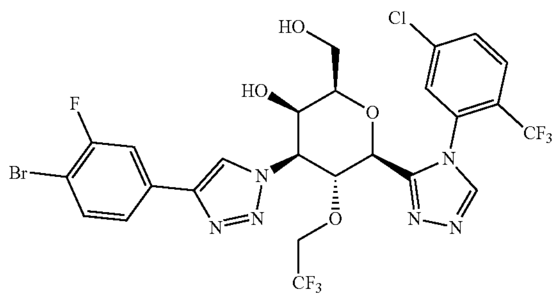 [SMILES: OC[C@H]1O[C@@H](c2nncn2-c2cc(Cl)ccc2C(F)(F)F)[C@H](OCC(F)(F)F)[C@@H](n2cc(-c3ccc(Br)c(F)c3)nn2)[C@H]1O] | MS (ESI) m/z: 716.2. δ 9.14-9.06 (m, 1H), 8.96-8.88 (m, 1H), 8.11-8.04 (m, 1H), 8.02-7.97 (m, 1H), 7.97-7.92 (m, 1H), 7.92-7.86 (m, 1H), 7.85-7.80 (m, 1H), 7.77-7.71 (m, 1H), 5.60-5.25 (m, 1H), 5.24-5.18 (m, 1H), 5.18-5.09 (m, 1H), 5.03-4.59 (m, 1H), 4.51-4.38 (m, 1H), 4.14-4.03 (m, 1H), 3.97-3.89 (m, 1H), 3.89-3.76 (m, 1H), 3.69-3.62 (m, 1H). | 78 |
| 64 | 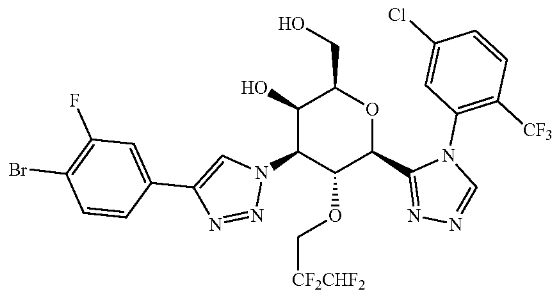 | MS (ESI) m/z: 746.9. δ 9.11 (s, 1H), 8.94 (s, 1H), 8.10-8.05 (m, 1H), 8.03-7.97 (m, 1H), 7.96-7.93 (m, 1H), 7.91-7.87 (m, 1H), 7.86-7.79 (m, 1H), 7.77-7.71 (m, 1H), 5.97-5.69 (m, 1H), 5.58-5.51 (m, 1H), 5.27-5.13 (m, 1H), 5.13-4.89 (m, 1H), 4.79-4.57 (m, 1H), 4.44-4.33 (m, 1H), 4.11-3.96 (m, 1H), 3.94-3.88 (m, 1H), 3.76-3.59 (m, 1H), 3.48-3.44 (m, 1H). | 100 |
| 65 | 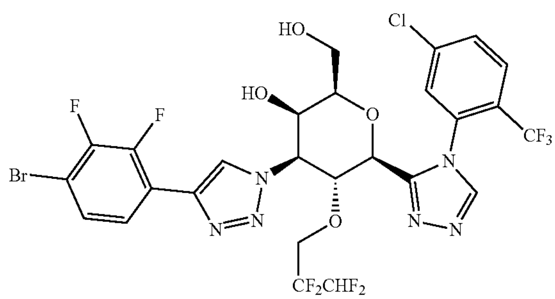 | MS (ESI) m/z: 765.0. δ 8.94-8.87 (m, 1H), 8.84 (d, J = 3.1 Hz, 1H), 8.09-8.04 (m, 1H), 7.94 (s, 2H), 7.92-7.87 (m, 1H), 7.70-7.65 (m, 1H), 5.97-5.71 (m, 1H), 5.56-5.49 (m, 1H), 5.30-4.95 (m, 2H), 4.79-4.57 (m, 1H), 4.39 (br d, J = 8.5 Hz, 1H), 3.94 (br d, J = 6.4 Hz, 2H), 3.71-3.57 (m, 1H) (one proton obscured). | 18 |

Example 66

(atropoisomer of Example 67). 5-((2S,3R,4R,5R, 6R)-4-(4-(4-bromo-2,3-difluorophenyl)-1H-1,2,3-triazol-1-yl)-3,5-dihydroxy-6-(hydroxymethyl)tetrahydro-2H-pyran-2-yl)-4-(5-chloro-2-(trifluoromethyl)phenyl)-2-methyl-2,4-dihydro-3H-1,2,4-triazole-3-thione

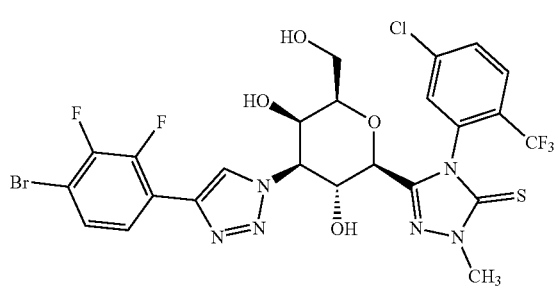 [SMILES: Cn1nc([C@@H]2O[C@H](CO)[C@H](O)[C@H](n3cc(-c4ccc(Br)c(F)c4F)nn3)[C@H]2O)n(-c2cc(Cl)ccc2C(F)(F)F)c1=S]

Example 66 was synthesized according to methods described for the synthesis of Example 26-28, substituting hydrazine hydrate with methylhydrazine where appropriate. MS (ESI) m/z: 697.2 [M+H]+ (Method C). $^1$H NMR (500 MHz, DMSO-$d_6$) δ 8.42-8.39 (m, 1H), 8.07-8.02 (m, 1H), 7.96-7.92 (m, 1H), 7.91-7.86 (m, 1H), 7.67-7.62 (m, 1H), 7.58-7.53 (m, 1H), 4.95-4.88 (m, 1H), 4.57-4.49 (m, 1H), 4.19-4.14 (m, 1H), 3.96-3.90 (m, 1H), 3.82-3.76 (m, 1H), 3.72-3.67 (m, 1H), 3.64-3.56 (m, 1H), 3.50-3.43 (m, 1H), 3.40-3.32 (m, 1H), 2.56 (s, 3H). hGal-3 IC$_{50}$=750 nM.

Example 67

(atropoisomer of Example 66). 5-((2S,3R,4R,5R, 6R)-4-(4-(4-bromo-2,3-difluorophenyl)-1H-1,2,3-triazol-1-yl)-3,5-dihydroxy-6-(hydroxymethyl)tetrahydro-2H-pyran-2-yl)-4-(5-chloro-2-(trifluoromethyl)phenyl)-2-methyl-2,4-dihydro-3H-1,2,4-triazole-3-thione

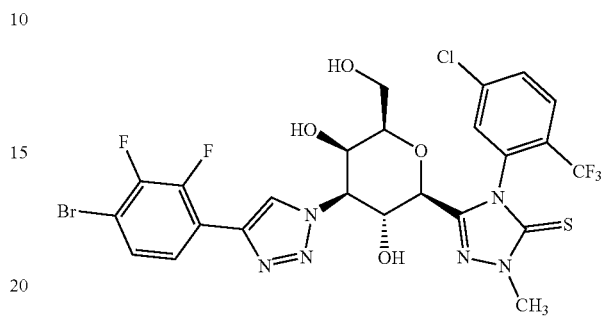

Example 67 was synthesized according to methods described for the synthesis of Example 26-28, substituting hydrazine hydrate with methylhydrazine where appropriate. MS (ESI) m/z: 698.0 [M+H]+ (Method C). $^1$H NMR (500 MHz, DMSO-$d_6$) δ 8.36-8.32 (m, 1H), 8.02-7.99 (m, 1H), 7.96-7.90 (m, 2H), 7.85-7.80 (m, 1H), 7.70-7.64 (m, 1H), 5.76-5.68 (m, 1H), 5.28-5.17 (m, 1H), 5.00-4.86 (m, 1H), 4.69-4.57 (m, 1H), 4.33-4.25 (m, 1H), 3.89-3.82 (m, 1H), 2.56 (s, 3H) (one proton obscured). hGal-3 IC$_{50}$=9.3 nM.

Example 68

(2R,3R,4S,5R,6S)-6-(4-(benzo[d]thiazol-6-yl)-4H-1,2,4-triazol-3-yl)-4-(4-(4-bromo-3,5-difluorophenyl)-1H-1,2,3-triazol-1-yl)-5-(2,2-difluoroethoxy)-2-(hydroxymethyl)tetrahydro-2H-pyran-3-ol

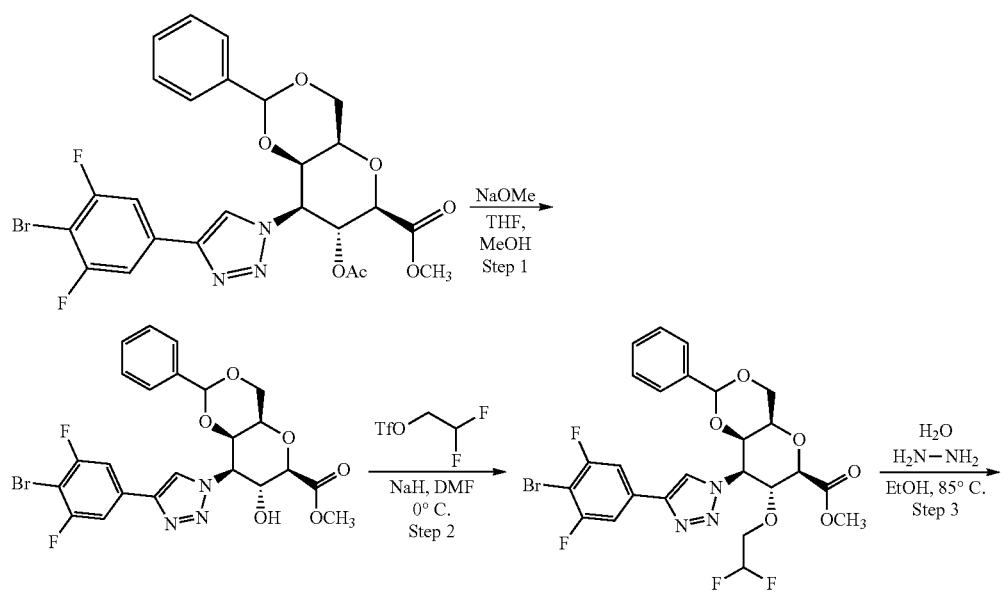

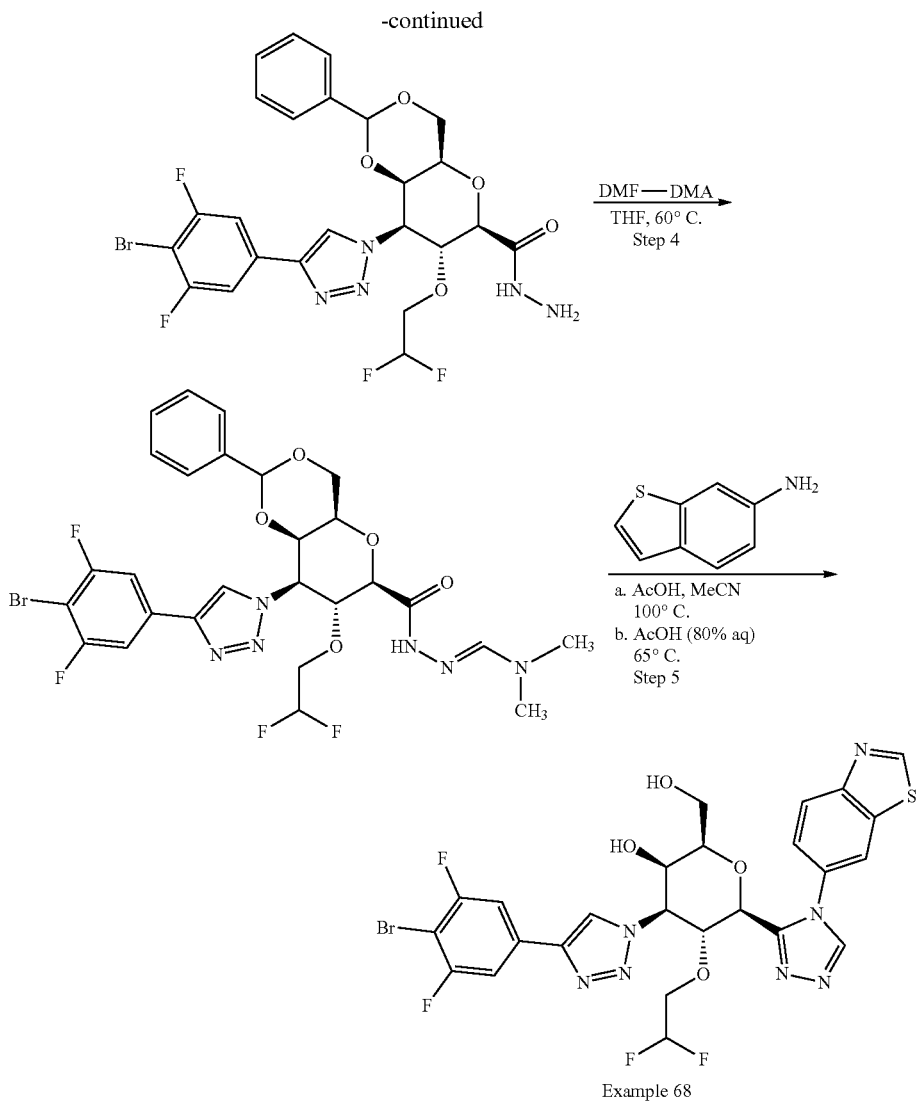

Example 68

Step 1: Preparation of methyl (4aR,6R,7R,8R,8aR)-8-(4-(4-bromo-3,5-difluorophenyl)-1H-1,2,3-triazol-1-yl)-7-hydroxy-2-phenylhexahydropyrano[3,2-d][1,3]dioxine-6-carboxylate To a 250 mL round bottomed flask were added methyl (4aR,6R,7R,8S,8aR)-7-acetoxy-8-(4-(4-bromo-3,5-difluorophenyl)-1H-1,2,3-triazol-1-yl)-2-phenylhexahydropyrano[3,2-d][1,3]dioxine-6-carboxylate (1.0 g, 1.7 mmol), THF (17 mL), MeOH (17 mL), followed by sodium methoxide (25% solution in MeOH) (0.39 mL, 1.7 mmol). The reaction was stirred under $N_2$. After 18 h, the solution was neutralized with 1 N HCl (1 mL), the solvent was concentrated, and the residue was co-evaporated with toluene. To the resultant residue was added sodium bicarbonate (1.4 g, 17 mmol), iodomethane (0.53 mL, 8.4 mmol), and DMF (30 mL). The reaction was stirred under $N_2$. After 18 h, the reaction was diluted with water (150 mL) and extracted with EtOAc (2×75 mL). The organic phase was combined, washed with brine, dried over $Na_2SO_4$, filtered and concentrated. The residue was purifed by trituration from ether. The product was dried in vacuo to afford the title compound (0.7 g, 1.3 mmol, 75% yield) as a white solid. MS (ESI) m/z: 554.0 [M+H]+ (Method B). $^1$H NMR (400 MHz, DMSO-$d_6$) δ 9.02-8.93 (m, 1H), 7.86-7.74 (m, 2H), 7.34 (s, 5H), 5.82-5.71 (m, 1H), 5.58-5.51 (m, 1H), 5.23-5.15 (m, 1H), 4.57-4.45 (m, 2H), 4.20-4.08 (m, 3H), 4.01-3.93 (m, 1H), 3.74 (s, 3H).

Step 2: Preparation of methyl (4aR,6R,7R,8R,8aR)-8-(4-(4-bromo-3,5-difluorophenyl)-1H-1,2,3-triazol-1-yl)-7-(2,2-difluoroethoxy)-2-phenylhexahydropyrano[3,2-d][1,3]dioxine-6-carboxylate To a 25 mL round bottomed flask were added methyl (4aR,6R,7R,8R,8aR)-8-(4-(4-bromo-3,5-difluorophenyl)-1H-1,2,3-triazol-1-yl)-7-hydroxy-2-phenylhexahydropyrano[3,2-d][1,3]dioxine-6-carboxylate (0.40 g, 0.72 mmol) and DMF (15 mL). The reaction was cooled to 0° C., then NaH (60% dispersion in mineral oil) (0.087 g, 2.2 mmol) was added. After stirring at this temperature for 45 min, 2,2-difluoroethyl trifluoromethanesulfonate (0.29 ml, 2.2 mmol) was added and the reaction was continued at 0° C. After stirring at this temperature for 1 h, the reaction was quenched with sat. $NH_4Cl$ (100 mL) and extracted with EtOAc (2×50 mL). The organic phase was combined, washed with brine, dried over Na₂SO₄, filtered and concentrated. The solid was triturated with ether, the product was collected by vacuum filtration and dried in vacuo to afford the title compound (0.43 g, 0.70 mmol, 96% yield) as an off-white solid. MS (ESI) m/z: 618.0 [M+H]+ (Method B). ¹H NMR (500 MHz, DMSO-d₆) δ 9.20-9.12 (m, 1H), 7.75-7.70 (m, 2H), 7.38 (s, 5H), 5.74-5.45 (m, 3H), 4.66-4.56 (m, 1H), 4.55-4.46 (m, 2H), 4.40-4.30 (m, 1H), 4.21-4.08 (m, 2H), 4.03-3.97 (m, 1H), 3.79 (s, 3H), 3.68-3.58 (m, 1H).

Step 3: Preparation of (4aR,6R,7R,8R,8aR)-8-(4-(4-bromo-3,5-difluorophenyl)-1H-1,2,3-triazol-1-yl)-7-(2,2-difluoroethoxy)-2-phenylhexahydropyrano[3,2-d][1,3]dioxine-6-carbohydrazide To a 100 mL pear shaped flask were added methyl (4aR,6R,7R,8R,8aR)-8-(4-(4-bromo-3,5-difluorophenyl)-1H-1,2,3-triazol-1-yl)-7-(2,2-difluoroethoxy)-2-phenylhexahydropyrano[3,2-d][1,3]dioxine-6-carboxylate (0.43 g, 0.70 mmol) and EtOH (30 mL). To this mixture was added hydrazine hydrate (0.34 mL, 7.0 mmol) and the reaction was stirred at 85° C. After 48 h, the solvent was concentrated and the resultant semisolid was precipitated with ether, sonicated, and the solid product was collected by vacuum filtration. The filter cake was washed with ether, and the product was dried in vacuo to afford the title compound (0.36 g, 0.58 mmol, 84% yield) as a tan solid. MS (ESI) m/z: 618.1 [M+H]+ (Method B). ¹H NMR (500 MHz, DMSO-d₆) δ 9.75-9.68 (m, 1H), 9.20-9.16 (m, 1H), 7.78-7.72 (m, 2H), 7.36 (s, 5H), 5.78-5.74 (m, 2H), 5.70-5.53 (m, 2H), 5.46-5.38 (m, 1H), 4.72-4.62 (m, 1H), 4.14-4.07 (m, 2H), 3.99-3.91 (m, 1H), 3.90-3.84 (m, 1H), 3.76-3.65 (m, 1H).

Step 4: Preparation of (E)-N'-((4aR,6R,7R,8R,8aR)-8-(4-(4-bromo-3,5-difluorophenyl)-1H-1,2,3-triazol-1-yl)-7-(2,2-difluoroethoxy)-2-phenylhexahydropyrano[3,2-d][1,3]dioxine-6-carbonyl)-N,N-dimethylformohydrazonamide To a 100 mL pear shaped flask were added (4aR,6R,7R,8R,8aR)-8-(4-(4-bromo-3,5-difluorophenyl)-1H-1,2,3-triazol-1-yl)-7-(2,2-difluoroethoxy)-2-phenylhexahydropyrano[3,2-d][1,3]dioxine-6-carbohydrazide (70 mg, 0.11 mmol), THF (5 mL), and DMF-DMA (0.018 mL, 0.14 mmol). The reaction was stirred at 65° C. After 2 h, the solvent was concentrated, the residue was triturated with ether, and the solid was collected by vacuum filtration. The product was dried in vacuo to afford the title compound (76 mg, 0.11 mmol, 100% yield) as an off-white solid. MS (ESI) m/z: 672.9 [M+H]+ (Method B).

Step 5: Preparation of Example 68

Step 5a: To a 10 mL pear shaped flask were added (E)-N'-((4aR,6R,7R,8R,8aR)-8-(4-(4-bromo-3,5-difluorophenyl)-1H-1,2,3-triazol-1-yl)-7-(2,2-difluoroethoxy)-2-phenylhexahydropyrano[3,2-d][1,3]dioxine-6-carbonyl)-N,N-dimethylformohydrazonamide (76 mg, 0.11 mmol), benzo[d]thiazol-6-amine (26 mg, 0.17 mmol), MeCN (1 mL), and AcOH (1 mL). The reaction was stirred at 105° C. After 1.5 h, the solvent was concentrated and the residue was dissolved in toluene and concentrated again. The residue was purified by flash column chromatography (24 g silica gel cartridge; A=Hex, B=EtOAc; 15 min grad.; 0% B to 10% B; flow rate=24 mL/min, product comes off at 100% B). The pure fractions were combined, concentrated and dried in vacuo.

Step 2b: The product of Step 5a was dissolved in AcOH (80% aq) (3 mL) and stirred at 75° C. After 48 h, the solvent was concentrated and the residue was co-evaporated with toluene (2×). The residue was dissolved in MeOH (1 mL) and THF (1 mL), then NaOMe was added (1 drop, 25% solution in MeOH). After 15 min, the reaction was neutralized with 1 N HCl, the solvent was concentrated and the residue was purified by preparative HPLC (Column: XBridge C18, 200 mm×19 mm, 5-μm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 20% B, 20-60% B over 25 minutes, then a 4-minute hold at 100% B; Flow Rate: 20 mL/min; Column Temperature: 25 C. Fraction collection was triggered by MS and UV signals). Fractions containing the desired product were combined and dried via centrifugal evaporation to afford the title compound (12 mg, 0.018 mmol, 16% yield). MS (ESI) m/z: 670.0 [M+H]+ (Method C). ¹H NMR (500 MHz, DMSO-d₆) δ 9.56 (s, 1H), 9.15 (s, 1H), 9.04 (s, 1H), 8.57 (d, J=1.9 Hz, 1H), 8.30 (d, J=8.7 Hz, 1H), 7.94 (s, 1H), 7.82-7.79 (m, 2H), 5.67-5.54 (m, 1H), 5.53-5.32 (m, 1H), 5.25-5.15 (m, 1H), 5.10-5.05 (m, 1H), 4.63-4.52 (m, 1H), 4.00-3.91 (m, 1H), 3.89-3.81 (m, 1H), 3.75-3.65 (m, 1H) (two protons obscured). hGal-3 IC₅₀=25 nM.

Examples 69 to 75 in the table below were synthesized according to methods described for Example 68 using appropriate starting materials.

| EX # | Structure | LCMS (Method C, unless otherwise indicated)/ ¹H NMR (500 MHz, DMSO-d₆, unless otherwise indicated) | hGal-3 IC₅₀ (nM) |
|---|---|---|---|
| 69 | (structure) | MS (ESI) m/z: 698.3. δ 9.08-9.05 (m, 1H), 8.95-8.91 (m, 2H), 8.59-8.54 (m, 1H), 8.44 (d, J = 2.1 Hz, 1H), 8.12 (d, J = 1.8 Hz, 1H), 7.82-7.78 (m, 2H), 7.78-7.73 (m, 1H), 5.58-5.32 (m, 1H), 5.13-5.06 (m, 1H), 4.97-4.88 (m, 1H), 4.53-4.45 (m, 1H), 3.92-3.85 (m, 1H), 3.79-3.66 (m, 1H), 3.66-3.58 (m, 1H), 3.46-3.39 (m, 1H) (two protons obscured). | 130 |

-continued

| EX # | Structure | LCMS (Method C, unless otherwise indicated)/ $^1$H NMR (500 MHz, DMSO-$d_6$, unless otherwise indicated) | hGal-3 IC$_{50}$ (nM) |
|---|---|---|---|
| 70 | 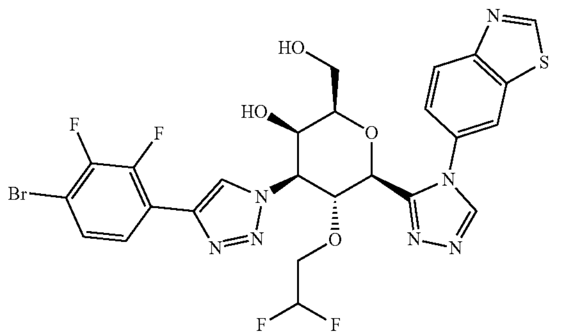 [SMILES: OC[C@H]1O[C@@H](c2nncn2-c2ccc3ncsc3c2)[C@H](OCC(F)F)[C@@H](n2cc(-c3ccc(Br)c(F)c3F)nn2)[C@H]1O] | MS (ESI) m/z: 670.1. δ 9.55 (s, 1H), 9.02 (s, 1H), 8.82-8.77 (m, 1H), 8.59-8.54 (m, 1H), 8.32-8.26 (m, 1H), 7.93-7.87 (m, 1H), 7.82-7.76 (m, 1H), 7.71-7.62 (m, 1H), 5.62-5.34 (m, 1H), 5.22-5.16 (m, 1H), 5.15-5.07 (m, 1H), 4.60-4.51 (m, 1H), 4.04-3.94 (m, 1H), 3.87-3.77 (m, 1H), 3.72-3.55 (m, 2H), 3.42-3.32 (m, 1H) (one proton obscured). | 11 |
| 71 | 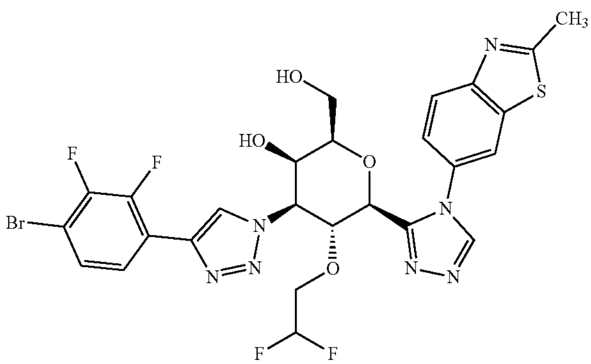 [SMILES: Cc1nc2ccc(-n3cnnc3[C@@H]3O[C@H](CO)[C@H](O)[C@H](n4cc(-c5ccc(Br)c(F)c5F)nn4)[C@H]3OCC(F)F)cc2s1] | MS (ESI) m/z: 684.1. δ 8.98 (s, 1H), 8.77 (d, J = 2.7 Hz, 1H), 8.40 (d, J = 1.8 Hz, 1H), 8.11-8.07 (m, 1H), 7.91-7.85 (m, 1H), 7.72-7.68 (m, 1H), 7.68-7.62 (m, 1H), 5.59-5.34 (m, 1H), 5.22-5.15 (m, 1H), 5.14-5.06 (m, 1H), 4.57-4.46 (m, 1H), 4.02-3.93 (m, 1H), 3.84-3.75 (m, 1H), 3.70-3.56 (m, 2H), 3.41-3.26 (m, 1H) 2.86 (s, 3H) (one proton obscured). | 20 |
| 72 | 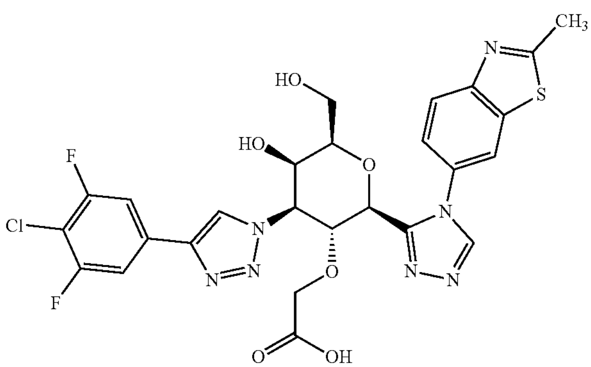 [SMILES: Cc1nc2ccc(-n3cnnc3[C@@H]3O[C@H](CO)[C@H](O)[C@H](n4cc(-c5cc(F)c(Cl)c(F)c5)nn4)[C@H]3OCC(=O)O)cc2s1] | MS (ESI) m/z: 634.2. δ 9.12 (s, 1H), 8.96 (s, 1H), 8.42 (d, J = 2.1 Hz, 1H), 8.14-8.08 (m, 1H), 7.90-7.84 (m, 2H), 7.75-7.69 (m, 1H), 5.22-5.13 (m, 1H), 5.09-4.99 (m, 1H), 4.61-4.47 (m, 1H), 4.22-4.11 (m, 1H), 4.00-3.92 (m, 1H), 3.86-3.80 (m, 1H), 3.80-3.72 (m, 1H), 3.62-3.51 (m, 1H), 2.88 (s, 3H) (one proton obscured). | 16 |
| 73 | 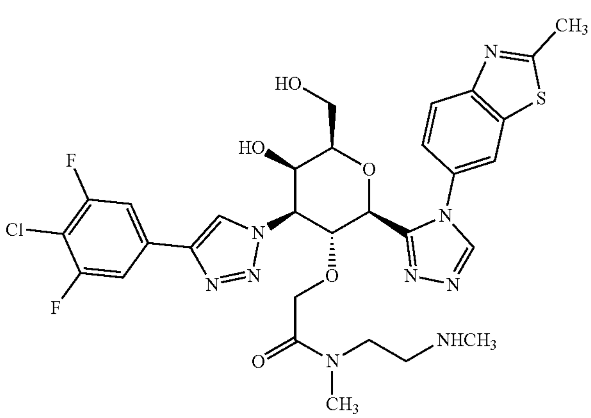 [SMILES: CNCCN(C)C(=O)CO[C@@H]1[C@@H](n2cc(-c3cc(F)c(Cl)c(F)c3)nn2)[C@@H](O)[C@@H](CO)O[C@H]1c1nncn1-c1ccc2nc(C)sc2c1] | MS (ESI) m/z: 704.1 (Method B). δ 9.22 (s, 1H), 8.99 (s, 1H), 8.47-8.43 (m, 1H), 8.16-8.11 (m, 1H), 7.91-7.86 (m, 2H), 7.77-7.71 (m, 1H), 5.56-5.45 (m, 1H), 5.25-5.17 (m, 1H), 5.14-5.05 (m, 1H), 5.03-4.84 (m, 1H), 4.59-4.50 (m, 1H), 4.33-4.25 (m, 1H), 3.96-3.93 (m, 1H), 3.86-3.80 (m, 2H), 3.64-3.55 (m, 2H), 3.55-3.45 (m, 2H), 2.89 (s, 6H) (three protons obscured). | 54 |

| EX # | Structure | LCMS (Method C, unless otherwise indicated)/ ¹H NMR (500 MHz, DMSO-d₆, unless otherwise indicated) | hGal-3 IC₅₀ (nM) |
|---|---|---|---|
| 74 | 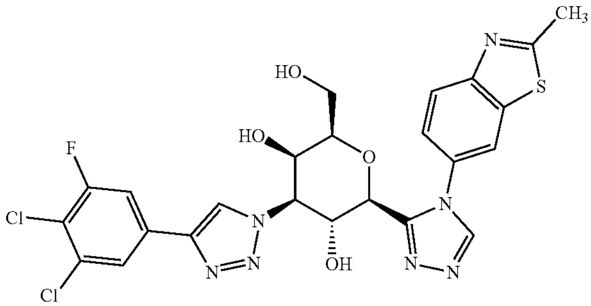 [SMILES: Cc1nc2ccc(-n3cnnc3[C@@H]3O[C@H](CO)[C@H](O)[C@H](n4cc(-c5cc(F)c(Cl)c(Cl)c5)nn4)[C@H]3O)cc2s1] | MS (ESI) m/z: 594.2. δ 8.95 (d, J = 7.3 Hz, 2H), 8.45 (d, J = 2.1 Hz, 1H), 8.12-8.07 (m, 2H), 8.01-7.97 (m, 1H), 7.77-7.71 (m, 1H), 5.44-5.40 (m, 1H), 5.39-5.34 (m, 1H), 5.06-4.98 (m, 1H), 4.96-4.90 (m, 2H), 4.45-4.36 (m, 1H), 4.01-3.93 (m, 1H), 3.82-3.74 (m, 1H), 3.65-3.56 (m, 1H), 3.55-3.47 (m, 1H), 2.88 (s, 3H). | 35 |
| 75 | 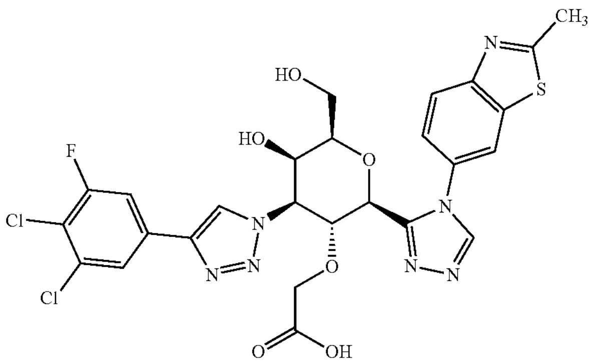 [SMILES: Cc1nc2ccc(-n3cnnc3[C@@H]3O[C@H](CO)[C@H](O)[C@H](n4cc(-c5cc(F)c(Cl)c(Cl)c5)nn4)[C@H]3OCC(=O)O)cc2s1] | MS (ESI) m/z: 650.2. δ 9.18 (s, 1H), 8.96 (s, 1H), 8.45-8.41 (m, 1H), 8.10 (s, 2H), 8.01-7.95 (m, 1H), 7.76-7.70 (m, 1H), 5.22-5.14 (m, 1H), 5.10-5.00 (m, 1H), 4.62-4.48 (m, 1H), 4.18-4.09 (m, 1H), 3.98-3.93 (m, 1H), 3.87-3.78 (m, 1H), 3.77-3.69 (m, 1H), 3.61-3.54 (m, 1H), 3.53-3.43 (m, 1H), 2.89 (s, 3H). | 18 |

We claim:

1. A compound selected from:

-continued
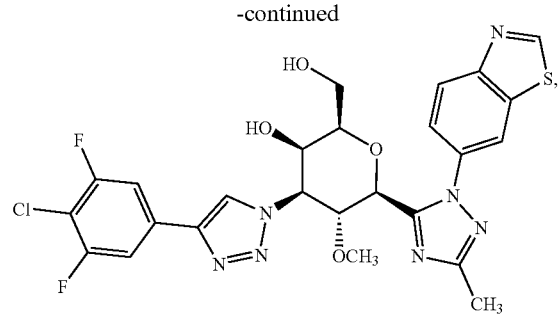
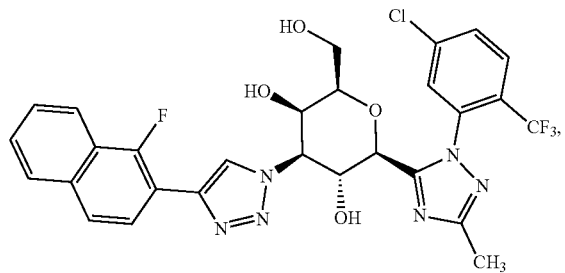
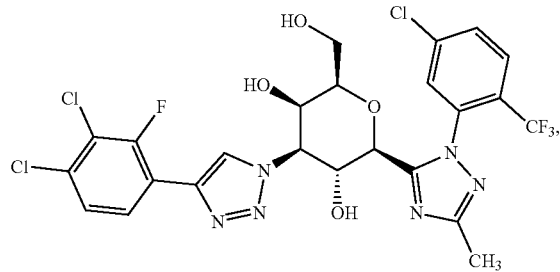
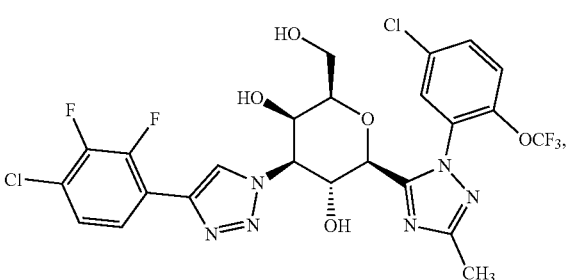
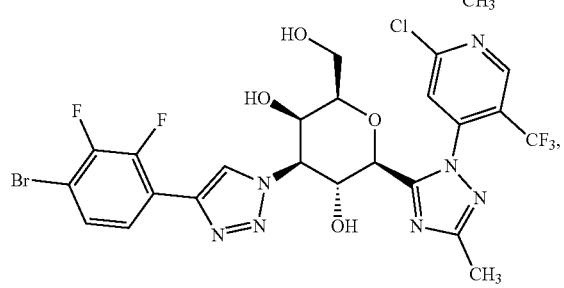
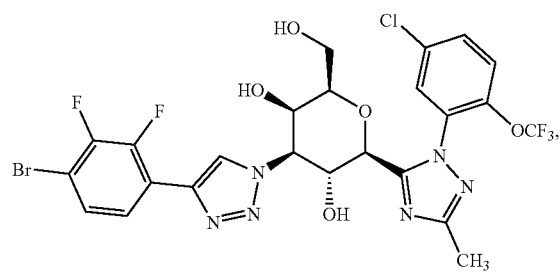
-continued
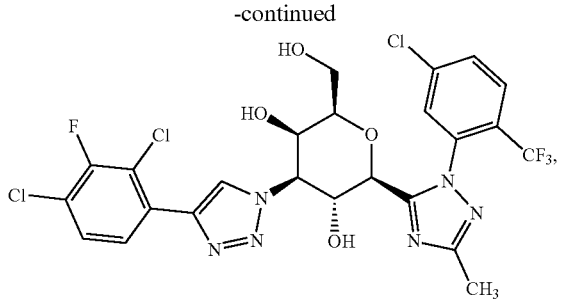
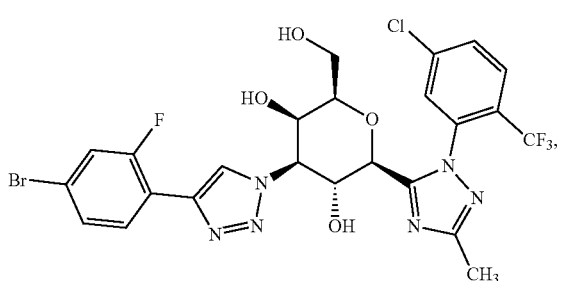
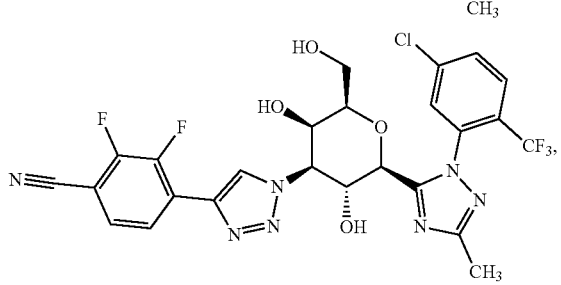
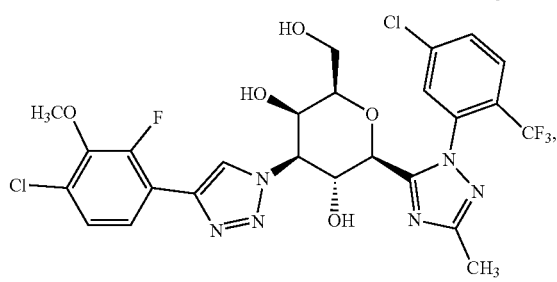
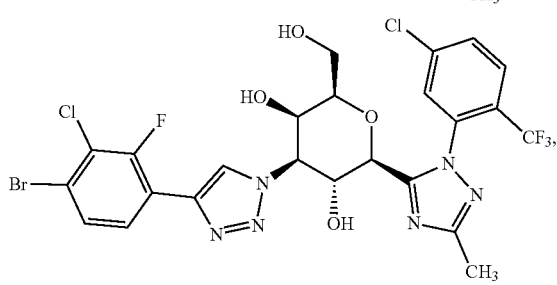
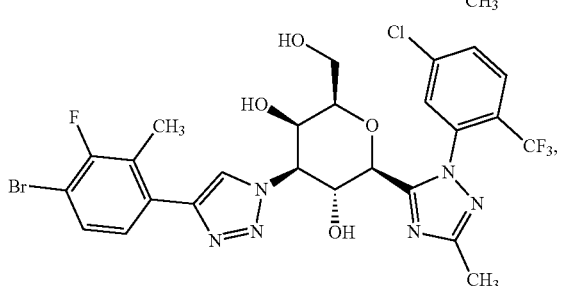

-continued
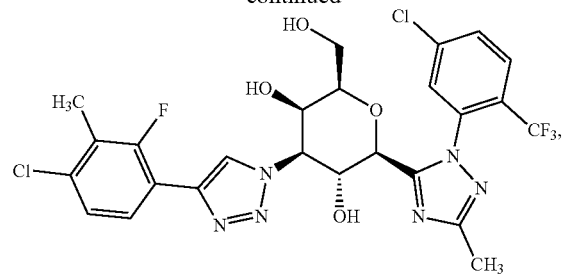
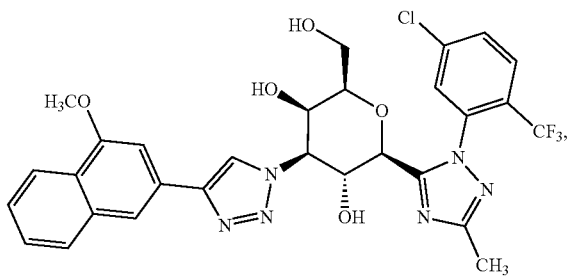
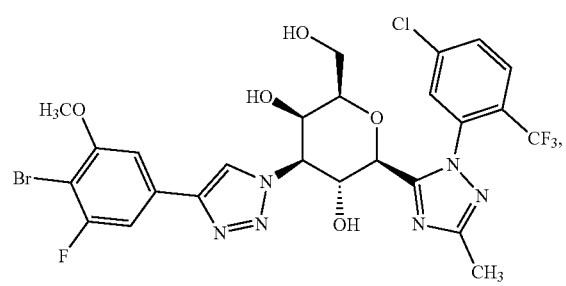
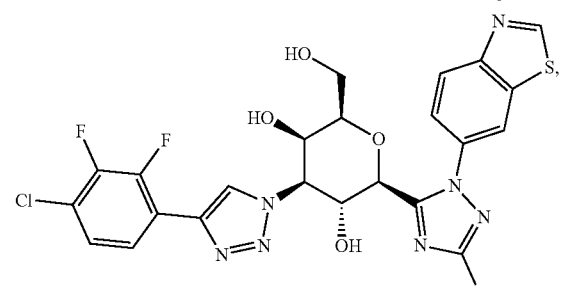
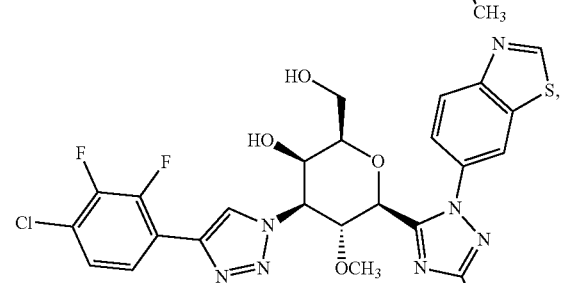
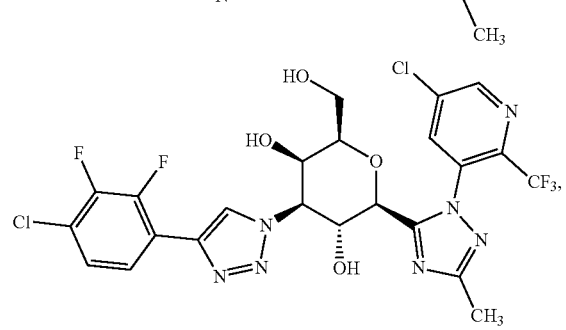
-continued
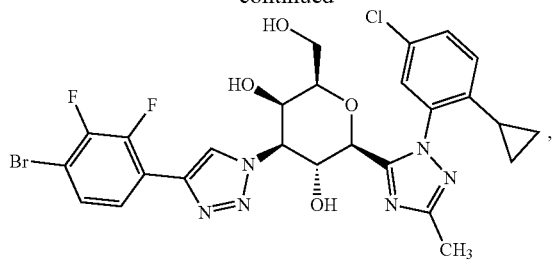
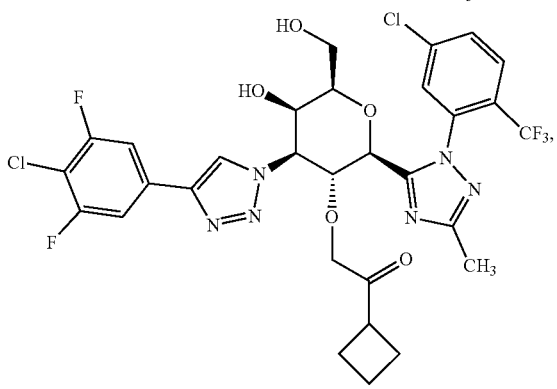
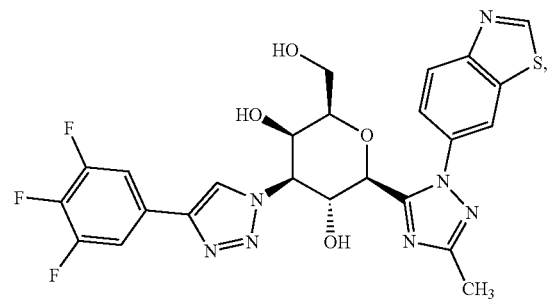
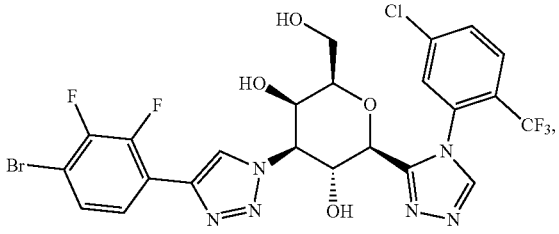
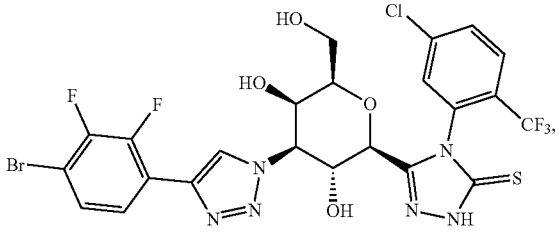
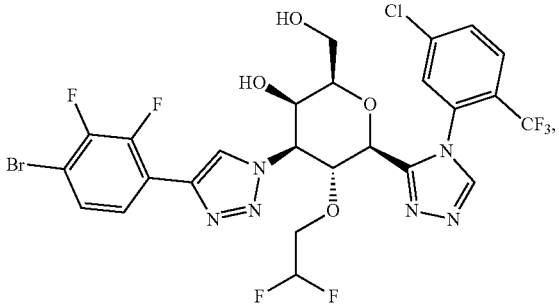

-continued
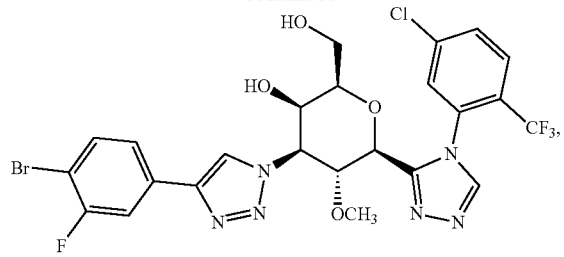
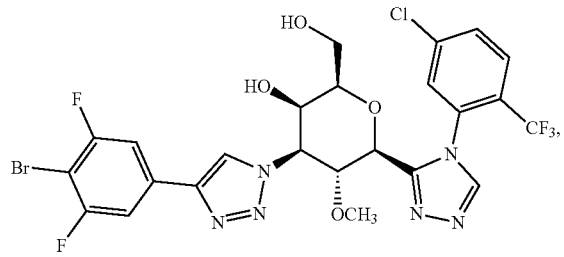
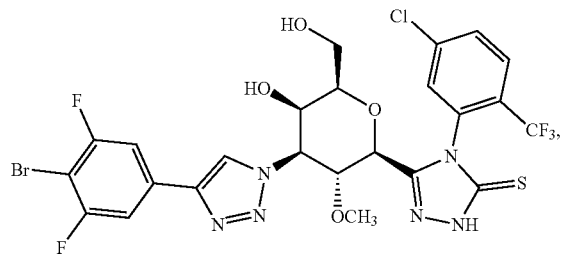
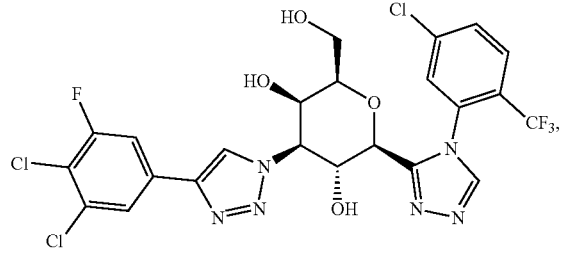
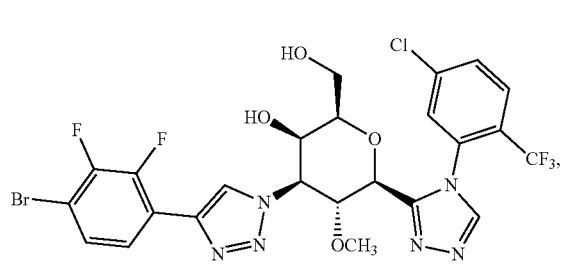
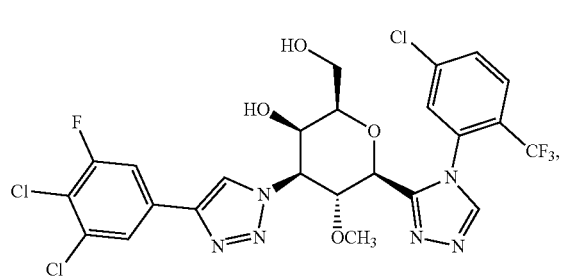
-continued
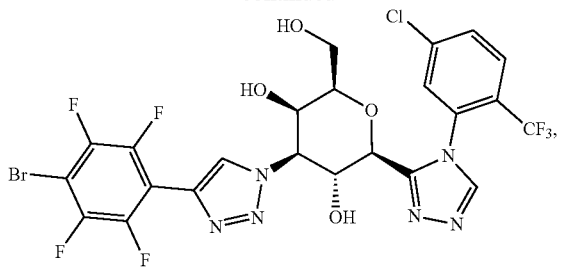
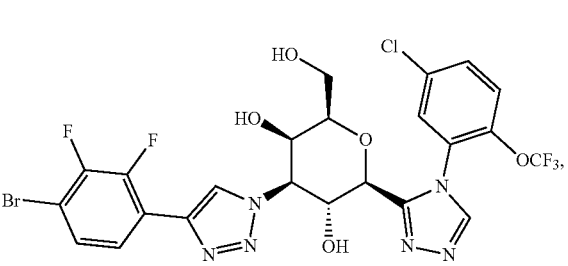
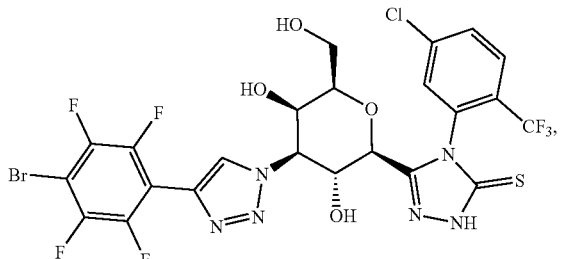
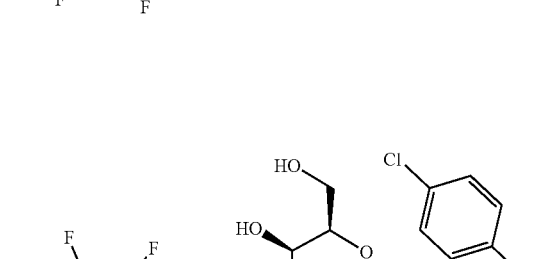
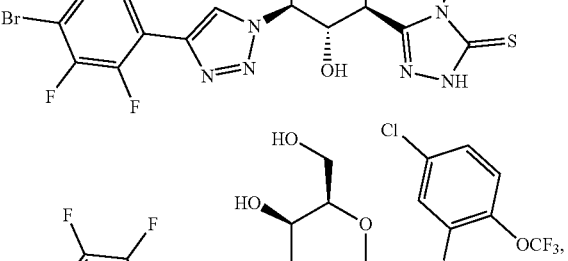
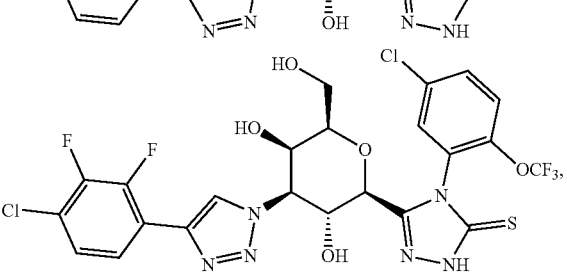

77
-continued
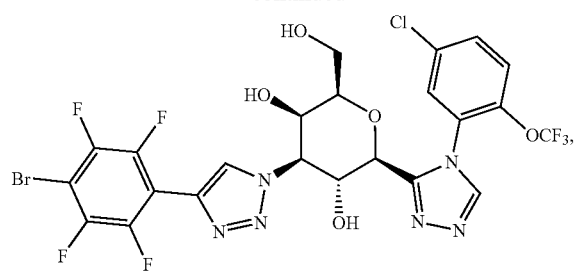
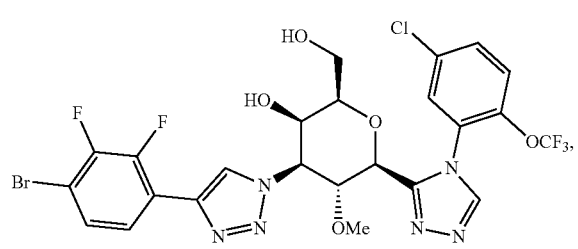
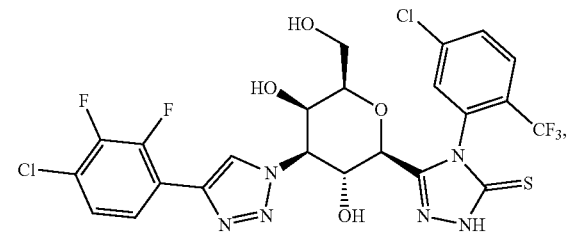
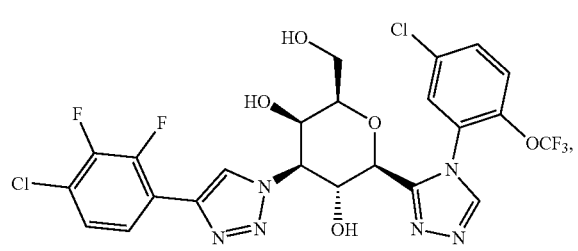
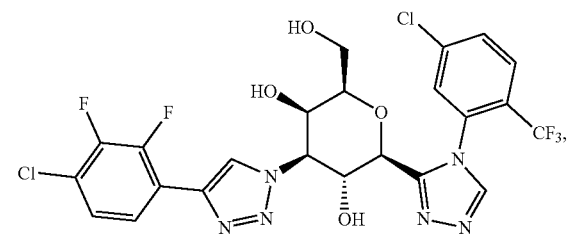
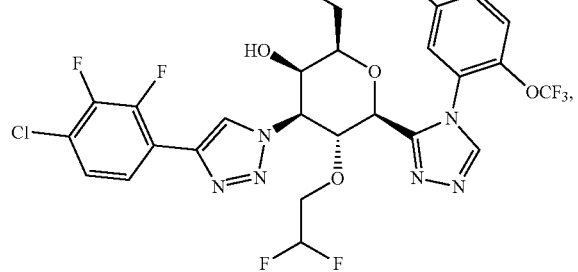
78
-continued
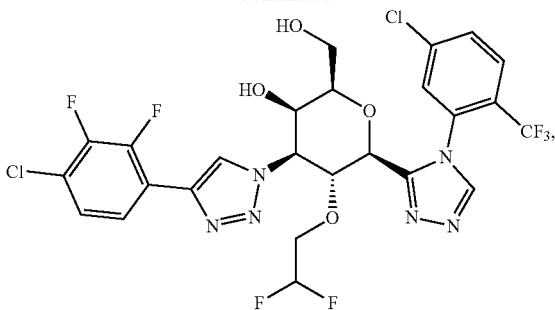
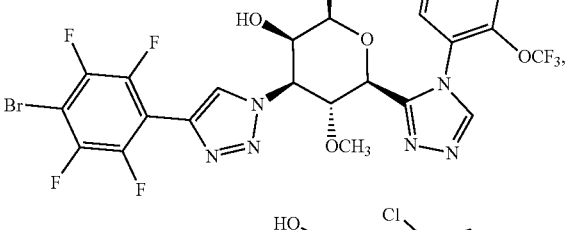
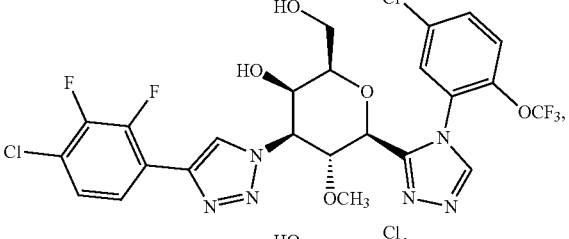
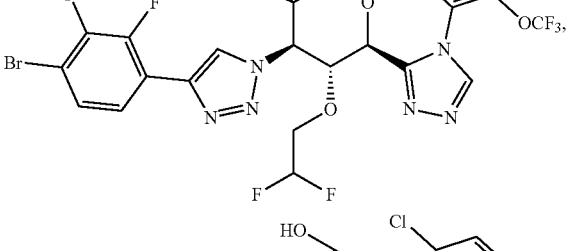
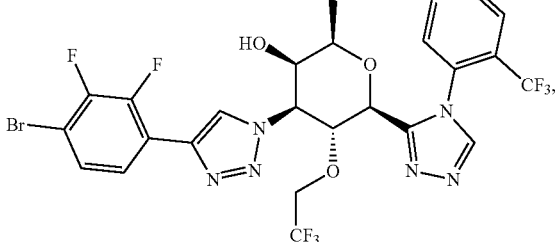
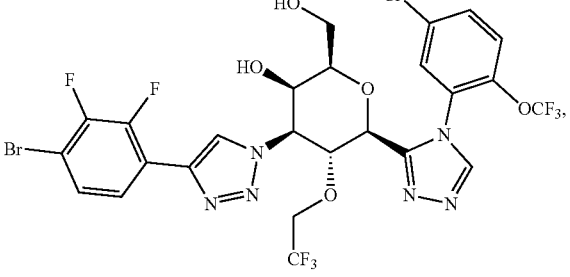

-continued
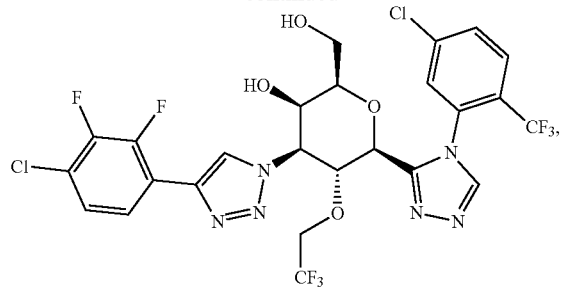
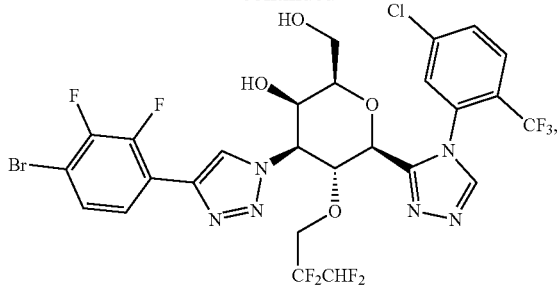
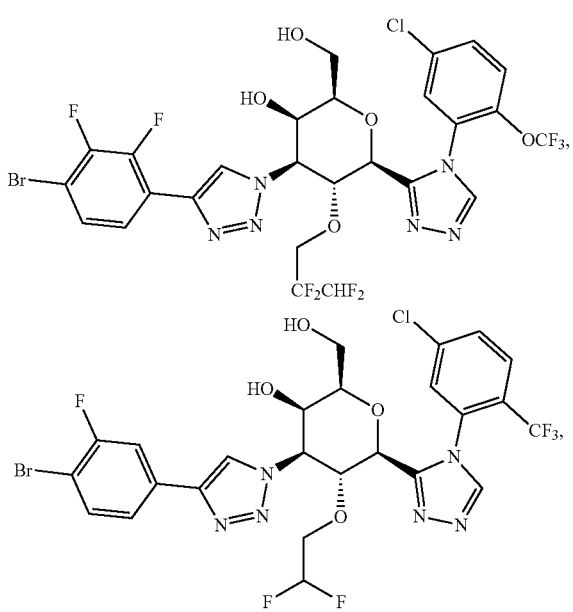
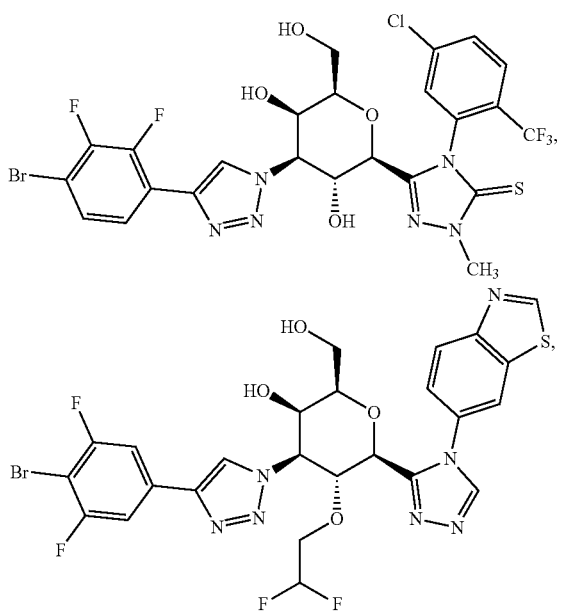
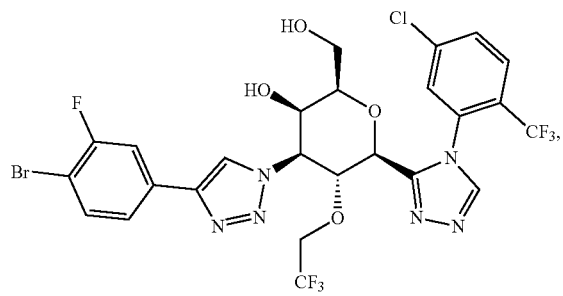
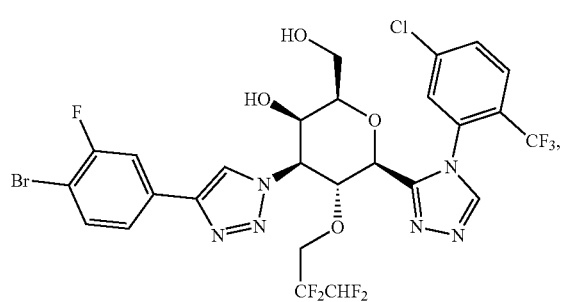

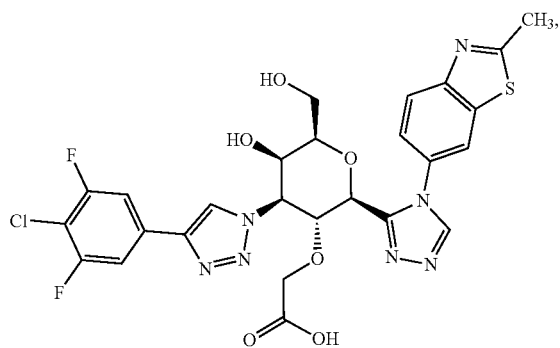

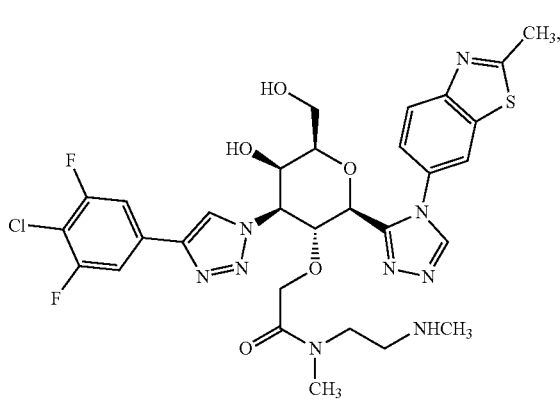

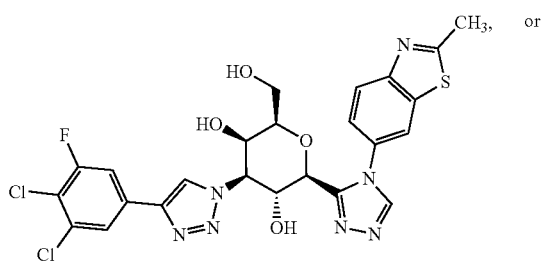

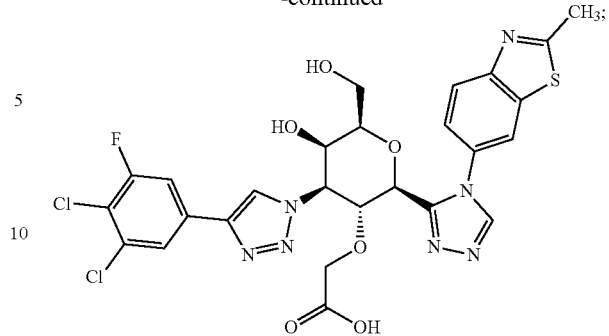

or a pharmaceutically acceptable salt thereof.

2. A composition comprising a therapeutically effective amount of a compound or a pharmaceutically acceptable salt thereof of claim 1, and one or more pharmaceutically acceptable carriers.

3. A method for treating fibrosis of organs selected from liver, kidney, lung, heart and skin; liver diseases and conditions selected from acute hepatitis, chronic hepatitis, liver fibrosis, liver cirrhosis, portal hypertension, regenerative failure, non-alcoholic steatohepatitis (NASH), liver hypofunction, and hepatic blood flow disorder); cell proliferative diseases, cancers, and conditions selected from solid tumor, solid tumor metastasis, vascular fibroma, myeloma, multiple myeloma, Kaposi's sarcoma, leukemia, chronic lymphocytic leukemia (CLL)) and invasive metastasis of cancer cell; inflammatory diseases and conditions selected from psoriasis, nephropathy, and pneumonia; gastrointestinal tract diseases and conditions selected from irritable bowel syndrome (IBS), inflammatory bowel disease (IBD), and abnormal pancreatic secretion; renal diseases and conditions, urinary tract-associated diseases and conditions selected from benign prostatic hyperplasia or symptoms associated with neuropathic bladder disease, spinal cord tumor, hernia of intervertebral disk, spinal canal stenosis, and symptoms derived from diabetes; lower urinary tract diseases and conditions of obstruction of lower urinary tract; inflammatory diseases and conditions of lower urinary tract selected from dysuria and frequent urination; pancreatic diseases and conditions, abnormal angiogenesis-associated diseases and conditions of arterial obstruction; scleroderma, brain-associated diseases and conditions selected from cerebral infarction and cerebral hemorrhage; neuropathic pain and peripheral neuropathy, ocular diseases and conditions selected from age-related macular degeneration (AMD), diabetic retinopathy, proliferative vitreoretinopathy (PVR), cicatricial pemphigoid, and glaucoma filtration surgery scarring; comprising administering a therapeutically effective amount of a compound of claim 1, or a pharmaceutically acceptable salt thereof of to a patient.

4. A method for treating a disease or condition selected from renal fibrosis, pulmonary fibrosis, hepatic fibrosis, arterial fibrosis, and systemic sclerosis; comprising administering a therapeutically effective amount of a compound of claim 1, or a pharmaceutically acceptable salt thereof of to a patient.

\* \* \* \* \*

UNITED STATES PATENT AND TRADEMARK OFFICE
CERTIFICATE OF CORRECTION

Page 1 of 1

PATENT NO. : 12,275,719 B2
APPLICATION NO. : 17/439845
DATED : April 15, 2025
INVENTOR(S) : Chunjian Liu et al.

It is certified that error appears in the above-identified patent and that said Letters Patent is hereby corrected as shown below:

In the Specification

Column 1
Line 8, after "application" insert -- is a 371 of International Application No. PCT/US2020/024548 filed on March 25, 2020, which --.

Signed and Sealed this
Nineteenth Day of August, 2025

Coke Morgan Stewart
*Acting Director of the United States Patent and Trademark Office*